United States Patent [19]

Norman et al.

[11] Patent Number: 5,719,163

[45] Date of Patent: Feb. 17, 1998

[54] SUBSTITUTED OXAZOLYL COMPOUNDS FOR THE TREATMENT OF INFLAMMATION

[75] Inventors: Bryan H. Norman, Indianapolis, Ind.; Len F. Lee, St. Charles, Mo.; Jaime L. Masferrer, Ballwin, Mo.; John J. Talley, St. Louis, Mo.

[73] Assignee: G.D. Searle & Co., Skokie, Ill.

[21] Appl. No.: 535,227

[22] PCT Filed: May 19, 1994

[86] PCT No.: PCT/US94/05395

§ 371 Date: Oct. 27, 1995

§ 102(e) Date: Oct. 27, 1995

[87] PCT Pub. No.: WO94/27980

PCT Pub. Date: Dec. 8, 1994

Related U.S. Application Data

[63] Continuation-in-part of Ser. No. 65,730, May 21, 1993, Pat. No. 5,380,738.

[51] Int. Cl.$^6$ ............... C07D 413/06; A61K 31/42; A61K 31/47

[52] U.S. Cl. ............... 514/311; 514/312; 514/314; 514/340; 514/374; 514/376; 546/152; 546/153; 546/176; 546/180; 546/275; 548/215; 548/225; 548/235

[58] Field of Search ............... 514/374, 376, 514/312, 314, 311, 340; 548/215, 225, 235; 546/152, 153, 176, 180, 275

[56] References Cited

U.S. PATENT DOCUMENTS

| | | | |
|---|---|---|---|
| 3,578,671 | 5/1971 | Brown | 260/307 |
| 3,895,024 | 7/1975 | Hafeli | 260/307 C |
| 3,901,908 | 8/1975 | Fitzi et al. | 260/309 |
| 4,001,228 | 1/1977 | Mattalia | 260/247.1 M |
| 4,051,250 | 9/1977 | Dahm et al. | 424/272 |
| 4,143,047 | 3/1979 | Harrison | 260/307 R |
| 4,489,084 | 12/1984 | Haviv et al. | 424/270 |
| 4,590,205 | 5/1986 | Haber | 514/438 |
| 4,632,930 | 12/1986 | Carini et al. | 514/365 |
| 4,775,687 | 10/1988 | Meguro et al. | 514/369 |
| 4,791,124 | 12/1988 | Lutomski et al. | 514/365 |
| 4,812,470 | 3/1989 | Rogers et al. | 514/365 |
| 4,820,827 | 4/1989 | Haber | 549/78 |
| 5,134,142 | 7/1992 | Matsuo et al. | 514/255 |
| 5,380,738 | 1/1995 | Norman et al. | 514/374 |
| 5,403,852 | 4/1995 | Barreau et al. | 514/374 |

FOREIGN PATENT DOCUMENTS

| | | |
|---|---|---|
| 92/21665 | 12/1992 | WIPO . |
| 94/15932 | 7/1994 | WIPO . |
| 94/27980 | 12/1994 | WIPO . |
| 92/00501 | 1/1995 | WIPO . |

OTHER PUBLICATIONS

N. Meanwell et al, *J. Med. Chem.*, 35, 3498 (1992).
r. Cremylin et al, *J. Heterocycl. Chem.* 22, 1211 (1985).
T. Van Es and O.G. Backeberg, *J. Chem. Soc.*, 1363 (1963).

*Primary Examiner*—Joseph McKane

[57] ABSTRACT

A class of substituted oxazolyl compounds is described for use in treating inflammation and inflammation-related disorders. Compounds of particular interest are defined by Formula I:

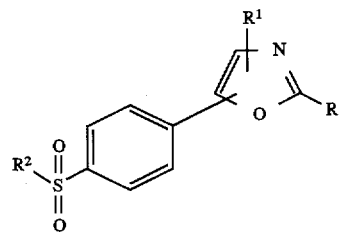

wherein R is selected from alkyl, hydroxyalkyl, haloalkyl, cycloalkyl, cycloalkylalkyl, aryl optionally substituted at a substitutable position by carboxy, alkyl, alkoxy and halo, aralkyl optionally substituted at a substitutable position on the aryl radical by carboxy, alkyl, alkoxy and halo, aryloxyalkyl optionally substituted at a substitutable position on the aryl radical with halo, carboxy, alkyl and alkoxy, aralkoxyalkyl optionally substituted at a substitutable position by alkyl, carboxy, alkoxy and halo, heteroaryloxyalkyl optionally substituted at a substitutable position with halo, carboxy, alkyl and alkoxy, alkoxycarbonylalkyl, carboxyalkyl and aminocarbonylalkyl; wherein $R^1$ is selected from cycloalkyl, cycloalkenyl, heteroaryl and aryl optionally substituted at a substitutable position by alkyl, alkoxy and halo, and wherein $R^2$ is alkyl; or a pharmaceutically-acceptable salt thereof; provided $R^1$ is not phenyl when $R^2$ is methyl and R is isopropyl or tert-butyl.

41 Claims, No Drawings

SUBSTITUTED OXAZOLYL COMPOUNDS FOR THE TREATMENT OF INFLAMMATION

RELATED CASE

This application is a 371 of PCT/US94/05395 filed May 19, 1994 which is a continuation-in-part of Ser. No. 08/065,730, filed May 21, 1993, now U.S. Pat. No. 5,380,738.

FIELD OF THE INVENTION

This invention is in the field of anti-inflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). Recently, the sequence of another heretofore unknown enzyme in the human arachidonic acid/prostaglandin pathway has been reported by T. Hla and K. Nielson, *Proc. Natl. Acad. Sci, USA*, 89, 7384 (1992) and named "cyclooxygenase II (COX II)" or "prostaglandin G/H synthase II". The discovery of an inducible enzyme associated with inflammation provides a viable target of inhibition which more effectively reduces inflammation and produces fewer and less drastic side effects. Cyclooxygenase II is inducible by cytokines or endotoxins and such induction is inhibited by glucocortoids (J. Masferrer, et al, *Proc. Natl. Acad. Sci, USA*, 89, 3917 (1992)). The 6-methoxy-2-napthylacetic acid metabolite of nabumetone has been found by E. Meade et al to selectively inhibit the COX II enzyme (*J. Biol. Chem.*, 268, 6610 (1993)). In addition, Futaki et al (*Prostaglandins*, 47, 1 (1994)) have reported that N-(2-cyclohexyloxy-4-nitrophenyl)methanesulfonamide inhibits the COX II enzyme.

The references below that disclose antiinflammatory activity, show continuing efforts to find a safe and effective antiinflammatory agent. The novel oxazoles disclosed herein are such safe and also effective antiinflammatory agents furthering such efforts. The invention compounds are found to show usefulness in vivo as antiinflammatory agents with minimal side effects. The substituted oxazolyl compounds disclosed herein preferably selectively inhibit cyclooxygenase II over cyclooxygenase I.

2,3-Diaryl-5-halo thiophenes are described in U.S. Pat. No. 4,590,205 as analgesic or antiinflammatory agents. More particularly, 2,3-diaryl-5-bromo thiophenes are described in U.S. Pat. No. 4,820,827 as having antiinflammatory and prostaglandin synthetase inhibitory activity for use in the treatment of inflammation and dysmenorrhea. Copending application Ser. No. PCT/US94/466 describes 4,5-substitutedphenylthiophenes as having antiinflammatory activity.

Pyrazole derivatives having antiinflammatory activity are described in U.S. Pat. No. 5,134,142, to Matsuo et al.

U.S. Pat. No. 3,578,671, to K. Brown, describes antiinflammatory 4,5-diphenyloxazoles substituted in the 2-position by a saturated or unsaturated aliphatic acid. U.S. Pat. No. 4,051,250, to J. Dahm et al, describes oxazole, imidazole and thiazole compounds, including 2-mercapto-4-(4-methylmercaptophenyl)-5-(4-chlorophenyl)oxazole, as having antiphlogistic, analgesic and antipyretic activity. Other related diphenyloxazole disclosures include U.S. Pat. No. 4,001,228, to G. Mattalia, for antiaggregating activity and U.S. Pat. No. 3,895,024, to R. Hafeli, for intermediates in the production of antiinflammatory agents. U.S. Pat. No. 4,489,084, to F. Haviv and F. Kerdesky, describes diphenyloxazolyl hydrazinoalkyl nitrile compounds for use as antiinflammatory agents. U.S. Pat. No. 4,143,047, to R. Harrison, describes oxazole compounds as reactants to make 2-acylamino oxazole derivatives having anti-allergy activity.

U.S. Pat. No. 4,791,124, to Lutomski et al, describes the pesticide activity of substituted bis(4-halophenyl)oxazoles. U.S. Pat. No. 4,775,687, to Meguro et al describes the possible use of 4,5-phenyl oxazoles as starting materials for antidiabetic compounds. WO publication No. 517,591, published Dec. 9, 1992, describes bis(halophenyl)oxazole derivatives as starting materials for the preparation of anti-inflammatory agents.

N. Meanwell et al [*J. Med. Chem.*, 35, 3498 (1992)] describe bis(substitutedphenyl)oxazoles as having ADP-induced platelet aggregation inhibition activity.

U.S. Pat. No. 4,812,470, to N. Rogers et al, describes phenyl substituted oxazoles as having antibacterial activity.

U.S. Pat. No. 3,901,908, to K. Fitzi and R. Pfister, describes 2-alkyl and 2-cycloalkyl-4,5-phenyloxazoles as intermediates in the synthesis of imidazoles having analgesic and antipyretic activity. Specifically, 2-tert-butyl-4-(4-methylsulfonylphenyl)-5-phenyloxazole is described.

U.S. Pat. No. 4,632,930, to Carini et al, describes antihypertensive alkyl and aryl substituted imidazole, thiazole and oxazole derivatives. Specifically, 5-phenyl-4-(4-methylsulfonylphenyl)-α,α-bis(trifluoromethyl)thiazole-2-methanol is described.

R. Cremylin et al describe the synthesis of heterocyclic sulfonyl derivatives and specifically, 4',4"-(2-methyl-4,5-oxazoldiyl)-bis-benzenesulfonamide (*J. Heterocycl. Chem.*, 22, 1211 (1985)).

T. van Es and O. G. Backeberg [*J. Chem. Soc.*, 1363 (1963)] describe the synthesis of 2-methyl-4,5-substitutedphenyloxazoles; and specifically, 4-[5-(4-chlorophenyl)-2-methyl-4-oxazolyl]benzenesulfonamide.

DESCRIPTION OF THE INVENTION

A class of substituted oxazolyl compounds useful in treating inflammation-related disorders is defined by Formula I:

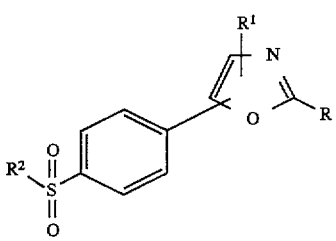

wherein R is selected from hydrido, alkyl, hydroxyalkyl, haloalkyl, alkenyl, hydroxyalkenyl, alkynyl, hydroxyalkynyl, cycloalkyl, cycloalkylalkyl, aryl optionally substituted at a substitutable position by carboxy, alkyl, alkoxy and halo, heteroaryl optionally substituted at a substitutable position by carboxy, alkyl, alkoxy and halo, aralkyl optionally substituted at a substitutable position on the aryl radical by carboxy, alkyl, alkoxy and halo, aryloxyalkyl optionally substituted at a substitutable position with halo, carboxy, alkyl and alkoxy, aralkoxyalkyl optionally substituted at a substitutable position with halo, carboxy, alkyl and alkoxy, heteroaryloxyalkyl optionally substituted at a substitutable position with halo, carboxy, alkyl and alkoxy, alkoxycarbonyl, alkoxycarbonylalkyl, carboxy, carboxyalkyl, arylthioalkyl, aminocarbonylalkyl, N-alkylaminocarbonylalkyl and N,N-dialkylaminocarbonylalkyl;

wherein $R^1$ is selected from cycloalkyl, cycloalkenyl, aryl and heteroaryl, wherein $R^1$ is optionally substituted at a substitutable position by alkyl, alkoxy and halo; and wherein $R^2$ is selected from alkyl, haloalkyl and amino;

or a pharmaceutically-acceptable salt thereof; provided R is not methyl when $R^2$ is amino; and further provided that $R^1$ is not phenyl when $R^2$ is methyl and R is isopropyl or tert-butyl.

The phrase "further provided", as used in the above description, is intended to mean that the denoted proviso is not to be considered conjunctive with the other provisos.

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of Formula I would be useful to treat arthritis, including but not limited to rheumatoid arthritis, spondyloarthopathies, gouty arthritis, osteoarthritis, systemic lupus erythematosus and juvenile arthritis. Such compounds of Formula I would be useful in the treatment of asthma, bronchitis, menstrual cramps, tendinitis, bursitis, and skin related conditions such as psoriasis, eczema, burns and dermatitis. Compounds of Formula I also would be useful to treat gastrointestinal conditions such as inflammatory bowel syndrome, Crohn's disease, gastritis, irritable bowel syndrome and ulcerative colitis and for the prevention of colorectal cancer. Compounds of Formula I would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds are useful as anti-inflammatory agents, such as for the treatment of arthritis, with the additional benefit of having significantly less harmful side effects.

Preferably, the compounds have a cyclooxygenase II $IC_{50}$ of less than about 0.1 µM, and also have a selectivity ratio of cyclooxygenase II inhibition over cyclooxygenase I inhibition of at least 50, and more preferably of at least 100. Even more preferably, the compounds have a cyclooxygenase I $IC_{50}$ of greater than about 0.5 µM, and more preferably of greater than 5 µM. Such preferred selectivity may indicate an ability to reduce the incidence of common NSAID-induced side effects.

A preferred class of compounds consists of those compounds of Formula I wherein R is selected from hydrido, lower alkyl, lower hydroxyalkyl, lower haloalkyl, lower alkenyl, lower hydroxyalkenyl, lower alkynyl, lower hydroxyalkynyl, lower cycloalkyl, lower cycloalkylalkyl, aryl selected from phenyl and naphthyl, optionally substituted at a substitutable position by halo, carboxy, lower alkyl and lower alkoxy, heteroaryl selected from pyridyl, thienyl, thiazolyl, oxazolyl, imidazolyl, furyl and quinolyl, optionally substituted at a substitutable position by halo, carboxy, lower alkyl and lower alkoxy, lower aralkyl optionally substituted at a substitutable position on the aryl radical by halo, carboxy, lower alkyl and lower alkoxy, lower aryloxyalkyl optionally substituted at a substitutable position with halo, carboxy, lower alkyl and lower alkoxy, lower heteroaryloxyalkyl optionally substituted at a substitutable position with halo, carboxy, lower alkyl and lower alkoxy, lower aralkoxyalkyl optionally substituted at a substitutable position with halo, carboxy, lower alkyl and lower alkoxy, carboxy, lower alkoxycarbonyl, lower alkoxycarbonylalkyl, lower carboxyalkyl, lower arylthioalkyl, lower aminocarbonylalkyl, lower N-alkylaminocarbonylalkyl and lower N,N-dialkylaminocarbonylalkyl;

wherein $R^1$ is selected from lower cycloalkyl, lower cycloalkenyl, phenyl, naphthyl and heteroaryl selected from pyridyl, thienyl, thiazolyl, oxazolyl, imidazolyl, furyl, quinolyl, 3,4-methylenedioxyphenyl, indolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by lower alkyl, lower alkoxy and halo; and wherein $R^2$ is selected from lower alkyl, lower haloalkyl and amino.

A class of compounds of particular interest consists of those compounds of Formula I wherein R is selected from hydrido, methyl, ethyl, n-propyl, isopropyl, butyl, tert-butyl, isobutyl, hydroxymethyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, ethenyl, 1-propenyl, 2-propenyl, 1-butenyl, 2-butenyl, 3-butenyl, hydroxyethenyl, ethynyl, 1-propynyl, 2-propynyl, 1-butynyl, 2-butynyl, 3-butynyl, hydroxyethynyl, cyclobutyl, cyclopentyl, cyclohexyl, cycloheptyl, cyclobutylmethyl, cyclopentylmethyl, cyclohexylmethyl, cyclohexylethyl, cyclohexylpropyl, cycloheptylmethyl, phenyl and naphthyl, optionally substituted at a substitutable position by fluoro, chloro, bromo, iodo, carboxy, methyl, ethyl, n-propyl, isopropyl, butyl, tert-butyl, isobutyl, methoxy, ethoxy, propoxy and butoxy, pyridyl, thienyl, thiazolyl, oxazolyl, imidazolyl, furyl and quinolyl, optionally substituted at a substitutable position by fluoro, chloro, bromo, iodo, carboxy, methyl, ethyl, n-propyl, isopropyl, butyl, tert-butyl, isobutyl, methoxy, ethoxy, propoxy and butoxy, benzyl, phenethyl, diphenylmethyl and phenpropyl, optionally substituted at a substitutable position on the phenyl radical by fluoro, chloro, bromo, iodo, carboxy, methyl, ethyl, n-propyl, isopropyl, butyl, tert-butyl, isobutyl, methoxy, ethoxy, propoxy and butoxy, phenoxymethyl optionally substituted at a substitutable position on the phenyl radical with fluoro, chloro, bromo, iodo, carboxy, methyl, ethyl, n-propyl, isopropyl, butyl, tert-butyl, isobutyl, methoxy, ethoxy, propoxy and butoxy, benzyloxymethyl optionally substituted at a substitutable position on the phenyl radical with fluoro, chloro, bromo, iodo, carboxy, methyl, ethyl, n-propyl, isopropyl, butyl, tert-butyl, isobutyl, methoxy, ethoxy, propoxy and butoxy, pyridyloxymethyl and quinolyloxymethyl optionally substituted at a substitutable position with fluoro, chloro, bromo, iodo, carboxy, methyl, ethyl, n-propyl, isopropyl, butyl, tert-butyl, isobutyl, methoxy, ethoxy, propoxy and butoxy, methoxycarbonyl, ethoxycarbonyl, propoxycarbonyl, butoxycarbonyl, methoxycarbonylmethyl, ethoxycarbonylmethyl, methoxycarbonylethyl, ethoxycarbonylethyl, carboxy, acetyl, propanoic, butanoic, pentanoic, hexanoic, phenylthiomethyl, aminocarbonylmethyl, N-methylaminocarbonylmethyl and N,N-dimethylaminocarbonylmethyl;

wherein $R^1$ is selected from cyclobutyl, cyclopentyl, cyclohexyl, cycloheptyl, 1-cyclohexenyl, 2-cyclohexenyl, 3-cyclohexenyl, cyclopentenyl, cycloheptenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by methyl, ethyl, n-propyl, isopropyl, butyl, tert-butyl, isobutyl, methoxy, ethoxy, propoxy, butoxy, fluoro, chloro, bromo and iodo; and wherein $R^2$ is selected from methyl, ethyl, trifluoromethyl, difluoromethyl, fluoromethyl and amino.

A family of specific compounds of particular interest within Formula I consists of compounds and pharmaceutically-acceptable salts thereof as follows:

4-[2-benzyl-5-(phenyl)oxazol-4-yl]benzenesulfonamide;
4-[2-benzyl-5-(2-fluorophenyl)oxazol-4-yl]benzenesulfonamide;
4-[2-benzyl-5-(3-fluorophenyl)oxazol-4-yl]benzenesulfonamide;
4-[2-benzyl-5-(4-fluorophenyl)oxazol-4-yl]benzenesulfonamide;
4-[2-benzyl-5-(2,4-difluorophenyl)oxazol-4-yl]benzenesulfonamide;
4-[2-benzyl-5-(2,5-difluorophenyl)oxazol-4-yl]benzenesulfonamide;
4-[2-benzyl-5-(2,6-difluorophenyl)oxazol-4-yl]benzenesulfonamide;
4-[2-benzyl-5-(3,4-difluorophenyl)oxazol-4-yl]benzenesulfonamide;
4-[2-benzyl-5-(3,5-difluorophenyl)oxazol-4-yl]benzenesulfonamide;
4-[2-benzyl-5-(2-chlorophenyl)oxazol-4-yl]benzenesulfonamide;
4-[2-benzyl-5-(3-chlorophenyl)oxazol-4-yl]benzenesulfonamide;
4-[2-benzyl-5-(4-chlorophenyl)oxazol-4-yl]benzenesulfonamide;
4-[2-benzyl-5-(2,4-dichlorophenyl)oxazol-4-yl]benzenesulfonamide;
4-[2-benzyl-5-(2,5-dichlorophenyl)oxazol-4-yl]benzenesulfonamide;
4-[2-benzyl-5-(2,6-dichlorophenyl)oxazol-4-yl]benzenesulfonamide;
4-[2-benzyl-5-(3,4-dichlorophenyl)oxazol-4-yl]benzenesulfonamide;
4-[2-benzyl-5-(3,5-dichlorophenyl)oxazol-4-yl]benzenesulfonamide;
4-[2-benzyl-5-(2-methoxyphenyl)oxazol-4-yl]benzenesulfonamide;
4-[2-benzyl-5-(3-methoxyphenyl)oxazol-4-yl]benzenesulfonamide;
4-[2-benzyl-5-(4-methoxyphenyl)oxazol-4-yl]benzenesulfonamide;
4-[2-benzyl-5-(2,4-dimethoxyphenyl)oxazol-4-yl]benzenesulfonamide;
4-[2-benzyl-5-(2,5-dimethoxyphenyl)oxazol-4-yl]benzenesulfonamide;
4-[2-benzyl-5-(2,6-dimethoxyphenyl)oxazol-4-yl]benzenesulfonamide;
4-[2-benzyl-5-(3,4-dimethoxyphenyl)oxazol-4-yl]benzenesulfonamide;
4-[2-benzyl-5-(3,5-dimethoxyphenyl)oxazol-4-yl]benzenesulfonamide;
4-[2-benzyl-5-(2-methylphenyl)oxazol-4-yl]benzenesulfonamide;
4-[2-benzyl-5-(3-methylphenyl)oxazol-4-yl]benzenesulfonamide;
4-[2-benzyl-5-(4-methylphenyl)oxazol-4-yl]benzenesulfonamide;
4-[2-benzyl-5-(2,4-dimethylphenyl)oxazol-4-yl]benzenesulfonamide;
4-[2-benzyl-5-(2,5-dimethylphenyl)oxazol-4-yl]benzenesulfonamide;
4-[2-benzyl-5-(2,6-dimethylphenyl)oxazol-4-yl]benzenesulfonamide;
4-[2-benzyl-5-(3,4-dimethylphenyl)oxazol-4-yl]benzenesulfonamide;
4-[2-benzyl-5-(3,5-dimethylphenyl)oxazol-4-yl]benzenesulfonamide;
4-[2-benzyl-5-(2-chloro-4-methylphenyl)oxazol-4-yl]benzenesulfonamide;
4-[2-benzyl-5-(3-chloro-4-methylphenyl)oxazol-4-yl]benzenesulfonamide;
4-[2-benzyl-5-(3-chloro-2-methylphenyl)oxazol-4-yl]benzenesulfonamide;
4-[2-benzyl-5-(2-chloro-6-methylphenyl)oxazol-4-yl]benzenesulfonamide;
4-[2-benzyl-5-(4-chloro-2-methylphenyl)oxazol-4-yl]benzenesulfonamide;
4-[2-benzyl-5-(4-chloro-3-methylphenyl)oxazol-4-yl]benzenesulfonamide;
4-[2-benzyl-5-(2-chloro-4-methoxyphenyl)oxazol-4-yl]benzenesulfonamide;
4-[2-benzyl-5-(3-chloro-4-methoxyphenyl)oxazol-4-yl]benzenesulfonamide;
4-[2-benzyl-5-(3-chloro-2-methoxyphenyl)oxazol-4-yl]benzenesulfonamide;
4-[2-benzyl -5-(2-chloro-6-methoxyphenyl)oxazol-4-yl]benzenesulfonamide;
4-[2-benzyl-5-(4-chloro-2-methoxyphenyl)oxazol-4-yl]benzenesulfonamide;
4-[2-benzyl-5-(4-chloro-3-methoxyphenyl)oxazol-4-yl]benzenesulfonamide;
4-[2-benzyl-5-(3,5-dichloro-4-methoxyphenyl)oxazol-4-yl]benzenesulfonamide;
4-[2-benzyl-5-(2-fluoro-4-methylphenyl)oxazol-4-yl]benzenesulfonamide;
4-[2-benzyl-5-(3-fluoro-4-methylphenyl)oxazol-4-yl]benzenesulfonamide;
4-[2-benzyl-5-(3-fluoro-2-methylphenyl)oxazol-4-yl]benzenesulfonamide;

4-[2-benzyl-5-(2-fluoro-6-methylphenyl)oxazol-4-yl]
benzenesulfonamide;
4-[2-benzyl-5-(4-fluoro-2-methylphenyl)oxazol-4-yl]
benzenesulfonamide;
4-[2-benzyl-5-(4-fluoro-3-methylphenyl)oxazol-4-yl]
benzenesulfonamide;
4-[2-benzyl-5-(2-fluoro-4-methoxyphenyl)oxazol-4-yl]
benzenesulfonamide;
4-[2-benzyl-5-(3-fluoro-4-methoxyphenyl)oxazol-4-yl]
benzenesulfonamide;
4-[2-benzyl-5-(3-fluoro-2-methoxyphenyl)oxazol-4-yl]
benzenesulfonamide;
4-[2-benzyl-5-(2-fluoro-6-methoxyphenyl)oxazol-4-yl]
benzenesulfonamide;
4-[2-benzyl-5-(4-fluoro-2-methoxyphenyl)oxazol-4-yl]
benzenesulfonamide;
4-[2-benzyl-5-(2-thienyl)oxazol-4-yl]benzenesulfonamide;
4-[2-benzyl-5-(5-chloro-2-thienyl)oxazol-4-yl]
benzenesulfonamide;
4-[2-benzyl-5-(cyclohexyl)oxazol-4-yl]
benzenesulfonamide;
4-[2-benzyl-5-(1-cyclohexenyl)oxazol-4-yl]
benzenesulfonamide;
4-[2-benzyl-5-(2-cyclohexenyl)oxazol-4-yl]
benzenesulfonamide;
4-[2-benzyl-5-(3-cyclohexenyl)oxazol-4-yl]
benzenesulfonamide;
2-benzyl-4-(4-methylsulfonylphenyl)-5-phenyloxazole;
2-benzyl-4-(4-methylsulfonylphenyl)-5-(2-fluorophenyl)
oxazole;
2-benzyl-4-(4-methylsulfonylphenyl)-5-(3-fluorophenyl)
oxazole;
2-benzyl-4-(4-methylsulfonylphenyl)-5-(2,4-difluorophenyl)oxazole;
2-benzyl-4-(4-methylsulfonylphenyl)-5-(2,5-difluorophenyl)oxazole;
2-benzyl-4-(4-methylsulfonylphenyl)-5-(2,6-difluorophenyl)oxazole;
2-benzyl-4-(4-methylsulfonylphenyl)-5-(3,4-difluorophenyl)oxazole;
2-benzyl-4-(4-methylsulfonylphenyl)-5-(3,5-difluorophenyl)oxazole;
2-benzyl-4-(4-methylsulfonylphenyl)-5-(2-chlorophenyl)
oxazole;
2-benzyl-4-(4-methylsulfonylphenyl)-5-(3-chlorophenyl)
oxazole;
2-benzyl-4-(4-methylsulfonylphenyl)-5-(4-chlorophenyl)
oxazole;
2-benzyl-4-(4-methylsulfonylphenyl)-5-(2,4-dichlorophenyl)oxazole;
2-benzyl-4-(4-methylsulfonylphenyl)-5-(2,5-dichlorophenyl)oxazole;
2-benzyl-4-(4-methylsulfonylphenyl)-5-(2,6-dichlorophenyl)oxazole;
2-benzyl-4-(4-methylsulfonylphenyl)-5-(3,4-dichlorophenyl)oxazole;
2-benzyl-4-(4-methylsulfonylphenyl)-5-(3,5-dichlorophenyl)oxazole;
2-benzyl-4-(4-methylsulfonylphenyl)-5-(2-methoxyphenyl)
oxazole;
2-benzyl-4-(4-methylsulfonylphenyl)-5-(3-methoxyphenyl)
oxazole;
2-benzyl-4-(4-methylsulfonylphenyl)-5-(4-methoxyphenyl)
oxazole;
2-benzyl-4-(4-methylsulfonylphenyl)-5-(2,4-dimethoxyphenyl)oxazole;
2-benzyl-4-(4-methylsulfonylphenyl-5-(2,5-dimethoxyphenyl)oxazole;
2-benzyl-4-(4-methylsulfonylphenyl)-5-(2,6-dimethoxyphenyl)oxazole;
2-benzyl-4-(4-methylsulfonylphenyl)-5-(3,4-dimethoxyphenyl)oxazole;
2-benzyl-4-(4-methylsulfonylphenyl)-5-3,5-dimethoxyphenyl)oxazole;
2-benzyl-4-(4-methylsulfonylphenyl)-5-2-methylphenyl)
oxazole;
2-benzyl-4-(4-methylsulfonylphenyl)-5-3-methylphenyl)
oxazole;
2-benzyl-4-(4-methylsulfonylphenyl)-5-(4-methylphenyl)
oxazole;
2-benzyl-4-(4-methylsulfonylphenyl)-5-(2,4-dimethylphenyl)oxazole;
2-benzyl-4-(4-methylsulfonylphenyl)-5-(2,5-dimethylphenyl)oxazole;
2-benzyl-4-(4-methylsulfonylphenyl)-5-(2,6-dimethylphenyl)oxazole;
2-benzyl-4-(4-methylsulfonylphenyl)-5-(3,4-dimethylphenyl)oxazole;
2-benzyl-4-(4-methylsulfonylphenyl)-5-(3,5-dimethylphenyl)oxazole;
2-benzyl-4-(4-methylsulfonylphenyl)-5-(2-chloro-4-methylphenyl)oxazole;
2-benzyl-4-(4-methylsulfonylphenyl)-5-(3-chloro-4-methylphenyl)oxazole;
2-benzyl-4-(4-methylsulfonylphenyl)-5-(3-chloro-2-methylphenyl)oxazole;
2-benzyl-4-(4-methylsulfonylphenyl)-5-(2-chloro-6-methylphenyl)oxazole;
2-benzyl-4-(4-methylsulfonylphenyl)-5-(4-chloro-2-methylphenyl)oxazole;
2-benzyl-4-(4-methylsulfonylphenyl)-5-(4-chloro-3-methylphenyl)oxazole;
2-benzyl-4-(4-methylsulfonylphenyl)-5-(2-chloro-4-methoxyphenyl)oxazole;
2-benzyl-4-(4-methylsulfonylphenyl)-5-(3-chloro-4-methoxyphenyl)oxazole;
2-benzyl-4-(4-methylsulfonylphenyl)-5-(3-chloro-2-methoxyphenyl)oxazole;
2-benzyl-4-(4-methylsulfonylphenyl)-5-(2-chloro-6-methoxyphenyl)oxazole;
2-benzyl-4-(4-methylsulfonylphenyl)-5-(4-chloro-2-methoxyphenyl)oxazole;
2-benzyl-4-(4-methylsulfonylphenyl)-5-(4-chloro-3-methoxyphenyl)oxazole;
2-benzyl-4-(4-methylsulfonylphenyl)-5-(3,5-dichloro-4-methoxyphenyl)oxazole;
2-benzyl-4-(4-methylsulfonylphenyl)-5-(2-fluoro-4-methylphenyl)oxazole;
2-benzyl-4-(4-methylsulfonylphenyl)-5-(3-fluoro-4-methylphenyl)oxazole;
2-benzyl-4-(4-methylsulfonylphenyl)-5-(3-fluoro-2-methylphenyl)oxazole;
2-benzyl-4-(4-methylsulfonylphenyl)-5-(2-fluoro-6-methylphenyl)oxazole;
2-benzyl-4-(4-methylsulfonylphenyl)-5-(4-fluoro-2-methylphenyl)oxazole;
2-benzyl-4-(4-methylsulfonylphenyl)-5-(4-fluoro-3-methylphenyl)oxazole;
2-benzyl-4-(4-methylsulfonylphenyl)-5-(2-fluoro-4-methoxyphenyl)oxazole;
2-benzyl-4-(4-methylsulfonylphenyl)-5-(3-fluoro-4-methoxyphenyl)oxazole;
2-benzyl-4-(4-methylsulfonylphenyl)-5-(3-fluoro-2-methoxyphenyl)oxazole;
2-benzyl-4-(4-methylsulfonylphenyl)-5-(2-fluoro-6-methoxyphenyl)oxazole;

2-benzyl-4-(4-methylsulfonylphenyl)-5-(4-fluoro-2-methoxyphenyl)oxazole;
2-benzyl-4-(4-methylsulfonylphenyl)-5-(2-thienyl)oxazole;
2-benzyl-4-(4-methylsulfonylphenyl)-5-(5-chloro-2-thienyl)oxazole;
2-benzyl -4-(4-methylsulfonylphenyl)-5-(cyclohexyl)oxazole-;
2-benzyl-4-(4-methylsulfonylphenyl)-5-(1-cyclohexenyl)oxazole;
2-benzyl-4-(4-methylsulfonylphenyl)-5-(2-cyclohexenyl)oxazole;
2-benzyl-4-(4-methylsulfonyl phenyl)-5-(3-cyclohexenyl)oxazole;
2-(ethyl)-4-(4-methylsulfonylphenyl)-5-phenyloxazole;
2-(trifluoromethyl)-4-(4-methylsulfonylphenyl)-5-phenyloxazole;
2-(difluoromethyl)-4-(4-methylsulfonylphenyl)-5-phenyloxazole;
2-(hydroxymethyl)-4-(4-methylsulfonylphenyl)-5-phenyloxazole;
2-(carboxy)-4-(4-methylsulfonylphenyl)-5-phenyloxazole;
2-(methoxycarbonyl)-4-(4-methylsulfonylphenyl)-5-phenyloxazole;
2-(ethoxycarbonyl)-4-(4-methylsulfonylphenyl)-5-phenyloxazole;
2-(propyl)-4-(4-methylsulfonylphenyl)-5-phenyloxazole;
2-(benzyl)-4-(4-methylsulfonylphenyl)-5-phenyloxazole;
2-(phenylthiomethyl)-4-(4-methylsulfonylphenyl)-5-phenyloxazole;
2-(phenoxymethyl)-4-(4-methylsulfonylphenyl)-5-phenyloxazole;
2-((4-chlorophenoxy)methyl)-4-(4-methylsulfonylphenyl)-5-phenyloxazole;
2-((3-chlorophenoxy)methyl)-4-(4-methylsulfonylphenyl)-5-phenyloxazole;
2-((2-chlorophenoxy)methyl)-4-(4-methylsulfonylphenyl)-5-phenyloxazole;
2-((4-fluorophenoxy)methyl)-4-(4-methylsulfonylphenyl-5-phenyloxazole;
2-((3-fluorophenoxy)methyl)-4-(4-methylsulfonylphenyl-5-phenyloxazole;
2-((2-fluorophenoxy)methyl)-4-(4-methylsulfonylphenyl)-5-phenyloxazole;
2-((4-carboxyphenoxy)methyl)-4-(4-methylsulfonylphenyl)-5-phenyloxazole;
2-((3-carboxyphenoxy)methyl)-4-(4-methylsulfonylphenyl)-5-phenyloxazole;
2-((2-carboxyphenoxy)methyl)-4-(4-methylsulfonylphenyl-5-phenyloxazole;
2-(2-phenethyl)-4-(4-methylsulfonylphenyl)-5-phenyloxazole;
2-(3-phenpropyl)-4-(4-methylsulfonylphenyl)-5-phenyloxazole;
2-(carboxymethyl)-4-(4-methylsulfonylphenyl)-5-phenyloxazole;
2-(ethoxycarbonylmethyl)-4-(4-methylsulfonylphenyl)-5-phenyloxazole;
2-(methoxycarbonylmethyl)-4-(4-methylsulfonylphenyl)-5-phenyloxazole;
2-(2-carboxyethyl)-4-(4-methylsulfonylphenyl)-5-phenyloxazole;
2-(2-methoxycarbonylethyl)-4-(4-methylsulfonylphenyl)-5-phenyloxazole;
2(2-ethoxycarbonylethyl)-4-(4-methylsulfonylphenyl)-5-phenyloxazole;
2-(3-carboxypropyl)-4-(4-methylsulfonylphenyl)-5-phenyloxazole;
2-(3-methoxycarbonylpropyl)-4-(4-methylsulfonylphenyl)-5-phenyloxazole;
2-(3-ethoxycarbonylpropyl)-4-(4-methylsulfonylphenyl)-5-phenyloxazole;
2-(2-quiniolyloxymethyl)-4-(4-methylsulfonylphenyl)-5-phenyloxazole;
4-[2-(ethyl)-5-phenyloxazol-4-yl]benzenesulfonamide;
4-[2-(trifluoromethyl)-5-phenyloxazol-4-yl]benzenesulfonamide;
4-[2-(difluoromethyl)-5-phenyloxazol-4-yl]benzenesulfonamide;
4-[2-(hydroxymethyl)-5-phenyloxazol-4-yl]benzenesulfonamide;
4-[2-(carboxy)-5-phenyloxazol-4-yl]benzenesulfonamide;
4-[2-(methoxycarbonyl)-5-phenyloxazol-4-yl]benzenesulfonamide;
4-[2-(ethoxycarbonyl)-5-phenyloxazol-4-yl]benzenesulfonamide;
4-[2-(propyl)-5-phenyloxazol-4-yl]benzenesulfonamide;
4-[2-(benzyl)-5-phenyloxazol-4-yl]benzenesulfonamide;
4-[2-(phenylthiomethyl)-5-phenyloxazol-4-yl]benzenesulfonamide;
4-[2-(phenoxymethyl)-5-phenyloxazol-4-yl]benzenesulfonamide;
4-[2-((4-chlorophenoxy)methyl)-5-phenyloxazol-4-yl]benzenesulfonamide;
4-[2-((3-chlorophenoxy)methyl)-5-phenyloxazol-4-yl]benzenesulfonamide;
4-[2-((2-chlorophenoxy)methyl)-5-phenyloxazol-4-yl]benzenesulfonamide;
4-[2-((4-fluorophenoxy)methyl)-5-phenyloxazol-4-yl]benzenesulfonamide;
4-[2-((3-fluorophenoxy)methyl)-5-phenyloxazol-4-yl]benzenesulfonamide;
4-[2-((2-fluorophenoxy)methyl)-5-phenyloxazol-4-yl]benzenesulfonamide;
4-[2-((4-carboxyphenoxy)methyl)-5-phenyloxazol-4-yl]benzenesulfonamide;
4-[2-((3-carboxyphenoxy)methyl)-5-phenyloxazol-4-yl]benzenesulfonamide;
4-[2-((2-carboxyphenoxy)methyl)-5-phenyloxazol-4-yl]benzenesulfonamide;
4-[2-(2-phenylethyl)-5-phenyloxazol-4-yl]benzenesulfonamide;
4-[2-(3-phenylpropyl)-5-phenyloxazol-4-yl]benzenesulfonamide;
4-[2-(carboxymethyl)-5-phenyloxazol-4-yl]benzenesulfonamide;
4-[2-(ethoxycarbonylmethyl)-5-phenyloxazol-4-yl]benzenesulfonamide;
4-[2-methoxycarbonylmethyl)-5-phenyloxazol-4-yl]benzenesulfonamide;
4-[2-(2-carboxyethyl)-5-phenyloxazol-4-yl]benzenesulfonamide;
4-[2-(2-methoxycarbonylethyl)-5-phenyloxazol-4-yl]benzenesulfonamide;
4-[2-(2-ethoxycarbonylethyl)-5-phenyloxazol-4-yl]benzenesulfonamide;
4-[2-(3-carboxypropyl)-5-phenyloxazol-4-yl]benzenesulfonamide;
4-[2-(3-methoxycarbonylpropyl)-5-phenyloxazol-4-yl]benzenesulfonamide;
4-[2-(3-ethoxycarbonylpropyl)-5-phenyloxazol-4-yl]benzenesulfonamide;
4-[2-(2-quiniolyloxymethyl)-5-phenyloxazol-4-yl]benzenesulfonamide;
4-[2-benzyl-4-phenyloxazol-5-yl]benzenesulfonamide;

4-[2-benzyl-4-(2-fluorophenyl)oxazol-5-yl]
benzenesulfonamide;
4-[2-benzyl-4-(3-fluorophenyl)oxazol-5-yl]
benzenesulfonamide;
4-[2-benzyl-4-(4-fluorophenyl)oxazol-5-yl]
benzenesulfonamide;
4-[2-benzyl-4-(2,4-difluorophenyl)oxazol-5-yl]
benzenesulfonamide;
4-[2-benzyl-4-(2,5-difluorophenyl)oxazol-5-yl]
benzenesulfonamide;
4-[2-benzyl-4-(2,6-difluorophenyl)oxazol-5-yl]
benzenesulfonamide;
4-[2-benzyl-4-(3,4-difluorophenyl)oxazol-5-yl]
benzenesulfonamide;
4-[2-benzyl-4-(3,5-difluorophenyl)oxazol-5-yl]
benzenesulfonamide;
4-[2-benzyl-4-(2-chlorophenyl)oxazol-5-yl]
benzenesulfonamide;
4-[2-benzyl-4-(3-chlorophenyl)oxazol-5-yl]
benzenesulfonamide;
4-[2-benzyl-4-(4-chlorophenyl)oxazol-5-yl]
benzenesulfonamide;
4-[2-benzyl-4-(2,4-dichlorophenyl)oxazol-5-yl]
benzenesulfonamide;
4-[2-benzyl-4-(2,5-dichlorophenyl)oxazol-5-yl]
benzenesulfonamide;
4-[2-benzyl-4-(2,6-dichlorophenyl)oxazol-5-yl]
benzenesulfonamide;
4-[2-benzyl-4-(3,4-dichlorophenyl)oxazol-5-yl]
benzenesulfonamide;
4-[2-benzyl-4-(3,5-dichlorophenyl)oxazol-5-yl]
benzenesulfonamide;
4-[2-benzyl-4-(2-methoxyphenyl)oxazol-5-yl]
benzenesulfonamide;
4-[2-benzyl-4-(3-methoxyphenyl)oxazol-5-yl]
benzenesulfonamide;
4-[2-benzyl-4-(4-methoxyphenyl)oxazol-5-yl]
benzenesulfonamide;
4-[2-benzyl-4-(2,4-dimethoxyphenyl)oxazol-5-yl]
benzenesulfonamide;
4-[2-benzyl-4-(2,5-dimethoxyphenyl)oxazol-5-yl]
benzenesulfonamide;
4-[2-benzyl-4-(2,6-dimethoxyphenyl)oxazol-5-yl]
benzenesulfonamide;
4-[2-benzyl-4-(3,4-dimethoxyphenyl)oxazol-5-yl]
benzenesulfonamide;
4-[2-benzyl-4-(3,5-dimethoxyphenyl)oxazol-5-yl]
benzenesulfonamide;
4-[2-benzyl-4-(2-methylphenyl)oxazol-5-yl]
benzenesulfonamide;
4-[2-benzyl-4-(3-methylphenyl)oxazol-5-yl]
benzenesulfonamide;
4-[2-benzyl-4-(4-methylphenyl)oxazol-5-yl]
benzenesulfonamide;
4-[2-benzyl-4-(2,4-dimethylphenyl)oxazol-5-yl]
benzenesulfonamide;
4-[2-benzyl-4-(2,5-dimethylphenyl)oxazol-5-yl]
benzenesulfonamide;
4-[2-benzyl-4-(2,6-dimethylphenyl)oxazol-5-yl]
benzenesulfonamide;
4-[2-benzyl-4-(3,4-dimethylphenyl)oxazol-5-yl]
benzenesulfonamide;
4-[2-benzyl-4-(3,5-dimethylphenyl)oxazol-5-yl]
benzenesulfonamide;
4-[2-benzyl-4-(2-chloro-4-methylphenyl)oxazol-5-yl]
benzenesulfonamide;
4-[2-benzyl-4-(3-chloro-4-methylphenyl)oxazol-5-yl]
benzenesulfonamide;
4-[2-benzyl-4-(3-chloro-2-methylphenyl)oxazol-5-yl]
benzenesulfonamide;
4-[2-benzyl-4-(2-chloro-6-methylphenyl)oxazol-5-yl]
benzenesulfonamide;
4-[2-benzyl-4-(4-chloro-2-methylphenyl)oxazol-5-yl]
benzenesulfonamide;
4-[2-benzyl-4-(4-chloro-3-methylphenyl)oxazol-5-yl]
benzenesulfonamide;
4-[2-benzyl-4-(2-chloro-4-methoxyphenyl)oxazol-5-yl]
benzenesulfonamide;
4-[2-benzyl-4-(3-chloro-4-methoxyphenyl)oxazol-5-yl]
benzenesulfonamide;
4-[2-benzyl-4-(3-chloro-2-methoxyphenyl)oxazol-5-yl]
benzenesulfonamide;
4-[2-benzyl-4-(2-chloro-6-methoxyphenyl)oxazol-5-yl]
benzenesulfonamide;
4-[2-benzyl-4-(4-chloro-2-methoxyphenyl)oxazol-5-yl]
benzenesulfonamide;
4-[2-benzyl-4-(4-chloro-3-methoxyphenyl)oxazol-5-yl]
benzenesulfonamide;
4-[2-benzyl-4-(3,5-dichloro-4-methoxyphenyl)oxazol-5-yl]
benzenesulfonamide;
4-[2-benzyl-4-(2-fluoro-4-methylphenyl)oxazol-5-yl]
benzenesulfonamide;
4-[2-benzyl-4-(3-fluoro-4-methylphenyl)oxazol-5-yl]
benzenesulfonamide;
4-[2-benzyl-4-(3-fluoro-2-methylphenyl)oxazol-5-yl]
benzenesulfonamide;
4-[2-benzyl-4-(2-fluoro-6-methylphenyl)oxazol-5-yl]
benzenesulfonamide;
4-[2-benzyl-4-(4-fluoro-2-methylphenyl)oxazol-5-yl]
benzenesulfonamide;
4-[2-benzyl-4-(4-fluoro-3-methylphenyl)oxazol-5-yl]
benzenesulfonamide;
4-[2-benzyl-4-(2-fluoro-4-methoxyphenyl)oxazol-5-yl]
benzenesulfonamide;
4-[2-benzyl-4-(3-fluoro-4-methoxyphenyl)oxazol-5 -yl]
benzenesulfonamide;
4-[2-benzyl-4-(3-fluoro-2-methoxyphenyl)oxazol-5-yl]
benzenesulfonamide;
4-[2-benzyl-4-(2-fluoro-6-methoxyphenyl)oxazol-5-yl]
benzenesulfonamide;
4-[2-benzyl-4-(4-fluoro-2-methoxyphenyl)oxazol-5-yl]
benzenesulfonamide;
4-[2-benzyl-4-(2-thienyl)oxazol-5-yl]benzenesulfonamide;
4-[2-benzyl-4-(5-chloro-2-thienyl)oxazol-5-yl]
benzenesulfonamide;
4-[2-benzyl-4-(cyclohexyl)oxazol-5-yl]
benzenesulfonamide;
4-[2-benzyl-4-(1-cyclohexenyl)oxazol-5-yl]
benzenesulfonamide;
4-[2-benzyl-4-(2-cyclohexenyl)oxazol-5-yl]
benzenesulfonamide;
4-[2-benzyl-4-(3-cyclohexenyl)oxazol-5-yl]
benzenesulfonamide;
2-benzyl-5-(4-methylsulfonylphenyl)-4-phenyloxazole;
2-benzyl-5-(4-methylsulfonylphenyl)-4-(2-fluorophenyl)
oxazole;
2-benzyl-5-(4-methylsulfonylphenyl)-4-(3-fluorophenyl)
oxazole;
2-benzyl-5-(4-methylsulfonylphenyl)-4-(2,4-difluorophenyl)oxazole;
2-benzyl-5-(4-methylsulfonylphenyl)-4-(2,5-difluorophenyl)oxazole;
2-benzyl-5-(4-methylsulfonylphenyl)-4-(2,6-difluorophenyl)oxazole;
2-benzyl-5-(4-methylsulfonylphenyl)-4-(3,4-difluorophenyl)oxazole;

2-benzyl-5-(4-methylsulfonylphenyl)-4-(3,5-difluorophenyl)oxazole;
2-benzyl-5-(4-methylsulfonylphenyl)-4-(2-chlorophenyl)oxazol-4-yl]benzenesulfonamide;
2-benzyl-5-(4-methylsulfonylphenyl)-4-(3-chlorophenyl)oxazole;
2-benzyl-5-(4-methylsulfonylphenyl)-4-(4-chlorophenyl)oxazol-4-yl]benzenesulfonamide;
2-benzyl-5-(4-methylsulfonylphenyl)-4-(2,4-dichlorophenyl)oxazole;
2-benzyl-5-(4-methylsulfonylphenyl)-4-(2,5-dichlorophenyl)oxazole;
2-benzyl-5-(4-methylsulfonylphenyl)-4-(2,6-dichlorophenyl)oxazole;
2-benzyl-5-(4-methylsulfonylphenyl)-4-(3,4-dichlorophenyl)oxazole;
2-benzyl-5-(4-methylsulfonylphenyl)-4-(3,5-dichlorophenyl)oxazole;
2-benzyl-5-(4-methylsulfonylphenyl)-4-(2-methoxyphenyl)oxazole;
2-benzyl-5-(4-methylsulfonylphenyl)-4-(3-methoxyphenyl)oxazole;
2-benzyl-5-(4-methylsulfonylphenyl)-4-(4-methoxyphenyl)oxazole;
2-benzyl-5-(4-methylsulfonylphenyl)-4-(2,4-dimethoxyphenyl)oxazole;
2-benzyl-5-(4-methylsulfonylphenyl)-4-(2,5-dimethoxyphenyl)oxazole;
2-benzyl-5-(4-methylsulfonylphenyl)-4-(2,6-dimethoxyphenyl)oxazole;
2-benzyl-5-(4-methylsulfonylphenyl)-4-(3,4-dimethoxyphenyl)oxazole;
2-benzyl-5-(4-methylsulfonylphenyl)-4-(3,5-dimethoxyphenyl)oxazole;
2-benzyl-5-(4-methylsulfonylphenyl)-4-(2-methylphenyl)oxazole;
2-benzyl-5-(4-methylsulfonylphenyl)-4-(3-methylphenyl)oxazole;
2-benzyl-5-(4-methylsulfonylphenyl)-4-(4-methylphenyl)oxazole;
2-benzyl-5-(4-methylsulfonylphenyl)-4-(2,4-dimethylphenyl)oxazole;
2-benzyl-5-(4-methylsulfonylphenyl)-4-(2,5-dimethylphenyl)oxazole;
2-benzyl-5-(4-methylsulfonylphenyl)-4-(2,6-dimethylphenyl)oxazole;
2-benzyl-5-(4-methylsulfonylphenyl)-4-(3,4-dimethylphenyl)oxazole;
2-benzyl-5-(4-methylsulfonylphenyl)-4-(3,5-dimethylphenyl)oxazole;
2-benzyl-5-(4-methylsulfonylphenyl)-4-(2-chloro-4-methylphenyl)oxazole;
2-benzyl-5-(4-methylsulfonylphenyl)-4-(3-chloro-4-methylphenyl)oxazole;
2-benzyl-5-(4-methylsulfonylphenyl)-4-(3-chloro-2-methylphenyl)oxazole;
2-benzyl-5-(4-methylsulfonylphenyl)-4-(2-chloro-6-methylphenyl)oxazole;
2-benzyl-5-(4-methylsulfonylphenyl)-4-(4-chloro-2-methylphenyl)oxazole;
2-benzyl-5-(4-methylsulfonylphenyl)-4-(4-chloro-3-methylphenyl)oxazole;
2-benzyl-5-(4-methylsulfonylphenyl)-4-(2-chloro-4-methoxyphenyl)oxazole;
2-benzyl-5-(4-methylsulfonylphenyl)-4-(3-chloro-4-methoxyphenyl)oxazole;
2-benzyl-5-(4-methylsulfonylphenyl)-4-(3-chloro-2-methoxyphenyl)oxazole;
2-benzyl-5-(4-methylsulfonylphenyl)-4-(2-chloro-6-methoxyphenyl)oxazole;
2-benzyl-5-(4-methylsulfonylphenyl)-4-(4-chloro-2-methoxyphenyl)oxazole;
2-benzyl-5-(4-methylsulfonylphenyl)-4-(4-chloro-3-methoxyphenyl)oxazole;
2-benzyl-5-(4-methylsulfonylphenyl)-4-(3,5-dichloro-4-methoxyphenyl)oxazole;
2-benzyl-5-(4-methylsulfonylphenyl)-4-(2-fluoro-4-methylphenyl)oxazole;
2-benzyl-5-(4-methylsulfonylphenyl)-4-(3-fluoro-4-methylphenyl)oxazole;
2-benzyl-5-(4-methylsulfonylphenyl)-4-(3-fluoro-2-methylphenyl)oxazole;
2-benzyl-5-(4-methylsulfonylphenyl)-4-(2-fluoro-6-methylphenyl)oxazole;
2-benzyl-5-(4-methylsulfonylphenyl)-4-(4-fluoro-2-methylphenyl)oxazole;
2-benzyl-5-(4-methylsulfonylphenyl)-4-(4-fluoro-3-methylphenyl)oxazole;
2-benzyl-5-(4-methylsulfonylphenyl)-4-(2-fluoro-4-methoxyphenyl)oxazole;
2-benzyl-5-(4-methylsulfonylphenyl)-4-(3-fluoro-4-methoxyphenyl)oxazole;
2-benzyl-5-(4-methylsulfonylphenyl)-4-(3-fluoro-2-methoxyphenyl)oxazole;
2-benzyl-5-(4-methylsulfonylphenyl)-4-(2-fluoro-6-methoxyphenyl)oxazole;
2-benzyl-5-(4-methylsulfonylphenyl)-4-(4-fluoro-2-methoxyphenyl)oxazole;
2-benzyl-5-(4-methylsulfonylphenyl)-4-(2-thienyl)oxazole;
2-benzyl-5-(4-methylsulfonylphenyl)-4-(5-chloro-2-thienyl)oxazole;
2-benzyl-5-(4-methylsulfonylphenyl)-4-(cyclohexyl)oxazole-;
2-benzyl-5-(4-methylsulfonylphenyl)-4-(1-cyclohexenyl)oxazole;
2-benzyl-5-(4-methylsulfonylphenyl)-4-(2-cyclohexenyl)oxazole;
2-benzyl-5-(4-methylsulfonylphenyl)-4-3-cyclohexenyl)oxazole;
2-(ethyl)-5-(4-methylsulfonylphenyl)-4-phenyloxazole;
2-(trifluoromethyl)-5-(4-methylsulfonylphenyl)-4-phenyloxazole; -
2-(difluoromethyl)-5-(4-methylsulfonylphenyl)-4-phenyloxazole;
2-(hydroxymethyl)-5-(4-methylsulfonylphenyl)-4-phenyloxazole;
2-(carboxy)-5-(4-methylsulfonylphenyl)-4-phenyloxazole;
2-(methoxycarbonyl)-5-(4-methylsulfonylphenyl)-4-phenyloxazole;
2-(ethoxycarbonyl)-5-(4-methylsulfonylphenyl)-4-phenyloxazole;
2-(propyl)-5-(4-methylsulfonylphenyl)-4-phenyloxazole;
2-(benzyl)-5-(4-methylsulfonylphenyl)-4-phenyloxazole;
2-(phenylthiomethyl)-5-(4-methylsulfonylphenyl)-4-phenyloxazole;
2-(phenoxymethyl)-5-(4-methylsulfonylphenyl)-4-phenyloxazole;
2-((4-chlorophenoxy)methyl)-5-(4-methylsulfonylphenyl)-4-phenyloxazole;
2-((3-chlorophenoxy)methyl)-5-(4-methylsulfonylphenyl)-4-phenyloxazole;
2-((2-chlorophenoxy)methyl)-5-(4-methylsulfonylphenyl)-4-phenyloxazole;
2-((4-fluorophenoxy)methyl)-5-(4-methylsulfonylphenyl)-4-phenyloxazole;

2-((3-fluorophenoxy)methyl)-5-(4-methylsulfonylphenyl)-4-phenyloxazole;
2-((2-fluorophenoxy)methyl)-5-(4-methylsulfonylphenyl)-4-phenyloxazole;
2-((4-carboxyphenoxy)methyl)-5-(4-methylsulfonylphenyl)-4-phenyloxazole;
2-((3-carboxyphenoxy)methyl)-5-(4-methylsulfonylphenyl)-4-phenyloxazole;
2-((2-carboxyphenoxy)methyl)-5-(4-methylsulfonylphenyl)-4-phenyloxazole;
2-(2-phenethyl)-5-(4-methylsulfonylphenyl)-4-phenyloxazole;
2-(3-phenpropyl)-5-(4-methylsulfonylphenyl)-4-phenyloxazole;
2-(carboxymethyl)-5-(4-methylsulfonylphenyl)-4-phenyloxazole;
2-(ethoxycarbonylmethyl)-5-(4-methylsulfonylphenyl)-4-phenyloxazole;
2-(methoxycarbonylmethyl)-5-(4-methylsulfonylphenyl)-4-phenyloxazole;
2-(2-carboxyethyl)-5-(4-methylsulfonylphenyl)-4-phenyloxazole;
2-(2-methoxycarbonylethyl)-5-(4-methylsulfonylphenyl)-4-phenyloxazole;
2-(2-ethoxycarbonylethyl)-5-(4-methylsulfonylphenyl)-4-phenyloxazole;
2-(3-carboxypropyl)-5-(4-methylsulfonylphenyl)-4-phenyloxazole;
2-(3-methoxycarbonylpropyl)-5-(4-methylsulfonylphenyl)-4-phenyloxazole;
2-(3-ethoxycarbonylpropyl)-5-(4-methylsulfonylphenyl)-4-phenyloxazole;
2-(2-quiniolyloxymethyl)-5-(4-methylsulfonylphenyl)-4-phenyloxazole;
4-[2-(ethyl)-4-phenyloxazol-5-yl]benzenesulfonamide;
4-[2-(trifluoromethyl)-4-phenyloxazol-5-yl]benzenesulfonamide;
4-[2-(difluoromethyl)-4-phenyloxazol-5-yl]benzenesulfonamide;
4-[2-(hydroxymethyl)-4-phenyloxazol-5-yl]benzenesulfonamide;
4-[2-(carboxy)-4-phenyloxazol-5-yl]benzenesulfonamide;
4-[2-(methoxycarbonyl)-4-phenyloxazol-5-yl]benzenesulfonamide;
4-[2-(ethoxycarbonyl)-4-phenyloxazol-5-yl]benzenesulfonamide;
4-[2-(propyl)-4-phenyloxazol-5-yl]benzenesulfonamide;
4-[2-(benzyl)-4-phenyloxazol-5-yl]benzenesulfonamide;
4-[2-(phenylthiomethyl)-4-phenyloxazol-5-yl]benzenesulfonamide;
4-[2-(phenoxymethyl)-4-phenyloxazol-5-yl]benzenesulfonamide;
4-[2-((4-chlorophenoxy)methyl)-4-phenyloxazol-5-yl]benzenesulfonamide;
4-[2-((3-chlorophenoxy)methyl)-4-phenyloxazol-5-yl]benzenesulfonamide;
4-[2-((2-chlorophenoxy)methyl)-4-phenyloxazol-5-yl]benzenesulfonamide;
4-[2-((4-fluorophenoxy)methyl)-4-phenyloxazol-5-yl]benzenesulfonamide;
4-[2-((3-fluorophenoxy)methyl)-4-phenyloxazol-5-yl]benzenesulfonamide;
4-[2-((2-fluorophenoxy)methyl)-4-phenyloxazol-5-yl]benzenesulfonamide;
4-[2-((4-carboxyphenoxy)methyl)-4-phenyloxazol-5-yl]benzenesulfonamide;
4-[2-((3-carboxyphenoxy)methyl)-4-phenyloxazol-5-yl]benzenesulfonamide;
4-[2-((2-carboxyphenoxy)methyl)-4-phenyloxazol-5-yl]benzenesulfonamide;
4-[2-(2-phenethyl)-4-phenyloxazol-5-yl]benzenesulfonamide;
4-[2-(3-phenpropyl)-4-phenyloxazol-5-yl]benzenesulfonamide;
4-[2-(carboxymethyl)-4-phenyloxazol-5-yl]benzenesulfonamide;
4-[2-(ethoxycarbonylmethyl)-4-phenyloxazol-5-yl]benzenesulfonamide;
4-[2-(methoxycarbonylmethyl)-4-phenyloxazol-5-yl]benzenesulfonamide;
4-[2-(2-carboxyethyl)-4-phenyloxazol-5-yl]benzenesulfonamide;
4-[2-(2-methoxycarbonylethyl)-4-phenyloxazol-5-yl]benzenesulfonamide;
4-[2-(2-ethoxycarbonylethyl)-4-phenyloxazol-5-yl]benzenesulfonamide;
4-[(3-carboxypropyl)-4-phenyloxazol-5-yl]benzenesulfonamide;
4-[2-(3-methoxycarbonylpropyl)-4-phenyloxazol-5-yl]benzenesulfonamide;
4-[2-(3-ethoxycarbonylpropyl)-4-phenyloxazol-5-yl]benzenesulfonamide;
4-[2-(2-quiniolyloxymethyl)-4-phenyloxazol-5-yl]benzenesulfonamide;
5-[(4-fluorophenyl)-2-methyl-4-[(methylsulfonyl)phenyl]oxazole;
3-[5-(4-fluorophenyl)-4-[4-(methylsulfonyl)phenyl]oxazol-2-yl]propanoic acid;
methyl 3-[5-(4-fluorophenyl)-4-[4-(methylsulfonyl)phenyl]oxazol-2-yl]propanate;
4-(4-fluorophenyl)-2-(2-phenylethyl)-5-(4-(methylsulfonyl)phenyl)oxazole;
4-(4-fluorophenyl)-2-methyl-5-[4-(methylsulfonyl)phenyl]oxazole;
4-(4-fluorophenyl)-5-[4-(methylsulfonyl)phenyl]-2-phenyloxazole;
2-benzyl-4-(4-fluorophenyl)-5-(4-(methylsulfonyl)phenyl)oxazole;
4-(4-fluorophenyl)-5-[4-methylsulfonylphenyl]-2-(3-phenylpropyl)oxazole;
4-fluorophenyl)-5-[4-methylsulfonylphenyl]-2-propyloxazole;
2-(tert-butyl)-4-(4-fluorophenyl)-5-[4-methylsulfonylphenyl]oxazole;
4-(4-fluorophenyl)-2-[(4-methoxyphenyl)methyl]-5-[4-methylsulfonylphenyl]oxazole
4-(4-fluorophenyl)-2-[(3-methoxyphenyl)methyl]-5-[4-methylsulfonylphenyl]oxazole;
2-(diphenylmethyl)-4-(4-fluorophenyl)-5-[4-methylsulfonylphenyl]oxazole;
2-[4-(4-fluorophenyl)-5-[4-methylsulfonylphenyl]oxazol-2-yl]acetic acid;
ethyl 2-[4-(4-fluorophenyl)-5-[4-methylsulfonylphenyl]oxazol-2-yl]acetate;
3-[4-(4-fluorophenyl)-5-[4-methylsulfonylphenyl]oxazol-2-yl]propanoic acid;
methyl 3-[4-(4-fluorophenyl)-5-[4-methylsulfonylphenyl]oxazol-2-yl]propanate;
4-[4-(4-fluorophenyl)-5-[4-methylsulfonylphenyl]oxazol-2-yl]butanoic acid;
methyl 4-[4-(4-fluorophenyl)-5-[4-methylsulfonyl phenyl]oxazol-2-yl]butanate;
3-[4-(4-fluorophenyl)-5-[4-methylsulfonyl phenyl]oxazol-2-yl]propanamide;
ethyl 2-[4-(4-fluorophenyl)-5-[4-(methylsulfonyl)phenyl]oxazol-2-yl]-2-benzyl-acetate;

4-(4-fluorophenyl)-2-(cyclohexylethyl)-5-[4-(methylsulfonyl)phenyl]oxazole;

4-(4-fluorophenyl)-2-(3-fluorophenoxymethyl)-5-[4-(methylsulfonyl)phenyl]oxazole;

4-(4-fluorophenyl)-2-(3-chlorophenoxymethyl)-5-[4-(methylsulfonyl)phenyl]oxazole;

4-(4-fluorophenyl)-2-(pyridyloxymethyl)-5-[4-(methylsulfonyl)phenyl]oxazole;

4-(4-fluorophenyl)-5-[4-(methylsulfonyl)phenyl]-2-phenoxymethyloxazole;

4-(4-fluorophenyl)-2-(2-hydroxyethyl)-5-[4-(methylsulfonyl)phenyl]oxazole;

4-(4-fluorophenyl)-2-(hydroxymethyl)-5-[4-(methylsulfonyl)phenyl]oxazole;

4-(4-cyclohexyl)-2-phenyl-5-[4-(methylsulfonyl)phenyl] oxazole;

4-(4-fluorophenyl)-2-benzyloxymethyl-5-[4-(methylsulfonyl)phenyl]oxazole;

4-(4-fluorophenyl)-2-cyclohexyl-5-[4-(methylsulfonyl) phenyl]oxazole; and 5-(4-fluorophenyl)-2-phenyl-4-[4-(methylsulfonyl)phenyl] oxazole.

Within Formula I there is a subclass of compounds of high interest wherein R is selected from alkyl, hydroxyalkyl, haloalkyl, cycloalkyl, cycloalkylalkyl, aryl optionally substituted at a substitutable position by carboxy, alkyl, alkoxy and halo, aralkyl optionally substituted at a substitutable position on the aryl radical by carboxy, alkyl, alkoxy and halo, aryloxyalkyl optionally substituted at a substitutable position on the aryl radical with halo, carboxy, alkyl and alkoxy, aralkoxyalkyl optionally substituted at a substitutable position by alkyl, carboxy, alkoxy and halo, heteroaryloxyalkyl optionally substituted at a substitutable position on the heteroaryl radical with halo, carboxy, alkyl and alkoxy, alkoxycarbonylalkyl, carboxyalkyl and aminocarbonylalkyl; wherein $R^1$ is selected from cycloalkyl, cycloalkenyl, heteroaryl and aryl optionally substituted at a substitutable position by alkyl, alkoxy and halo, and wherein $R^2$ is methyl; or a pharmaceutically-acceptable salt thereof; provided $R^1$ is not phenyl when R is isopropyl or tert-butyl.

A more preferred class of compounds of the first subclass wherein R is selected from lower alkyl, lower hydroxyalkyl, lower haloalkyl, lower cycloalkyl, lower cycloalkylalkyl, aryl selected from phenyl and naphthyl, optionally substituted at a substitutable position by halo, carboxy, lower alkyl and lower alkoxy, lower aralkyl optionally substituted at a substitutable position on the aryl radical by halo, carboxy, lower alkyl and lower alkoxy, lower aryloxyalkyl optionally substituted at a substitutable position on the aryl radical with halo, carboxy, lower alkyl and lower alkoxy, aralkoxyalkyl optionally substituted at a substitutable position by halo, carboxy, lower alkyl and lower alkoxy, lower heteroaryloxyalkyl optionally substituted at a substitutable position with halo, carboxy, lower alkyl and lower alkoxy, lower alkoxycarbonylalkyl, lower carboxyalkyl and lower aminocarbonylalkyl; and wherein $R^1$ is selected from lower cycloalkyl, lower cycloalkenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by lower alkyl, lower alkoxy and halo; or a pharmaceutically-acceptable salt or prodrug thereof.

A class of compounds of particular interest consists of those compounds of the first subclass wherein R is selected from methyl, ethyl, n-propyl, isopropyl, butyl, tert-butyl, isobutyl, hydroxymethyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyclobutyl, cyclopentyl, cyclohexyl, cycloheptyl, cyclobutylmethyl, cyclopentylmethyl, cyclohexylmethyl, cyclohexylethyl, cyclohexylpropyl, cycloheptylmethyl, aryl selected from phenyl and naphthyl, optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, benzyl, phenethyl, diphenylmethyl and phenpropyl, optionally substituted at a substitutable position on the phenyl radical by fluoro, chloro, bromo, iodo, methyl, ethyl, n-propyl, isopropyl, butyl, tert-butyl, isobutyl, carboxy, methoxy, ethoxy, propoxy and butoxy, phenoxymethyl optionally substituted at a substitutable position with fluoro, chloro, bromo, iodo, methyl, ethyl, n-propyl, isopropyl, butyl, tert-butyl, isobutyl, carboxy, methoxy, ethoxy, propoxy and butoxy, benzyloxymethyl optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, pyridyloxymethyl and quinolyloxymethyl, optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, methoxycarbonylmethyl, ethoxycarbonylmethyl, methoxycarbonylethyl, ethoxycarbonylethyl, acetyl, propanoic, butanoic, pentanoic, hexanoic and aminocarbonylethyl; and wherein $R^1$ is selected from cyclobutyl, cyclopentyl, cyclohexyl, cycloheptyl, 1-cyclohexenyl, 2-cyclohexenyl, 3-cyclohexenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by methyl, ethyl, n-propyl, isopropyl, butyl, tert-butyl, isobutyl, methoxy, ethoxy, propoxy, butoxy, fluoro, chloro, bromo and iodo.

A family of specific compounds of particular interest within the first subclass consists of compounds and pharmaceutically-acceptable salts thereof as follows:

5-(4-fluorophenyl)-2-methyl-4-[4-(methylsulfonyl) phenyl] oxazole;

3-[5-(4-fluorophenyl)-4-[4-(methylsulfonyl)phenyl]-2-oxazol-2-yl]propanoic acid;

methyl 3-[5-(4-fluorophenyl)-4-[4-(methylsulfonyl) phenyl]-2-oxazol-2-yl]propanate;

4-(4-fluorophenyl)-2-(2-phenylethyl)-5-(4-(methylsulfonyl) phenyl)oxazole;

4-(4-fluorophenyl)-2-methyl-5-[4-methylsulfonylphenyl] oxazole;

4-(4-fluorophenyl)-5-[4-(methylsulfonyl)phenyl]-2-phenyloxazole;

2-benzyl-4-(4-fluorophenyl)-5-(4-methylsulfonyl)phenyl) oxazole;

4-(4-fluorophenyl)-5-[4-methylsulfonylphenyl]-2-(3-phenylpropyl)oxazole;

4-(4-fluorophenyl)-5-[4-methylsulfonylphenyl]-2-propyloxazole;

2-(tert-butyl)-4-(4-fluorophenyl)-5-[4-methylsulfonylphenyl]oxazole;

4-(4-fluorophenyl)-2-[(4-methoxyphenyl)methyl]-5-[4-methylsulfonylphenyl]oxazole 4-(4-fluorophenyl)-2-[(3-methoxyphenyl)methyl]-5-[4-methylsulfonylphenyl]oxazole;

2-(diphenylmethyl)-4-(4-fluorophenyl)-5-[4-methylsulfonylphenyl]oxazole;

2-[4-(4-fluorophenyl)-5-[4-methylsulfonylphenyl]oxazol-2-yl]acetic acid;

ethyl 2-[4-(4-fluorophenyl)-5-[4-methylsulfonylphenyl]oxazol-2-yl]acetate;

3-[4-(4-fluorophenyl)-5-[4-methylsulfonylphenyl]oxazol-2-yl]propanoic acid;

methyl 3-[4-(4-fluorophenyl)-5-[4-methylsulfonyl phenyl]oxazol-2-yl]propanate;

4-[4-(4-fluorophenyl)-5-[4-methylsulfonylphenyl]oxazol-2-yl]butanoic acid;

methyl 4-[4-(4-fluorophenyl)-5-(4-methylsulfonyl phenyl)oxazol-2-yl]butanate;

3-[4-(4-fluorophenyl)-5-[4-methylsulfonylphenyl]oxazol-2-yl]propanamide;

ethyl 2-[4-(4-fluorophenyl)-5-[4-(methylsulfonyl) phenyl]oxazol-2-yl]-2-benzyl-acetate;

4-(4-fluorophenyl)-2-(cyclohexylethyl)-5-[4-(methylsulfonyl)phenyl]oxazole;

4-(4-fluorophenyl)-2-(3-fluorophenoxymethyl)-5-[4-(methylsulfonyl)phenyl]oxazole;

4-(4-fluorophenyl)-2-(3-chlorophenoxymethyl)-5-[4-(methylsulfonyl)phenyl]oxazole;

4-(4-fluorophenyl)-2-(pyridyloxymethyl)-5-[4-(methylsulfonyl)phenyl]oxazole;

4-(4-fluorophenyl)-5-[4-(methylsulfonyl)phenyl]-2-phenoxymethyloxazole;

4-(4-fluorophenyl)-2-(2-hydroxyethyl)-5-[4-(methylsulfonyl)phenyl]oxazole;

4-(4-fluorophenyl)-2-(hydroxymethyl)-5-[4-(methylsulfonyl)phenyl]oxazole;

4-(4-cyclohexyl)-2-phenyl-5-[4-(methylsulfonyl)phenyl]oxazole;

4-(4-fluorophenyl)-2-benzyloxymethyl-2-[4-(methylsulfonyl)phenyl]oxazole;

4-(4-fluorophenyl)-2-cyclohexyl-5-[4-(methylsulfonyl) phenyl]oxazole; and 5-(4-fluorophenyl)-2-phenyl-4-[4-(methylsulfonyl)phenyl]oxazole.

Within Formula I there is a second subclass of compounds of high interest wherein R is selected from alkyl, hydroxyalkyl, haloalkyl, cycloalkyl, cycloalkylalkyl, aryl optionally substituted at a substitutable position by carboxy, alkyl, alkoxy and halo, aralkyl optionally substituted at a substitutable position on the aryl radical by carboxy, alkyl, alkoxy and halo, aryloxyalkyl optionally substituted at a substitutable position on the aryl radical with halo, carboxy, alkyl and alkoxy, aralkoxyalkyl optionally substituted at a substitutable position by alkyl, carboxy, alkoxy and halo, heteroaryloxyalkyl optionally substituted at a substitutable position on the heteroaryl radical with halo, carboxy, alkyl and alkoxy, alkoxycarbonylalkyl, carboxyalkyl and aminocarbonylalkyl; wherein $R^1$ is selected from cycloalkyl, cycloalkenyl, heteroaryl and aryl optionally substituted at a substitutable position by alkyl, alkoxy and halo; and wherein $R^2$ is amino; or a pharmaceutically-acceptable salt or prodrug thereof; provided R is not methyl.

A more preferred class of compounds of the second subclass consists of those compounds of wherein R is selected from lower alkyl, lower hydroxyalkyl, lower haloalkyl, lower cycloalkyl, lower cycloalkylalkyl, aryl selected from phenyl and naphthyl, optionally substituted at a substitutable position by halo, carboxy, lower alkyl and lower alkoxy, lower aralkyl optionally substituted at a substitutable position on the aryl radical by halo, carboxy, lower alkyl and lower alkoxy, lower aryloxyalkyl optionally substituted at a substitutable position on the aryl radical with halo, carboxy, lower alkyl and lower alkoxy, aralkoxyalkyl optionally substituted at a substitutable position by halo, carboxy, lower alkyl and lower alkoxy, lower heteroaryloxyalkyl optionally substituted at a substitutable position with halo, carboxy, lower alkyl and lower alkoxy, lower alkoxycarbonylalkyl, lower carboxyalkyl and lower aminocarbonylalkyl; and wherein $R^1$ is selected from lower cycloalkyl, lower cycloalkenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by lower alkyl, lower alkoxy and halo; or a pharmaceutically-acceptable salt or prodrug thereof.

A class of compounds of particular interest consists of those compounds of the second subclass wherein R is selected from methyl, ethyl, n-propyl, isopropyl, butyl, tert-butyl, isobutyl, hydroxymethyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyclobutyl, cyclopentyl, cyclohexyl, cycloheptyl, cyclobutylmethyl, cyclopentylmethyl, cyclohexylmethyl, cyclohexylethyl, cyclohexylpropyl, cycloheptylmethyl, aryl selected from phenyl and naphthyl, optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, benzyl, phenethyl, diphenylmethyl and phenpropyl, optionally substituted at a substitutable position on the phenyl radical by fluoro, chloro, bromo, iodo, methyl, ethyl, n-propyl, isopropyl, butyl, tert-butyl, isobutyl, carboxy, methoxy, ethoxy, propoxy and butoxy, phenoxymethyl optionally substituted at a substitutable position with fluoro, chloro, bromo, iodo, methyl, ethyl, n-propyl, isopropyl, butyl, tert-butyl, isobutyl, carboxy, methoxy, ethoxy, propoxy and butoxy, benzyloxymethyl optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, pyridyloxymethyl and quinolyloxymethyl, optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, methoxycarbonylmethyl, ethoxycarbonylmethyl, methoxycarbonylethyl, ethoxycarbonylethyl, acetyl, propanoic, butanoic, pentanoic, hexanoic and aminocarbonylmethyl; and wherein $R^1$ is selected from cyclobutyl, cyclopentyl, cyclohexyl, cycloheptyl, 1-cyclohexenyl, 2-cyclohexenyl, 3-cyclohexenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by methyl, ethyl, n-propyl, isopropyl, butyl, tert-butyl, isobutyl, methoxy, ethoxy, propoxy, butoxy, fluoro, chloro, bromo and iodo.

A family of specific compounds of particular interest within the second subclass consists of compounds and pharmaceutically-acceptable salts thereof as follows:

4-[2-benzyl-5-(phenyl)oxazol-4-yl]benzenesulfonamide;

4-[2-benzyl-5-(4-fluorophenyl)oxazol-4-yl]benzenesulfonamide;

4-[2-benzyl-5-(3,4-difluorophenyl)oxazol-4-yl]
benzenesulfonamide;
4-[2-benzyl-5-(4-chlorophenyl)oxazol-4-yl]
benzenesulfonamide;
4-[2-benzyl-5-(3,4-dichlorophenyl)oxazol-4-yl]
benzenesulfonamide;
4-[2-benzyl-5-(4-methoxyphenyl)oxazol-4-yl]
benzenesulfonamide;
4-[2-benzyl-5-(3,4-dimethoxyphenyl)oxazol-4-yl]
benzenesulfonamide;
4-[2-benzyl-5-(4-methylphenyl)oxazol-4-yl]
benzenesulfonamide;
4-[2-benzyl-5-(3,4-dimethylphenyl)oxazol-4-yl]
benzenesulfonamide;
4-[2-benzyl-5-(3-chloro-4-methylphenyl)oxazol-4-yl]
benzenesulfonamide;
4-[2-benzyl-5-(4-chloro-3-methylphenyl)oxazol-4-yl]
benzenesulfonamide;
4-[2-benzyl-5-(3-chloro-4-methoxyphenyl)oxazol-4-yl]
benzenesulfonamide;
4-[2-benzyl-5-(4-chloro-3-methoxyphenyl)oxazol-4-yl]
benzenesulfonamide;
4-[2-benzyl-5-(3,5-dichloro-4-methoxyphenyl)oxazol-4-yl]
benzenesulfonamide;
4-[2-benzyl-5-(3-fluoro-4-methylphenyl)oxazol-4-yl]
benzenesulfonamide;
4-[2-benzyl-5-(4-fluoro-3-methylphenyl)oxazol-4-yl]
benzenesulfonamide;
4-[2-benzyl-5-(3-fluoro-4-methoxyphenyl)oxazol-4-yl]
benzenesulfonamide;
4-[2-benzyl-5-(2-thienyl)oxazol-4-yl]benzenesulfonamide;
4-[2-benzyl-5-(5-chloro-2-thienyl)oxazol-4-yl]
benzenesulfonamide;
4-[2-benzyl-5-(cyclohexyl)oxazol-4-yl]
benzenesulfonamide;
4-[2-benzyl-5-(1-cyclohexenyl)oxazol-4-yl]
benzenesulfonamide;
4-[2-(ethyl)-5-phenyloxazol-4-yl]benzenesulfonamide;
4-[2-(trifluoromethyl)-5-phenyloxazol-4-yl]
benzenesulfonamide;
4-[2-(difluoromethyl)-5-phenyloxazol-4-yl]
benzenesulfonamide;
4-[2-(hydroxymethyl)-5-phenyloxazol-4-yl]
benzenesulfonamide;
4-[2-(carboxy)-5-phenyloxazol-4-yl]benzenesulfonamide;
4-[2-(methoxycarbonyl)-5-phenyloxazol-4-yl]
benzenesulfonamide;
4-[2-(ethoxycarbonyl)-5-phenyloxazol-4-yl]
benzenesulfonamide;
4-[2-(n-propyl)-5-phenyloxazol-4-yl]benzenesulfonamide;
4-[2-(benzyl)-5-phenyloxazol-4-yl]benzenesulfonamide;
4-[2-(phenoxymethyl)-5-phenyloxazol-4-yl]
benzenesulfonamide;
4-[2-((4-chlorophenoxy)methyl)-5-phenyloxazol-4-yl]
benzenesulfonamide;
4-[2-((4-fluorophenoxy)methyl)-5-phenyloxazol-4-yl]
benzenesulfonamide;
4-[2-((4-carboxyphenoxy)methyl)-5-phenyloxazol-4-yl]
benzenesulfonamide;
4-[2-(2-phenylethyl)-5-phenyloxazol-4-yl]
benzenesulfonamide;
4-[2-(3-phenylpropyl)-5-phenyloxazol-4-yl]
benzenesulfonamide;
4-[2-(carboxymethyl)-5-phenyloxazol-4-yl]
benzenesulfonamide;
4-[2-(ethoxycarbonylmethyl)-5-phenyloxazol-4-yl]
benzenesulfonamide;
4-[2-(methoxycarbonylmethyl)-5-phenyloxazol-4-yl]
benzenesulfonamide;
4-[2-(2-quiniolyloxymethyl)-5-phenyloxazol-4-yl]
benzenesulfonamide;
4-[2-benzyl-4-phenyloxazol-5-yl]benzenesulfonamide;
4-[2-benzyl-4-(3,4-difluorophenyl)oxazol-5-yl]
benzenesulfonamide;
4-[2-benzyl-4-(4-chlorophenyl)oxazol-5-yl]
benzenesulfonamide;
4-[2-benzyl-4-(3,4-dichlorophenyl)oxazol-5-yl]
benzenesulfonamide;
4-[2-benzyl-4-(4-methoxyphenyl)oxazol-5-yl]
benzenesulfonamide;
4-[2-benzyl-4-(3,4-dimethoxyphenyl)oxazol-5-yl]
benzenesulfonamide;
4-[2-benzyl-4-(4-methylphenyl)oxazol-5-yl]
benzenesulfonamide;
4-[2-benzyl-4-(3,4-dimethylphenyl)oxazol-5-yl]
benzenesulfonamide;
4-[2-benzyl-4-(3-chloro-4-methylphenyl)oxazol-5-yl]
benzenesulfonamide;
4-[2-benzyl-4-(4-chloro-3-methylphenyl)oxazol-5-yl]
benzenesulfonamide;
4-[2-benzyl-4-(3-chloro-4-methoxyphenyl)oxazol-5-yl]
benzenesulfonamide;
4-[2-benzyl-4-(4-chloro-3-methoxyphenyl)oxazol-5-yl]
benzenesulfonamide;
4-[2-benzyl-4-(3,5-dichloro-4-methoxyphenyl)oxazol-5-yl]
benzenesulfonamide;
4-[2-benzyl-4-(3-fluoro-4-methylphenyl)oxazol-5-yl]
benzenesulfonamide;
4-[2-benzyl-4-(4-fluoro-3-methylphenyl)oxazol-5-yl]
benzenesulfonamide;
4-[2-benzyl-4-(3-fluoro-4-methoxyphenyl)oxazol-5-yl]
benzenesulfonamide;
4-[2-benzyl-4-(2-thienyl)oxazol-5-yl]benzenesulfonamide;
4-[2-benzyl-4-(5-chloro-2-thienyl)oxazol-5-yl]
benzenesulfonamide;
4-[2-benzyl-4-(cyclohexyl)oxazol-5-yl]
benzenesulfonamide;
4-[2-benzyl-4-(1-cyclohexenyl)oxazol-5-yl]
benzenesulfonamide;
4-[2-(ethyl)-4-phenyloxazol-5-yl]benzenesulfonamide;
4-[2-(trifluoromethyl)-4-phenyloxazol-5-yl]
benzenesulfonamide;
4-[2-(difluoromethyl)-4-phenyloxazol-5-yl]
benzenesulfonamide;
4-[2-(hydroxymethyl)-4-phenyloxazol-5-yl]
benzenesulfonamide;
4-[2-(carboxy)-4-phenyloxazol-5-yl]benzenesulfonamide;
4-[2-(methoxycarbonyl)-4-phenyloxazol-5-yl]
benzenesulfonamide;
4-[2-(ethoxycarbonyl)-4-phenyloxazol-5-yl]
benzenesulfonamide;
4-[2-(propyl)-4-phenyloxazol-5-yl]benzenesulfonamide;
4-[2-(benzyl)-4-phenyloxazol-5-yl]benzenesulfonamide;
4-[2-(phenoxymethyl)-4-phenyloxazol-5-yl]
benzenesulfonamide;
4-[2-((4-chlorophenoxy)methyl)-4-phenyloxazol-5-yl]
benzenesulfonamide;
4-[2-((4-fluorophenoxy)methyl)-4-phenyloxazol-5-yl]
benzenesulfonamide;
4-[2-((4-carboxyphenoxy)methyl)-4-phenyloxazol-5-yl
]benzenesulfonamide;
4-[2-(2-phenethyl)-4-phenyloxazol-5-yl]
benzenesulfonamide;
4-[2-(3-phenpropyl)-4-phenyloxazol-5-yl]
benzenesulfonamide;

4-[2-(carboxymethyl)-4-phenyloxazol-5-yl]
benzenesulfonamide;
4-[2-(ethoxycarbonylmethyl)-4-phenyloxazol-5-yl]
benzenesulfonamide;
4-[2-(methoxycarbonylmethyl)-4-phenyloxazol-5-yl]
benzenesulfonamide;
4-[2-(quiniolyloxymethyl)-4-phenyloxazol-5-yl]
benzenesulfonamide;
4-[5-(4-fluorophenyl)-2-methyl-oxazol-4-yl]
benzenesulfonamide;
4-(4-fluorophenyl)-4-(4-aminosulfonylphenyl)-2-oxazol-2-yl]propanoic acid;
methyl 3-[5-(4-fluorophenyl)-4-(4-aminosulfonylphenyl) oxazol-2-yl]propanate;
4-[4-(4-fluorophenyl)-2-(2-phenylethyl)-oxazol-5-yl]
benzenesulfonamide;
4-[4-(4-fluorophenyl)-2-methyloxazol-5-yl]
benzenesulfonamide;
4-[4-(4-fluorophenyl)-2-phenyloxazol-5-yl]
benzenesulfonamide;
4-[2-benzyl-4-(4-fluorophenyl)oxazol-5-yl]benzene sulfonamide;
4-[4-(4-fluorophenyl)-2-(3-phenylpropyl)oxazol-5-yl]
benzenesulfonamide;
4-[4-(4-fluorophenyl)-2-propyloxazol-5-yl]
benzenesulfonamide;
4-[2-(tert-butyl)-4-(4-fluorophenyl)oxazol-5-yl]
benzenesulfonamide;
4-[4-(4-fluorophenyl)-2-(4-methoxyphenyl) methyloxazol-5-yl]benzenesulfonamide
4-[4-(4-fluorophenyl)-2-(3-methoxyphenyl) methyloxazol-5-yl]benzenesulfonamide;
4-[2-diphenylmethyl-4-(4-fluorophenyl)oxazol-5-yl]
benzenesulfonamide;
4-[4-(4-fluorophenyl)-5-[4-aminosulfonylphenyl]oxazol-2-yl]acetic acid;
ethyl 2-[4-(4-fluorophenyl)-5-[4-aminosulfonylphenyl] oxazol-2-yl]acetate;
3-[4-(4-fluorophenyl)-5-[4-aminosulfonylphenyl]oxazol-2-yl]propanoic acid;
methyl 3-[4-(4-fluorophenyl)-5-[4-aminosulfonylphenyl] oxazol-2-yl]propanate;
4-[4-(4-fluorophenyl)-5-[4-aminosulfonylphenyl]oxazol-2-yl]butanoic acid;
methyl 4-[4-(4-fluorophenyl)-5-[4-aminosulfonyl phenyl] oxazol-2-yl]butanate;
3-[4-(4-fluorophenyl)-5-[4-aminosulfonyl phenyl]oxazol-2-yl]propanamide;
ethyl 2-[4-(4-fluorophenyl)-5-[4-aminosulfonyl phenyl] oxazol-2-yl]-2-benzyl-acetate;
4-[4-(4-fluorophenyl)-2-(cyclohexylethyl)oxazol-5-yl]
benzenesulfonamide;
4-[4-(4-fluorophenyl)-2-(3-fluorophenoxymethyl) oxazol-5-yl]benzenesulfonamide;
4-[4-(4-fluorophenyl)-2-(3-chlorophenoxymethyl)oxazol-5-yl]benzenesulfonamide;
4-[4-(4-fluorophenyl)-2-(pyridyloxymethyl)oxazol-5-yl]
benzenesulfonamide;
4-[4-(4-fluorophenyl)-2-phenoxymethyloxazol-5-yl]
benzenesulfonamide;
4-[4-(4-fluorophenyl)-2-(2-hydroxyethyl)oxazol-5-yl]benzenesulfonamide;
4-[4-(4-fluorophenyl)-2-(hydroxymethyl)oxazol-5-yl]
benzenesulfonamide;
4-[4-(cyclohexyl)-2-phenyloxazol-5-yl]
benzenesulfonamide;
4-[4-(4-fluorophenyl)-2-benzyloxymethyloxazol-5-yl]
benzenesulfonamide;
4-[4-(4-fluorophenyl)-2-cyclohexyloxazol-5-yl]
benzenesulfonamide; and
4-[5-(4-fluorophenyl)-2-phenyloxazol-4-yl]
benzenesulfonamide.

Where the term "alkyl" is used, either alone or within other terms such as "haloalkyl", "alkoxyalkyl" and "hydroxyalkyl", embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one no about six carbon atoms. Examples of such radicals include methyl, ethyl, n-propyl, isopropyl, n-butyl, isobutyl, sec-butyl, tert-butyl, pentyl, iso-amyl, hexyl and the like. Where the term "alkenyl" is used, it embraces linear or branched carbon carbon double bond-containing radicals having two to about twenty carbon atoms or, preferably, two to about twelve carbon atoms. More preferred alkenyl radicals are "lower alkenyl" radicals having two to about six carbon atoms. Suitable "lower alkenyl" may be a straight or branched one such as vinyl, allyl, isopropenyl, 1- or 2-propenyl, 1-, 2- or 3-butenyl, pentenyl or the like. The term "alkynyl" embraces linear or branched radicals having two to about twenty carbon atoms or, preferably, two to about twelve carbon atoms, and containing a carbon-carbon triple bond. The more preferred "lower alkynyl" are radicals having two to ten carbons. Examples of such radicals include ethynyl, 1- or 2-propynyl, 1-, 2- or 3-butynyl and the like and isomers thereof. The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo and polyhaloalkyl radicals may have two or more of the same halo atoms or a combination of different halo radicals. The term "hydroxyalkyl" embraces linear or branched alkyl radicals having one to about twelve carbon atoms any one of which may be substituted with one or more hydroxyl radicals. The term "hydroxyalkenyl" embraces linear or branched alkenyl radicals having two to about ten carbon atoms any one of which may be substituted with one or more hydroxyl radicals. The term "hydroxyalkynyl" embraces linear or branched alkynyl radicals having two to about ten carbon atoms any one of which may be substituted with one or more hydroxyl radicals. The terms "alkoxy" and "alkoxyalkyl" embrace linear or branched oxy-containing radicals each having alkyl portions of one to about twelve carbon atoms, such as methoxy radical. The term "alkoxyalkyl" also embraces alkyl radicals having two or more alkoxy radicals attached to the alkyl radical, that is, to form monoalkoxyalkyl and dialkoxyalkyl radicals. The "alkoxy" or "alkoxyalkyl" radicals may be further substituted with one or more halo atoms, such as fluoro, chloro or bromo, provide haloalkoxy or haloalkoxyalkyl radicals. The term "aryl" embraces aromatic radicals such as phenyl, naphthyl and biphenyl. Preferred aryl radicals are those consisting of one, two, or three benzene rings. The term "heteroaryl" embraces radicals having an unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b] pyridazinyl, etc.], etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term "aralkyl" embraces aryl-substituted alkyl radicals such as benzyl, diphenylmethyl, triphenylmethyl, phenethyl, and diphenethyl. The terms benzyl and phenylmethyl are interchangeable. The term "aryloxy" embrace oxy-containing aryl radicals attached through an oxygen atom to other radicals. More preferred aryloxy radicals are "lower aryloxy" radicals having a phenyl radical. An example of such radicals is phenoxy. The term "aryloxyalkyl" embraces alkyl radicals having one or more aryloxy radicals attached to the alkyl radical, that is, to form monoaryloxyalkyl and diaryloxyalkyl radicals. The "aryloxy" or "aryloxyalkyl" radicals may be further substituted to provide haloaryloxyalkyl radicals alkylaryloxy radicals, and the like. Examples of such radicals include chlorophenoxy and methylphenoxy. The term "aralkyloxy" embrace oxy-containing aralkyl radicals attached through an oxygen atom to other radicals. The term "aralkyloxyalkyl" embraces alkyl radicals having one or more aralkyloxy radicals attached to the alkyl radical, that is, to form monoaralkyloxyalkyl and diaralkyloxyalkyl radicals. The "aralkyloxy" or "aralkyloxyalkyl" radicals may be further substituted on the aryl ring portion of the radical. The term "heteroaryloxyalkyl" embraces alkyl radicals having one or more heteroaryloxy radicals attached to the alkyl radical, that is, to form monoheteroaryloxyalkyl and diheteroaryloxyalkyl radicals. The "heteroaryloxy" radicals may be further substituted on the heteroaryl ring portion of the radical. The term "arylthio" embraces radicals containing an aryl radical, as described above, attached to a divalent sulfur atom, such as a phenylthio radical. The term "arylthioalkyl" embraces alkyl radicals substituted with one or more arylthio radicals, as described above. The term "cycloalkyl" embraces radicals having three to ten carbon atoms, such as cyclopropyl cyclobutyl, cyclopentyl, cyclohexyl and cycloheptyl. The term "cycloalkylalkyl" embraces alkyl radicals substituted with cycloalkyl radicals having three to ten carbon atoms, such as cyclopropylmethyl, cyclobutylmethyl, cyclopentylmethyl, cyclohexylmethyl, cyclohexylethyl, cyclohexylpropyl and cycloheptylmethyl. The term "cycloalkenyl" embraces unsaturated radicals having three to ten carbon atoms, such as cyclopropenyl, cyclobutenyl, cyclopentenyl, cyclohexenyl and cycloheptenyl. The term "sulfonyl", whether used alone or linked to other terms such as alkylsulfonyl, denotes respectively divalent radicals —$SO_2$—. "Alkylsulfonyl" embraces alkyl radicals attached to a sulfonyl radical, where alkyl is defined as above. The "alkylsulfonyl" radicals may be further substituted with one or more halo atoms, such as fluoro, chloro or bromo, to provide haloalkylsulfonyl radicals. The terms "sulfamyl", "aminosulfonyl" and "sulfonamidyl" denote a sulfonyl radical substituted with an amine radical, forming a sulfonamide (—$SO_2NH_2$). The terms "carboxy" or "carboxyl", whether used alone or with other terms, such as "carboxyalkyl", denotes —$CO_2H$. The terms "carboxyalkyl" and "alkanoyl" embrace radicals having a carboxy radical as defined above, attached to an alkyl radical, which may be substituted or unsubstituted. Examples of such radicals include formyl, acetyl, propionyl, butyryl, isobutyryl, valeryl, isovaleryl, pivaloyl, hexanoyl, trifluoroacetyl or the like, in which the preferable one is formyl, acetyl, propionyl or trifluoroacetyl. The term "alkoxycarbonyl" means a radical containing an alkoxy radical, as defined above, attached via an oxygen atom to a "carbonyl" (—C=O) radical. Examples of such "alkoxycarbonyl" ester radicals include substituted or unsubstituted methoxycarbonyl, ethoxycarbonyl, propoxycarbonyl, butoxycarbonyl and hexyloxycarbonyl. The term "alkoxycarbonylalkyl" embraces alkyl radicals having one or more alkoxycarbonyl radicals attached to the alkyl radical. The term "aminocarbonylalkyl" embraces alkyl radicals having one or more aminocarbonyl radicals attached to the alkyl radical. The term "alkylaminocarbonylalkyl" embraces alkyl radicals having aminocarbonyl radicals substituted with one or two alkyl radicals. Examples of such include N-alkylaminocarbonylalkyl and N,N-dialkylaminocarbonylalkyl radicals such as N-methylaminocarbonylmethyl and N,N-dimethylaminocarbonylmethyl.

The present invention comprises a pharmaceutical composition for the treatment of inflammation and inflammation-associated disorders, such as arthritis, comprising a therapeutically-effective amount of a compound of Formula I in association with at least one pharmaceutically-acceptable carrier, adjuvant or diluent.

The present invention also comprises a therapeutic method of treating inflammation or inflammation-associated disorders in a subject, the method comprising administering to a subject having such inflammation or disorder a therapeutically-effective amount of a compound of Formula I.

Also included in the family of compounds of Formula I are isomeric forms including and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propanoic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, p-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

The compounds of the present invention may contain prodrugs of compounds of the current invention. The term "prodrug" embraces compounds which are metabolized in vivo into compounds of the invention.

The compounds of the present invention may contain asymmetric carbon atoms, and, therefore, the instant invention may also include the individual diastereomers and enantiomers, which may be prepared or isolated by methods known to those skilled in the art.

In other words, any resulting racemate can be resolved into the optical antipodes by known methods, for example, by separation of the diastereomeric salts thereof, with an optically active acid, and liberating the optically active amine compound by treatment with a base. Racemic compounds of the present invention can thus be resolved into their optical antipodes e.g., by fractional crystallization of d- or l-(tartrates, mandelates, or camphorsulfonate) salts.

Additional methods for resolving optical isomers, known to those skilled in the art may be used, for example, those discussed by J. Jaques et al in *Enantiomers, Racemates, and Resolutions*, John Wiley and Sons, New York (1981).

Compounds of the present invention also are meant to include, where possible, hydrated species.

GENERAL SYNTHETIC PROCEDURES

The compounds of the invention can be synthesized according to the following procedures of Schemes I-VIII, wherein the R–R² substituents are as defined for Formula I, above, except where further noted.

Scheme I

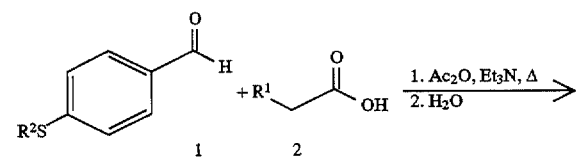

-continued
Scheme I

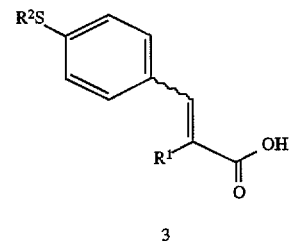

1. DPPA, Et₃N,
   Ph—CH₃,
   0° C. - Δ
2. t-BuOH, HCl,
   RT- Δ

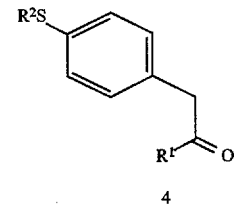

Synthetic Scheme I shows the four step procedure which can be used to prepare the substituted ketone compounds 4 from the substituted benzaldehyde 1 and acid 2, where $R^2$ is alkyl. In step one, benzaldehyde 1 and substituted acetic acid 2 are first heated in acetic anhydride and triethylamine via a Perkin condensation. In step two, hydrolysis produces the corresponding 2,3-disubstituted acrylic acids 3. In step three, the acrylic acids 3 are reacted with diphenylphosphorylazide (DPPA) and triethylamine in toluene at 0° C. and then warmed to room temperature to form acylazides. In step four, the crude acylazides are heated to form an isocyanate via a Curtius rearrangement. The isocyanate is trapped as the N-t-butyloxycarbonyl enamine derivative via the addition of tert-butanol. Acidic hydrolysis, such as by using concentrated HCl, provides the substituted ketone 4 intermediates.

Scheme II

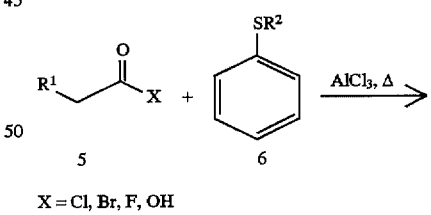

X = Cl, Br, F, OH

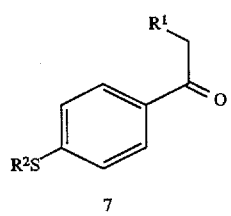

Synthetic Scheme II shows an alternative approach which can be used to prepare substituted ketone intermediates 7, isomers of 4 where $R^2$ is alkyl, via the use of Friedel-Crafts acylation. An acylating agent 5, such as an acid chloride, is treated with aluminum chloride in an inert solvent, such as methylene chloride, chloroform, nitrobenzene, dichlorobenzene or chlorobenzene, and reacted with alkylthiobenzene 6 to form ketone 7.

Other synthetic approaches are possible to form the desired ketones. These alternatives include reacting appropriate Grignard or lithium reagents with substituted acetic acids or corresponding esters.

5-(4-alkylsulfonylphenyl)oxazoles 12 of Formula I from ketone 4 (prepared in Scheme I). Preparation of the silyl enol ether 8 is followed by oxidation, such as with m-chloroperbenzoic acid, to give the appropriate silylated benzoin 9. Desilylation of this silylated benzoin 9 is achieved using aqueous acid, such as trifluoroacetic acid, to give the desired benzoin 10. Reaction of the benzoin 10 with the appropriate acid chloride in the presence of base, such as

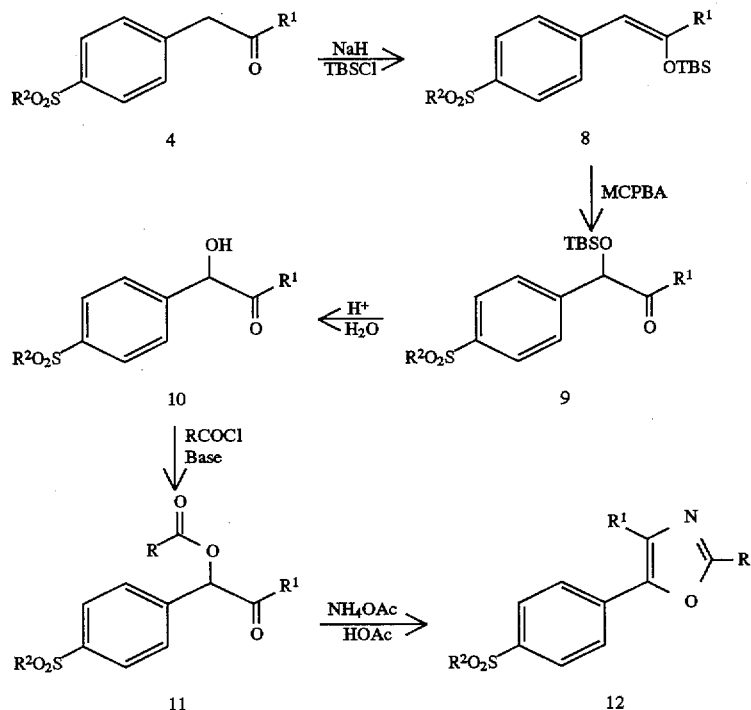

TBSCl is tert-butyl-dimethylsilyl chloride MCPBA is m-chloroperoxybenzoic acid.

Scheme III shows the five step synthesis, as described in U.S. Pat. No. 3,647,858, which can be used to prepare the pyridine, gives the benzoin esters 11 which may be converted to the antiinflammatory oxazoles 12 of the present invention upon treatment with ammonium acetate in acetic acid at reflux.

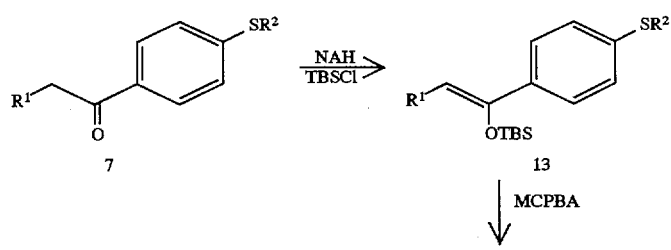

-continued
Scheme IV

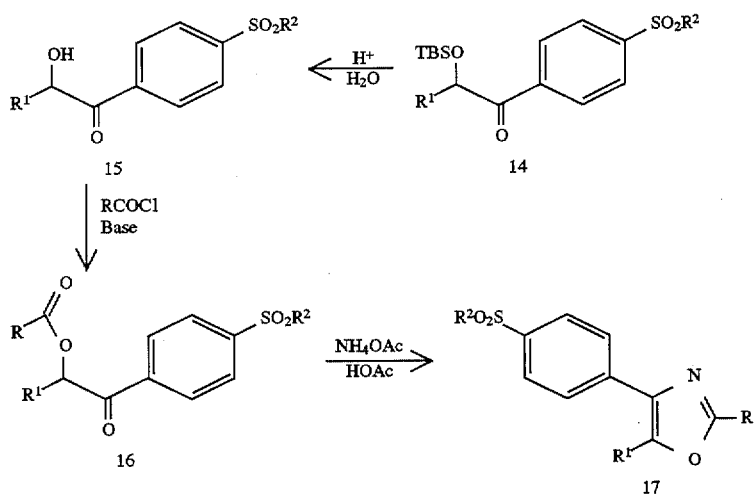

Scheme IV shows the five step synthesis, similar to that described above in Scheme III, which can be used to prepare the 4-(4-alkylsulfonylphenyl)ozaxoles 17 of Formula I from ketone 7 (prepared in Scheme II). Preparation of the silyl enol ether 13 is followed by oxidation, such as with m-chloroperbenzoic acid, to give the appropriate silylated benzoin 14. Desilylation of this silylated benzoin 14 is achieved using aqueous acid, such as trifluoroacetic acid to give the desired benzoin 15. Reaction of the benzoin 15 with the appropriate acid chloride in the presence of base, such as pyridine, gives the benzoin esters 16 which may be converted to the antiinflammatory oxazoles 17 of the present invention upon treatment with ammonium acetate in acetic acid at reflux.

Scheme V shows the four step synthesis which can be used to prepare oxazoles 20 from ketones 4 (prepared in Synthetic Scheme I). In step one, ketones 4 are readily brominated via the addition of bromine in acetic acid to form the 2-bromoethanone intermediates. In step two, reaction of the bromoethanone with aqueous acetone yields the benzoin 18. In step three, reaction of the benzoin 18 with the appropriate acid chloride in the presence of base, such as pyridine, gives the benzoin esters 19. In step four, benzoin esters 19 are converted to the oxazoles 20 upon treatment with ammonium acetate in acetic acid at reflux.

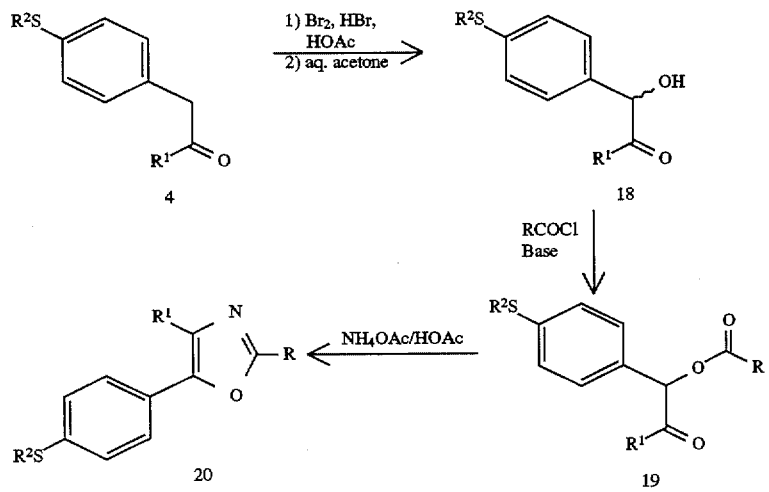

Scheme VI

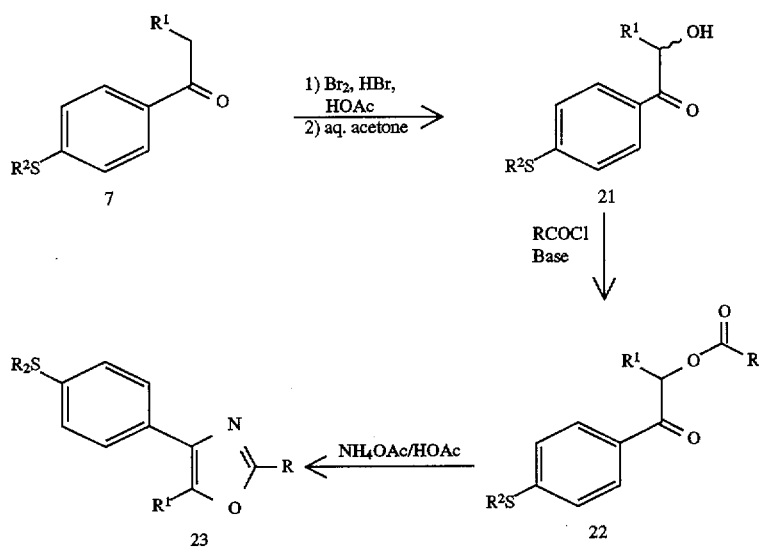

Similarly, Scheme VI shows the four step synthesis which can be used to prepare oxazoles 23 from ketones 7 (prepared in Synthetic Scheme II). In step one, ketones 7 are readily brominated via the addition of bromine in acetic acid to form the 2-bromoethanone intermediates. In step two, reaction of the bromoethanone with aqueous acetone yields the benzoin 21. In step three, reaction of the benzoin 21 with the appropriate acid chloride in the presence of base, such as pyridine, gives the benzoin esters In step four, benzoin esters 22 are converted to the oxazoles 23 upon treatment with ammonium acetate in acetic acid at reflux.

Scheme VII

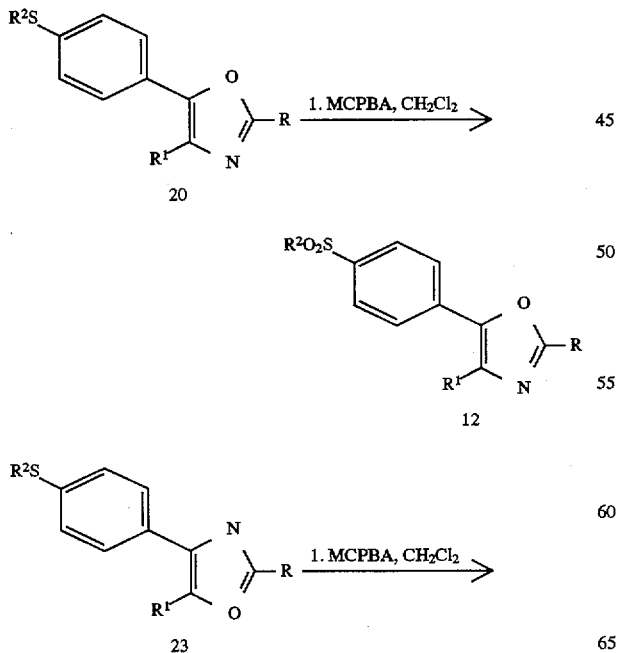

-continued
Scheme VII

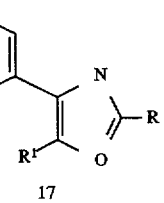

An alternative synthesis of the alkylsulfonylphenyloxazoles 12 and 17 is accomplished as shown in Synthetic Scheme VII from oxazoles 20 and 23 (prepared in Schemes V and VI). Oxazoles 20 and 23, where $R^2$ is an alkyl radical, are oxidized, such as with MCPBA (2 equivalents) in methylene chloride to form the antiinflammatory alkylsulfonyl oxazoles 12 and 17. Other suitable oxidizing agents include Oxone®, hydrogen peroxide, periodate, peracetic acid and the like.

Scheme VIII

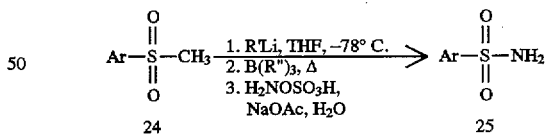

Synthetic Scheme VIII shows the three step procedure used to prepare sulfonamide antiinflammatory agents 25 from their corresponding methyl sulfones 24. In step one, a THF solution of the methyl sulfones 24 at −78° C. is treated with an alkyllithium reagent, e.g., methyllithium, n-butyllithium, etc. In step two, the anions generated in step one are treated with an organoborane, e.g., triethylborane, tributylborane, etc., at −78° C. then allowed to warm to ambient temperature prior to stirring at reflux. In step three, an aqueous solution of sodium acetate and hydroxyamine-O-sulfonic acid is added to provide the corresponding sulfonamide antiinflammatory agents 25 of this invention.

The following examples contain detailed descriptions of the methods of preparation of compounds of Formula I.

These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

EXAMPLE 1

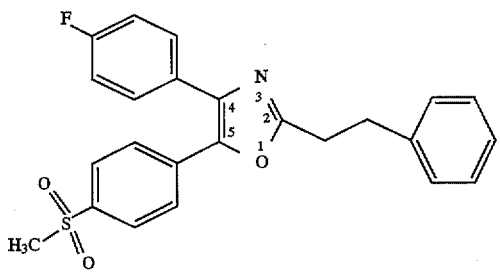

4-(4-Fluorophenyl)-2-(2-phenylethyl)-5-(4-(methylsulfonyl)phenyl)oxazole

Step 1

Preparation of 1-(4-fluoromethyl)-2-hydroxy-2-(methylsulfonyl)phenyl)ethanone

A suspension of 2.03 g sodium hydride in 125 mL tetrahydrofuran (THF) was stirred at 0° C. under a nitrogen atmosphere as a solution containing 20.0 g of 1-(4-fluorophenyl)-2-[4-(methylthio)phenyl]ethanone, as prepared in U.S. Pat. No. 3,647,858, in 100 mL of THF was added dropwise over 30 minutes. The reaction was allowed to warm to 25° C. for 18 hours. A solution containing 12.7 g (84.5 mmol) of tert-butyl-dimethylsilyl chloride (DBSCL) in 20 mL THF was added over 5 minutes and the resulting solution stirred at 25° C. for 18 hours. The reaction was quenched by pouring into aqueous sodium bicarbonate. The mixture was extracted with ethyl acetate and the combined organic extracts dried over sodium sulfate. Concentration in vacuo provides a yellow oil, which solidified on standing to give 27.9 g of the silyl enol ether. NMR spectra was consistent with the assigned structure. The silyl enol ether was used without further purification.

A solution containing 27.9 g of the silyl enol ether in 500 mL methylene chloride (CH$_2$Cl$_2$) was cooled to 0° C. under a nitrogen atmosphere while being stirred mechanically. 77.1 g of m-chloroperoxybenzoic acid (technical grade, 50–60%) was added and the reaction was stirred at 0° C. for 2 hours and allowed to warm to 25° C. over 1 hour. The reaction mixture was washed with an aqueous solution of sodium metabisulfite, followed by aqueous sodium bicarbonate. The organic solution was dried over sodium sulfate and concentrated in vacuo to give 24.5 g of 1-(4-fluorophenyl)-2-tert-butyldimethylsilyloxy-2-[4-(methylsulfonyl)phenyl]ethanone. NMR spectra were consistent with the assigned structure. This material was used without further purification.

The benzoin silyl ether was dissolved in 100 mL of 90% aqueous trifluoroacetic acid and stirred at 25° C. for 18 hours. The reaction was quenched by slowly pouring into saturated aqueous sodium bicarbonate solution. The product was extracted with ethyl acetate and the combined organic extracts were dried over sodium sulfate. Concentration in vacuo provided an oily solid, which was recrystallized from 50% ethyl acetate/isooctane to give 15.5 g of a crystalline white solid (mp 122°–123° C.) whose structure was assigned as 1-(4-fluorophenyl)-2-hydroxy-2-(methylsulfonyl)phenyl) ethanone on the basis of its spectral properties.

The isomeric benzoin, 2-(4-fluorophenyl)-2-hydroxy-1-(4-(methylsulfonyl)phenyl)ethanone, was prepared analogously from 2-(4-fluorophenyl)-1-[4-(methylthio)phenyl ethanone.

Step 2

Preparation of 4-(4-fluorophenyl)-2-(2-phenylethyl)-5-(4-(methylsulfonyl)phenyl)ozaxole A solution containing 5.00 g of 1-(4-fluorophenyl)-2-hydroxy-2-(4-(methylsulfonyl)phenyl)ethanone in 100 mL methylene chloride (CH$_2$Cl$_2$) was stirred at 25° C. as 6.60 mL of pyridine was added, followed by 3.61 mL of hydrocinnamoyl chloride.

The reaction was stirred at 25° C. for 48 hours, after which the organic solution was washed with 1N HCl, dried over sodium sulfate and concentrated in vacuo to give an oily solid. This material was recrystallized from 50% ethyl acetate/isooctane to give 4.40 g of a beige crystalline solid (mp 152°–153.5° C.). NMR spectra were consistent with the assigned structure of 1-(4-fluorophenyl)-2-[4-(methylsulfonyl)phenyl]-2-(2-phenyl)propionyloxy ethanone. This material was dissolved in 100 mL of glacial acetic acid and 7.70 g of ammonium acetate was added. The reaction was heated to reflux with stirring for 1.5 hours, after which it was cooled to room temperature and poured into 100 mL of water. The product was extracted with ethyl acetate and the combined organic extracts washed with aqueous sodium bicarbonate, dried over sodium sulfate and concentrated in vacuo to give an oily solid which was recrystallized from 50% ethyl acetate/isooctane to give 3.55 g of 4-(4-fluorophenyl)-2-(2-phenylethyl)-5-(4-(methylsulfonyl)phenyl)oxazole as a white crystalline solid (mp 117°– 118° C.). NMR spectra was consistent with the assigned structure.

EXAMPLE 2

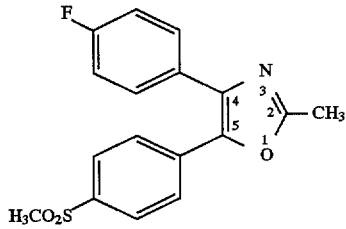

4-(4-Fluorophenyl)-2-methyl-5-[4-(methylsulfonyl) phenyl]oxazole 4-(4-Fluorophenyl)-2-methyl-5-[4-(methylsulfonyl) phenyl]oxazole was prepared in an analogous manner to that shown in Example 1. Melting point: 158°–159° C.

EXAMPLE 3

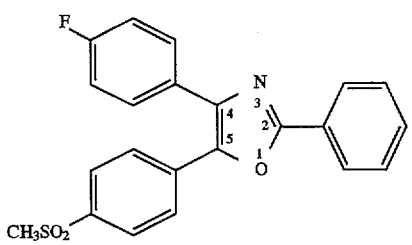

4-(4-Fluorophenyl)-5-[4-(methylsulfonyl)phenyl]-2-phenyloxazole 4-(4-Fluorophenyl)-5-[4-(methylsulfonyl)phenyl]-2-phenyloxazole was prepared in a manner analogous to Example 1. Melting point: 204°–205° C.

EXAMPLE 4

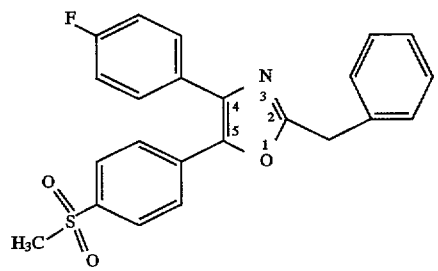

2-Benzyl-4-(4-fluorophenyl)-5-(4-(methylsulfonyl)phenyloxazole

2-Benzyl-4-(4-fluorophenyl)-5-(4-(methylsulfonyl) phenyloxazole was prepared in a manner analogous to Example 1. The $^m/_z$ 408 (M+H)$^+$ was consistent with the assigned structure.

EXAMPLE 5

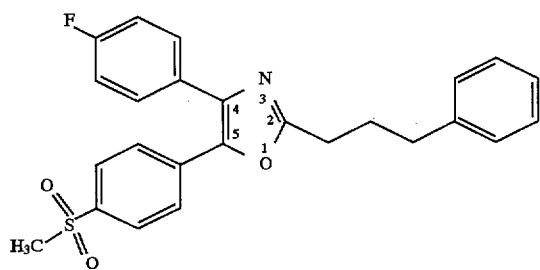

4-(4-Fluorophenyl)-5-[4-methylsulfonylphenyl]-2-(3-phenylpropyl)oxazole 4-(4-Fluorophenyl)-5-[4-methylsulfonyl phenyl]-2-(3-phenylpropyl)oxazole was prepared in a manner analogous to Example 1. The $^m/_z$ 436 (M+H)$^+$ was consistent with the assigned structure.

EXAMPLE 6

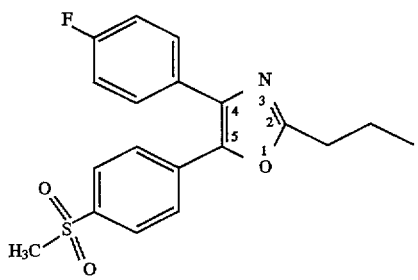

4-(4-Fluorophenyl)-5-[4-methylsulfonylphenyl]-2-propyloxazole 4-(4-Fluorophenyl)-5-[4-methylsulfonyl phenyl]-2-propyloxazole was prepared in a manner analogous to Example 1. The $^m/_z$ 360 (M+H)$^+$ was consistent with the assigned structure.

EXAMPLE 7

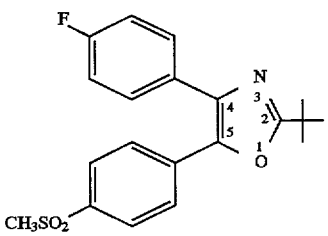

2-(Tert-butyl)-4-(4-fluorophenyl)-5-[4-(methylsulfonyl)phenyl]oxazole 2-(Tert-butyl)-4-(4-fluorophenyl)-5-[4-(methylsulfonyl) phenyl]oxazole was prepared in a manner analogous to Example 1. Melting point: 130°–131° C.

EXAMPLE 8

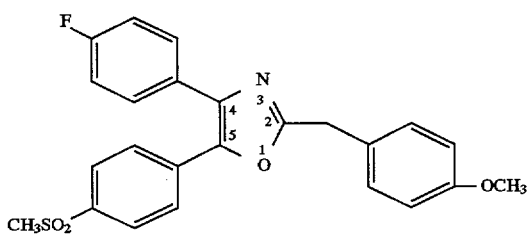

4-(4-Fluorophenyl)-2-(4-methoxyphenyl)methyl-5-[4-methylsulfonylphenyl]oxazole 4-(4-Fluorophenyl)-2-(4-methoxyphenyl)methyl-5-[4-methylsulfonylphenyl]oxazole was prepared in a manner analogous to Example 1. Melting point: 123°–124° C.

EXAMPLE 9

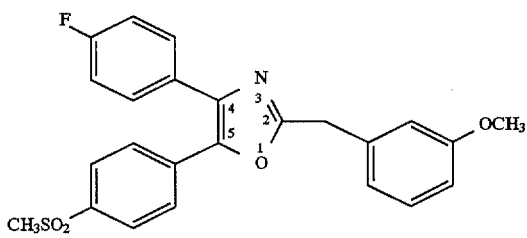

4-(4-Fluorophenyl)-2-(3-methoxyphenyl)methyl-5-[4-methylsulfonylphenyl]oxazole 4-(4-Fluorophenyl)-2-(3-methoxyphenyl)methyl-5-[4-methylsulfonylphenyl]oxazole was prepared in a manner analogous to Example 1. The $^m/_z$ 437 (M+H)$^+$ was consistent with the assigned structure.

EXAMPLE 10

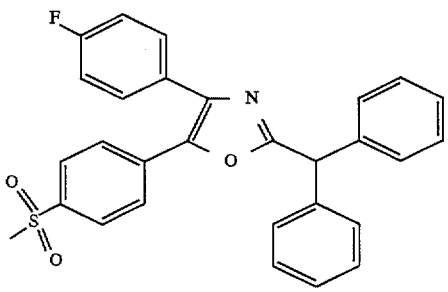

2-Diphenylmethyl-4-(4-fluorophenyl)-5-[4-methylsulfonylphenyl]oxazole

2-Diphenylmethyl-4-(4-fluorophenyl)-5-[4-methylsulfonylphenyl]oxazole was prepared in a manner analogous to Example 1. Melting point: 155°–156° C.

EXAMPLE 11

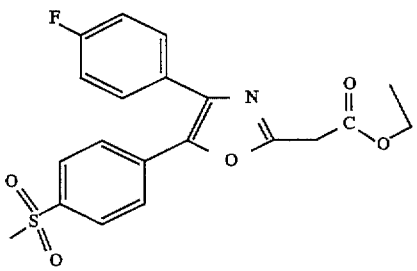

Ethyl 2-[4-(4-fluorophenyl)-5-(4-methylsulfonylphenyl)oxazol-2-yl]acetate

Ethyl 2-[4-(4-fluorophenyl)-5-(4-methylsulfonylphenyl)oxazol-2-yl]acetate was prepared in a manner analogous to Example 1. Melting point: 123°–124° C.

EXAMPLE 12

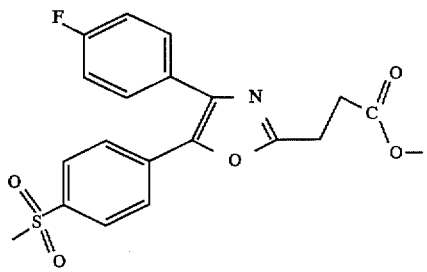

Methyl 3-[4-(4-fluorophenyl)-5-[4-methylsulfonylphenyl]oxazol-2-yl]propanate

Methyl 3-[4-(4-fluorophenyl)-5-[4-methylsulfonylphenyl]oxazol-2-yl]propanate was prepared in a manner analogous to Example 1. The $^m/_z$ 404 (M+H)$^+$ was consistent with the assigned structure.

EXAMPLE 13

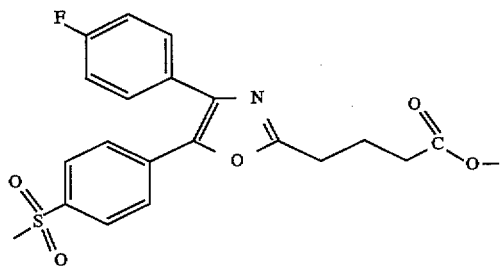

Methyl 4-[4-(4-fluorophenyl)-5-[4-methylsulfonylphenyl]oxazol-2-yl]butanate

Methyl 4-[4-(4-fluorophenyl)-5-[4-methylsulfonylphenyl]oxazol-2-yl]butanate was prepared in a manner analogous to Example 1. Melting point: 89°–91° C.

EXAMPLE 14

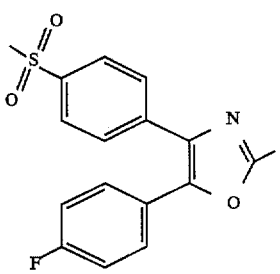

5-(4-Fluorophenyl)-2-methyl-4-[4-(methylsulfonyl)phenyl]oxazole 5-(4-Fluorophenyl)-2-methyl-4-[4-(methylsulfonyl)phenyl]oxazole was prepared in a manner analogous to Example 1, but with 2-(4-fluorophenyl)-1-[4-(methylthio)phenyl]ethanone as the starting material. The $^m/_z$ 332 (M+H)$^+$ was consistent with the assigned structure.

EXAMPLE 15

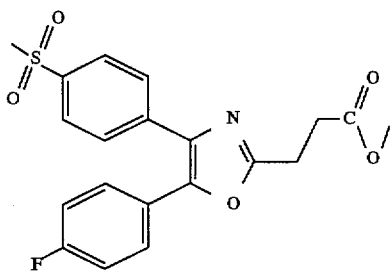

Methyl 3-[5-(4-fluorophenyl)-4-[4-(methylsulfonyl)phenyl]oxazol-2-yl]propanate

Methyl 3-[5-(4-fluorophenyl)-4-[4-(methylsulfonyl)phenyl]oxazol-2-yl]propanate was prepared in a manner analogous to Example 14. The $^m/_z$ 404 (M+H)$^+$ was consistent with the assigned structure.

EXAMPLE 16

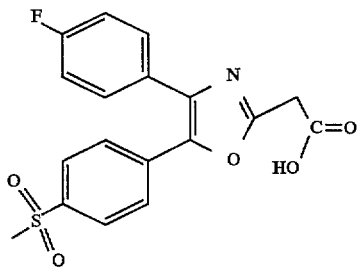

2-[4-(4-Fluorophenyl)-5-[4-(methylsulfonyl)phenyl]oxazol-2-yl]acetic acid

2-[4-(4-Fluorophenyl)-5-[4-(methylsulfonyl)phenyl]oxazol-2-yl]acetic acid was prepared from Example 11 via alkaline hydrolysis using 1N sodium hydroxide in methanol and appropriate reaction conditions. Melting point: 118°–120° C.

EXAMPLE 17

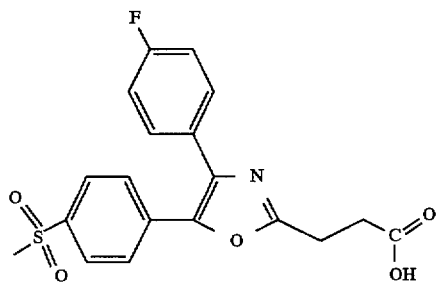

3-[4-(4-Fluorophenyl)-5-[4-(methylsulfonyl)phenyl]oxazol-2yl]propanoic acid

3-[4-(4-Fluorophenyl)-5-[4-(methylsulfonyl)phenyl]oxazol-2-yl]propanoic acid was prepared from Example 12 in a manner analogous to Example 17. Melting point: 197°–198° C. The $^m/_z$ 390 (M+H)$^+$ was consistent with the assigned structure.

EXAMPLE 18

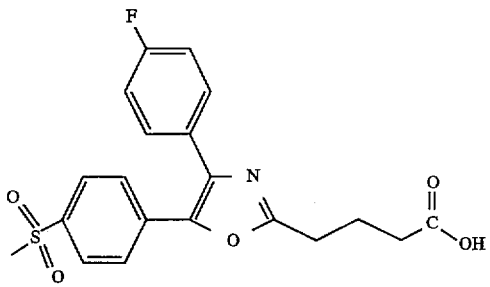

4-[4-(4-Fluorophenyl)-5-[4-(methylsulfonyl)phenyl]oxazol-2-yl]butanoic acid

4-[4-(4-Fluorophenyl)-5-[4-(methylsulfonyl)phenyl]oxazol-2-yl]butanoic acid was prepared from Example 13 in a manner analogous to Example 17. Melting point: 140°–141° C. The $^m/_z$ 404 (M+H)$^+$ was consistent with the assigned structure.

EXAMPLE 19

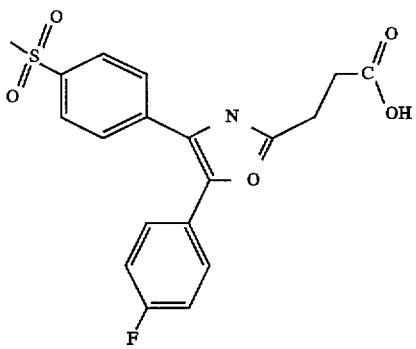

3-[5-(4-Fluorophenyl)-4-[4-(methylsulfonyl)phenyl]oxazol-2-yl]propanoic acid

3-[5-(4-Fluorophenyl)-4-[4-(methylsulfonyl)phenyl]oxazol-2-yl]propanoic acid was prepared from Example 15 in a manner analogous to Example 17. The $^m/_z$ 390 (M+H)$^+$ was consistent with the assigned structure.

EXAMPLE 20

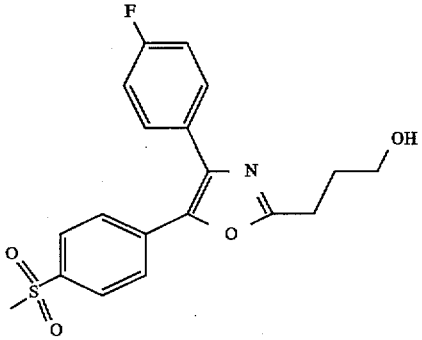

4-(4-Fluorophenyl)-2-(3-hydroxypropyl)-5-[4-(methylsulfonyl)phenyl]oxazole

A solution containing 100 mg (0.239 mmol) of 3-[4-(4-fluorophenyl)-5-[4-(methylsulfonyl)phenyl]oxazol-2-yl]

propanoic acid, methyl ester in 10 mL of tetrahydrofuran was cooled to 0° C. with stirring under a nitrogen atmosphere as 0.53 mL of diisobutylaluminum hydride (1M in toluene, 0.523 mmol) was added dropwise over 5 minutes. The reaction was allowed to warm to 25° C. and poured into 100 mL of a saturated solution of sodium potassium tartarate. Ethyl acetate (100 mL) was added and the mixture was stirred until the layers separated (approx. 1 hour). The organic layer was separated and dried over sodium sulfate. Concentration in vacuo gave an oily solid, which was recrystallized from 50% ethyl acetate-isooctane to give 75 mg of a white crystalline solid (mp 123°–124° C.) which was characterized on the basis of its spectral characteristics: $^1$H-NMR (CDCl$_3$, 300 MHz) ∂ 2.10 (m, 2H), 2.56 (bs, 1H), 3.01 (t, 2H, J=7.0 Hz), 3.07 (s, 3H), 3.80 (t, 2H, J=5.9 Hz), 7.09 (t, 2H, J=8.5 Hz), 7.57 (dd, 2H, J=8.5 and 5.5 Hz), 7.73 (d, 2H, J=8.5 Hz) and 7.89 (d, 2H, J=8.5 Hz). $^{19}$F-NMR (CDCl$_3$, 280 MHz) ∂–111.97. LRMS m/z 376 (M+H)+. HRMS calc. for C$_{19}$H$_{18}$NO$_4$FS: 376.1019. Observed: 376.1026. Analysis calc. for C$_{19}$H$_{18}$NO$_4$FS-C: 60.79, H: 4.83, N: 3.73. Observed-C: 60.53, H: 4.85, N: 3.66.

EXAMPLE 21

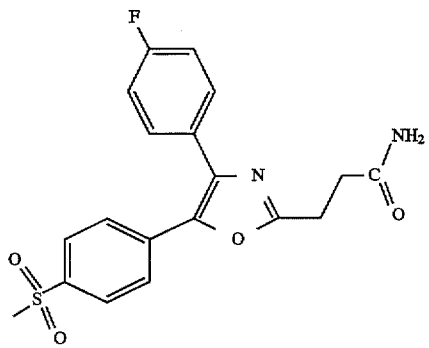

3-[4-(4-Fluorophenyl)-5-(4-(methylsulfonyl)phenyl) oxazol-2-yl]propanamide

3-[4-(4-fluorophenyl)-5-(4-(methylsulfonyl)phenyl) oxazol-2-yl]propanamide was prepared by treating methyl 3-[4-(4-fluorophenyl)-5-(4-(methylsulfonyl)phenyl)oxazol-2-yl]propanoic acid, (Example 12) with excess ammonia in methanol for 5 days. Melting point: 193°–195° C.

EXAMPLE 22

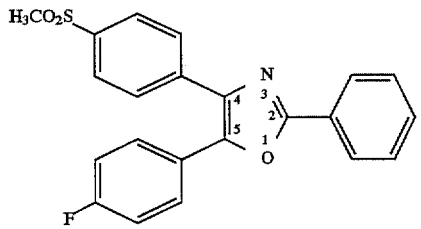

5-(4-Fluorophenyl)-2-phenyl-4-[4-(methylsulfonyl) phenyl]oxazole

Step 1

Preparation of 5-(Fluorophenyl)-4-[4-(methylthio) phenyl]-2-phenyloxazole

A solution containing 560 mg (2.03 mmol) of 2-(4-fluorophenyl)-2-hydroxy-1-[4-(methylthio)phenyl]ethanone in 50 mL of methylene chloride was stirred at 25° C. as 0.82 mL (10.15 mmol) of pyridine was added, followed by 0.28 mL (2.44 mmol) of benzoyl chloride. The reaction was stirred at 25° C. for 2 days, after which it was washed with 1N HCl, dried over sodium sulfate and concentrated in vacuo to give a crude oil which was characterized as the benzoin ester on the basis of its spectral characteristics: $^1$H-NMR (CDCl$_3$, 300 MHz) ∂ 2.53 (s, 3H), 7.08 (s, 1H), 7.12 (t, 2H, J=8.7 Hz), 7.27 (d, 2H, J=8.7 Hz), 7.49 (t, 2H, J=7.7 Hz), 7.60 (m, 3H), 7.94 (d, 2H, J=8.7 Hz) and 8.14 (d, 2H, J=8.7 Hz). This material was dissolved in 50 mL of glacial acetic acid and 1.56 g (20.3 mmol) of ammonium acetate was added. The reaction was heated at reflux for 2 hours, cooled to 25° C. and poured into 100 mL of water. The aqueous solution was extracted with ethyl acetate and the combined organic extracts were washed with water and sodium bicarbonate solution, dried over sodium sulfate and concentrated in vacuo. The crude solid was purified by flash chromatography using a silica gel column and 50% ethyl acetate/hexane as the eluent to give a white solid which was recrystallized from 50% ethyl acetate/isooctane to give 450 mg (61%) of a white crystalline solid (mp 118°–119° C.) whose structure was assigned as 5-(4-fluorophenyl)-4-[4-(methylthio)phenyl]-2-phenyl oxazole on the basis of its spectral characteristics: $^1$H-NMR (CDCl$_3$, 300 MHz) ∂ 2.52 (s, 3H), 7.10 (t, 2H, J=8.8 Hz), 7.28 (d, 2H, J=8.5 Hz), 7.47 (m, 3H), 7.62 (m, 4H) and 8.13 (m, 2H). $^{19}$F-NMR (CDCl$_3$, 280 MHz) ∂–111.96. LRMS m/z 361 (M)+. HRMS Calc'd. for C$_{22}$H$_{16}$NOFS: 361.0937. Observed: 361.0970. Analysis Calc'd. for C$_{22}$H$_{16}$NOFS: C, 71.51; H, 6.55; N, 3.79. Observed: C, 72.85; H, 4.52; N, 3.84.

Step 2

Preparation of 5-(4-Fluorophenyl)-4-[4-(methylsulfinyl)phenyl]-2-phenyloxazole

A solution containing 64 mg (0.173 mmol) of 5-(4-fluorophenyl)-4-[4-(methylthio)phenyl]-2-phenyloxazole in 10 mL of methylene chloride was stirred at –78° C. as 60 mg (0.173 mmol based on 50% purity) of m-chloroperoxybenzoic acid was added all at once. The reaction was stirred at –78° C. for 1 hour. Thin-layer chromatography (TLC) (silica, 50% hexane-ethyl acetate) indicated that the reaction mixture consisted of mostly sulfoxide, with a minor amount of sulfide and sulfone. The reaction was poured into a solution of aqueous sodium metabisulfite. The aqueous solution was extracted using ethyl acetate and the organic layer was washed with saturated sodium metabisulfite, saturated sodium bicarbonate and brine. The resulting clear solution was dried over sodium sulfate and concentrated in vacuo to give a white solid which was purified by flash chromatography on a silica gel column using 50% ethyl acetate/hexane as the eluent. Recrystallization from 50% ethyl acetate/isooctane gave 48 mg (74%) of a white crystalline solid (mp 164°–165° C.) whose structure was assigned as 5-(4-fluorophenyl)-4-[4-(methylsulfinyl)phenyl]-2-phenyl oxazole on the basis of its spectral characteristics: $^1$H-NMR (CDCl$_3$, 300 MHz) ∂ 2.80 (s, 3H), 7.16 (t, 2H, J=8.5 Hz), 7.54 (m, 3H), 7.66–7.75 (m, 4H), 7.93 (d, 2H, J=8.5 Hz) and 8.19 (m, 2H). LRMS m/z 377 (M)+. HRMS Calc'd. for C$_{22}$H$_{16}$NO$_2$FS: 377.0886. Observed: 377.0868. Analysis Calc'd. for C$_{22}$H$_{16}$NO$_2$FS: C, 70.01; H, 4.27; N, 3.71. Observed: C, 68.18; H, 4.19; N, 3.58.

Step 3

Preparation of 5-(4-Fluorophenyl)-4-[4-(methylsulfonyl)phenyl]-2-phenyloxazole

A solution containing 64 mg (0.173 mmol) of 5-(4-fluorophenyl)-4-[4-(methylthio)phenyl]-2-phenyloxazole in 10 mL of methylene chloride was stirred at −78° C. as 120 mg (0.346 mmol based on 50% purity) of m-chloroperoxybenzoic acid was added all at once. The reaction was stirred at −78° C. for 1 hour and TLC (silica, 50% hexane-ethyl acetate) indicated that the reaction mixture consisted of mostly sulfone. The reaction was poured into a solution of aqueous sodium metabisulfite. The aqueous solution was extracted using ethyl acetate and the organic layer was washed with saturated sodium metabisulfite, saturated sodium bicarbonate and brine. The resulting clear solution was dried over sodium sulfate and concentrated in vacuo to give a white solid which was purified by flash chromatography on a silica gel column using 50% ethyl acetate/hexane as the eluent. Recrystallization from 50% dichloromethane/isooctane gave 62 mg (91%) of a white crystalline solid (mp 175°–176° C.) whose structure was assigned as 5-(4-fluorophenyl)-4-[4-(methylsulfonyl)phenyl]-2-phenyl oxazole on the basis of its spectral characteristics: $^1$H-NMR (CDCl$_3$, 300 MHz) ∂ 3.13 (s, 3H), 7.19 (t, 2H, J=8.6 Hz), 7.55 (m, 3H), 7.69 (m, 2H), 8.00 (m, 2H), 8.17 (m, 2H). LRMS m/z 393 (M)+. HRMS Calc'd. for C$_{22}$H$_{16}$NO$_3$FS: 393.0835. Observed: 393.0865.

EXAMPLE 23

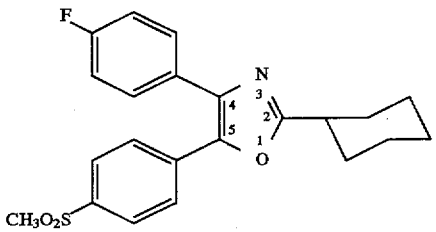

4-(4-Fluorophenyl)-2-cyclohexyl-5-[4-(methylsulfonyl)phenyl]oxazole 4-(4-Fluorophenyl)-2-cyclohexyl-5-[4-(methylsulfonyl) phenyl]oxazole was prepared in a manner analogous to Example 1. Melting point: 127°–128° C.

EXAMPLE 24

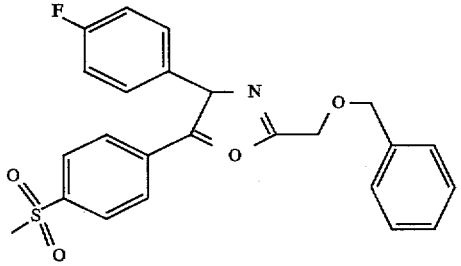

4-(4-Fluorophenyl)-2-benzyloxymethyl-5-[4-(methylsulfonyl)phenyl]oxazole

Step 1

Preparation of the benzoin ester

A solution containing 2.07 g (6.71 mmol) of 1-(4-fluorophenyl)-2-hydroxy-2-[4-(methylsulfonylphenyl) ethanone in 100 mL of methylene chloride was stirred at 25° C. as 2.71 mL (33.55 mmol) of pyridine was added, followed by the addition of 1.27 mL (8.05 mmol) of benzyloxyacetyl chloride. The reaction was stirred at 25° C. for 48 hours, after which the resulting yellow solution was washed with 1N HCl, dried over sodium sulfate and concentrated in vacuo. The oily yellow solid was purified via flash chromatography on a silica gel column using 20% ethyl acetate/ hexane as the eluent. This provided 2.22 g (73%) of a white foam, which was characterized as the benzoin ester on the basis of its NMR spectra: $^1$H-NMR (CDCl$_3$, 300 MHz) ∂3.03 (s, 3H), 4.23 (d, 1H, J=17.0 Hz), 4.33 (d, 1H, J=17.0 Hz), 4.67 (s, 2H), 6.95 (s, 1H), 7.13 (t, 2H, J=8.5 Hz), 7.35 (m, 5H), 7.66 (d, 2H, J=8.1 Hz) and 7.98 (m, 4H). $^{19}$F-NMR (CDCl$_3$, 280 MHz) ∂–102.5.

Step 2

Preparation of 2-benzyloxymethyl-4-(4-fluorophenyl)-5-[4-(methylsulfonyl)phenyl]oxazole A solution containing 2.22 g (4.86 mmol) of the benzoin ester and 3.74 g (48.6 mmol) of ammonium acetate in 100 mL of acetic acid was heated to 80° C. for 2 hours. The reaction was cooled to 25° C. and poured into water. The product was extracted into ethyl acetate and the combined organic extracts washed with an aqueous solution of sodium bicarbonate. The solution was dried over sodium sulfate and concentrated in vacuo to give a yellow oil. This crude material was purified by flash chromatography on a silica gel column using 25% ethyl acetate/hexane as the eluent to give 1.92 g (90%) of a clear oil, which was characterized as 2-benzyloxymethyl-4-(4-fluorophenyl)-5-[4-(methylsulfonyl)phenyl]oxazole on the basis of its spectral properties: $^1$H-NMR (CDCl$_3$, 300 MHz) ∂3.07 (s, 3H), 4.70 (s, 2H), 4.72 (s, 2H), 7.11 (t, 2H, J=8.8 Hz), 7.22–7.40 (m, 5H), 7.58 (m, 2H), 7.76 (d, 2H, J=8.8 Hz) and 7.91 (d, 2H, J=8.8 Hz). $^{19}$F-NMR (CDCl$_3$, 280 MHz) ∂–111.88.

EXAMPLE 25

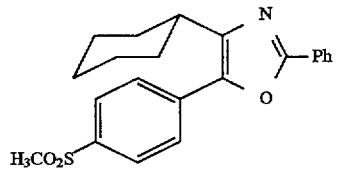

2-Phenyl-4-(cyclohexyl)-5-[4-(methylsulfonyl) phenyl]oxazole

Step 1

Preparation of 1-(cyclohexyl)-2-hydroxy-2-[4-(methylthiophenyl)ethanone

A 250 mL round bottomed flask was equipped with a mechanical stirrer and reflux condenser and charged with 30 mL of absolute ethanol, 3,4-dimethyl-5-(2-hydroxyethyl) thiazolium iodide (2.00 g, 7.0 mmol), 4-methylthiobenzaldehyde (10.66 g, 70.0 mmol), and freshly distilled cyclohexanecarboxaldehyde (7.68 g, 70.1 mmol). The solution was stirred vigorously, treated with triethylamine (4.27 g, 42.2 mmol) and heated to reflux for 24 hours. The solution was treated with additional portions of 3,4-dimethyl-5-(2-hydroxyethyl)thiazolium iodide (2.05 g, 7.01 mmol), triethylamine (4.84 g, 48.0 mmol), and cyclohexanecarboxaldehyde (7.01 g, 62.5 mmol), and heated to reflux for an additional 42 hours. The solution was concentrated in vacuo, the residue dissolved in chloroform, washed with 3N HCl, saturated aqueous sodium bicarbonate, brine, dried over anhydrous magnesium sulfate, filtered and concentrated in vacuo to afford 18.75 g, (>100%) of a yellow oil that solidified upon standing. The crude solid was purified by trituration with ether providing the desired compound in pure form 15.80 g, (86%, mp 110°–111.5° C.) which was characterized as 1-(cyclohexyl)-2-hydroxy-2-[4-(methylthiophenyl)ethanone on the basis of its NMR spectra. $^1$H-NMR (CDCl$_3$, 300 MHz) ∂1.00–1.47 (m, 6H), 1.60–1.95 (m, 4H), 2.45 (m, 1H), 2.52 (s, 3H), 4.38(d, J=3.9 Hz, 1H), 7.55 (d, J=3.9 Hz, 1H), 7.25 (m, 4H). HRMS Calc'd. for $C_{15}H_{20}NO_2S$: 264.1184. Observed: 264.1207.

Step 2

Preparation of benzoin ester

A solution containing 162 mg (0.62 mmol) of 1-(cyclohexyl)-2-hydroxy-2-[4-(methylthiophenyl)ethanone in 10 mL of methylene chloride was stirred at 25° C. as 251 µL (31 mmol) of pyridine was added, followed by the addition of 86 µL (1.24 mmol) of benzoyl chloride. The reaction was stirred at 25° C. for 48 hours, after which the resulting yellow solution was washed with 1N HCl, dried over sodium sulfate and concentrated in vacuo. The crude solid was purified via flash chromatography on a silica gel column using 10% ethyl acetate/hexane as the eluent. This provided 131 mg (57%) of a white foam, which was characterized as the benzoin ester on the basis of its NMR spectra: $^1$H-NMR (CDCl$_3$, 300 MHz) ∂1.03–1.48 (m, 6H), 1.56–1.88 (m, 3H), 2.03–2.14 (m, 1H), 2.48 (s, 3H), 2.53 (m, 1H), 6.28 (s, 1H), 7.20–7.70 (m, 5H), 8.05–8.17 (m, 4H).

Step 3

Preparation of 2-(methyl)-4-(cyclohexyl)-5-[4-(methythio)phenyl]oxazole

A solution containing 131 mg (0.355 mmol) of the benzoin ester and 273 mg (35 mmol) of ammonium acetate in 10 mL of acetic acid was heated to 80° C. for 2 hours. The reaction was cooled to 25° C. and poured into water. The product was extracted into ethyl acetate and the combined organic extracts washed with an aqueous solution of sodium bicarbonate. The solution was dried over sodium sulfate and concentrated in vacuo to give the crude oxazole. This crude material was purified crystallization from a mixture of dichloromethane and isooctane to give 89 mg, (72%, mp 151°–151.5° C.) of material, which was characterized as 2-(phenyl)-4-(cyclohexyl)-5-[4-(methythio)phenyl]oxazole on the basis of its spectral properties: $^1$H-NMR (CDCl$_3$, 300 MHz) ∂1.30–1.45 (m, 3H), 1.70–1.94 (m, 7H), 2.54 (s, 3H), 2.80–2.90 (m, 1H), 7.34 (d, J=8.5 Hz, 2H), 7.42 (m, 3H), 7.55 (d, J=8.5 Hz, 2H), 8.08 (d, J=7.7 Hz, 2H). HRMS Calc'd. for $C_{22}H_{23}NOS$ (M+H): 350.1579. Observed: 350.1597. The material from this experiment was used directly in the next step without further purification.

Step 4

Preparation of 2-phenyl-4-(cyclohexyl)-5-[4-(methylsulfonyl)phenyl]oxazole

A solution of 38 mg (0.11 mmol) of 2-phenyl-4-cyclohexyl)-5-[4-(methythio)phenyl]oxazole in 4 mL of methylene chloride was stirred at −78° C. as 75 mg (0.22 mmol based on 50% purity) of m-chloroperoxybenzoic acid was added all at once. The reaction was stirred at −78° C. for 1 hour. Thin-layer chromatography (TLC) (silica, 50% hexane/ethyl acetate) indicated the reaction mixture consisted of mostly sulfone. The reaction was poured into a solution of aqueous sodium metabisulfite. The aqueous solution was using ethyl using ethyl acetate and the organic layer was washed with saturated sodium metabisulfite, saturated sodium bicarbonate and brine. The resulting clear solution was dried over sodium sulfate and concentrated in vacuo to give a white solid which was purified by crystallization from 50% dichloromethane/isooctane gave 26 mg (62%) of pure product, whose structure was assigned as 2-phenyl-4-(cyclohexyl)-5-[4-(methylsulfonyl)phenyl]oxazole on the basis of its spectral characteristics: mp 231° C. $^1$H-NMR, (CDCl$_3$, 300 MHZ) ∂1.34–1.43 (m, 3H), 1.72–1.95 (m, 7H), 2.84 (m, 1H), 3.10 (s, 3H), 7.47 (m, 3H), 7.82 (d, J=8 Hz, 2H), 8.03 (d, J=8 Hz, 2H), 8.10 (m, 2H). LRMS m/z 382 (M)+. HRMS Calc'd. for $C_{22}H_{23}NO_3S$: 382.1477. Observed: 382.1436. Analysis Calc'd. for $C_{22}H_{23}NO_3S$: C, 69.27; H, 6.08; N, 3.67. Observed: C, 68.99; H, 6.07; N, 3.63.

EXAMPLE 26

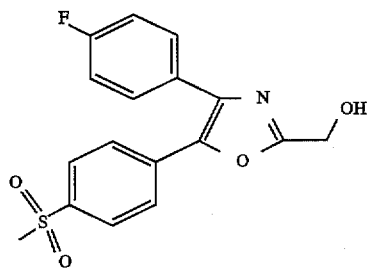

4-(4-Fluorophenyl)-2-(hydroxymethyl)-5-[4-(methylsulfonyl)phenyl]oxazole

To a solution containing 5.0 g (11.4 mmol) of 2-benzyloxymethyl-4-(4-fluorophenyl)-5-[4-(methylsulfonyl)phenyl]oxazole (prepared in Example 24) in 20 mL of 50% THF-methanol, was added 100 mg of 10% Pd on charcoal in a Fisher-Porter bottle. The reaction vessel was evacuated and then charged with hydrogen at 50 psi for 24 hours. The Pd on carbon was removed by filtration through diatomaceous earth and the filtrate concentrated in vacuo to give 3.8 g (97%) of a white crystalline solid (mp 156°–157° C.) (recrystallized from 50% ethyl acetate/isooctane) whose structure was assigned as 4-(4-fluorophenyl)-2-hydroxymethyl-5-[4-(methylsulfonyl)phenyl]oxazole on the basis of its spectral characteristics: $^1$H-NMR (CDCl$_3$, 300 MHz) ∂3.07 (s, 3H), 3.21 (bs, 1H), 4.81 (s, 2H), 7.10 (t, 2H, J=8.5 Hz), 7.56 (m, 2H), 7.72 (d, 2H, J=8.8 Hz) and 7.90 (d, 2H, J=8.8 Hz). $^{19}$F-NMR (CDCl$_3$, 280 MHz) ∂−111.5. LRMS m/z 348 (M+H)+. HRMS Calc'd. for $C_{17}H_{14}NO_4FS$: 348.0706. Observed: 348.0681. Analysis Calc'd. for $C_{17}H_{14}NO_4FS$: C:, 58.78; H, 4.06; N, 4.03. Observed: C, 58.67; H, 4.02; N, 4.01.

EXAMPLE 27

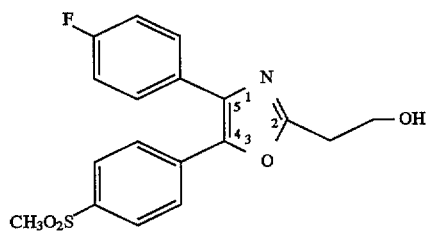

4-(4-Fluorophenyl)-2-(2-hydroxyethyl)-5-[4-(methylsulfonyl)phenyl]oxazole 4-(4-Fluorophenyl)-2-(2-hydroxyethyl)-5-[4-(methylsulfonyl)phenyl]oxazole was prepared in a manner

EXAMPLE 28

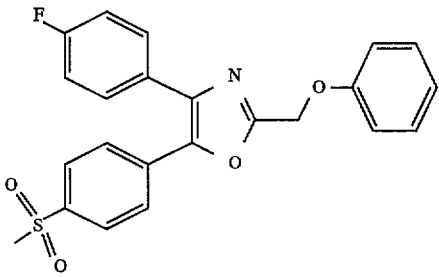

4-(4-Fluorophenyl)-5-[4-(methylsulfonyl)phenyl]-2-phenoxymethyloxazole

A solution containing 1.69 g (4.87 mmol) of 4-(4-fluorophenyl)-2-hydroxymethyl-5-[4-(methylsulfonyl)phenyl]oxazole (Example 26) in 100 mL of methylene chloride was stirred at 25° C. as 1.36 mL (9.74 mmol) of triethylamine was added dropwise, followed by the addition of 560 uL (7.30 mmol) of methanesulfonyl chloride. The reaction was stirred for 20 minutes, after which the organic solution was washed with 1N HCl, dried over sodium sulfate and concentrated in vacuo to give methyl [4-(4-fluorophenyl)-5-[4-(methylsulfonyl)phenyl]oxazol-2-yl]methanesulfonate as a yellow oil which was characterized as the expected mesylate by its NMR spectrum: $^1$H-NMR (CDCl$_3$, 400 MHz) $\partial$3.08 (s, 3H), 3.17 (s, 3H), 5.37 (s, 2H), 7.12 (t, 2H, J=8.8 Hz), 7.58 (m, 2H), 7.78 (d, 2H, J=8.8 Hz) and 7.94 (d, 2H, J=8.8 Hz). This material was used without further purification. A solution containing 544 mg (1.28 mmol) of methyl [4-(4-fluorophenyl)-5-[4-(methylsulfonyl)phenyl]oxazol-2-yl]methanesulfonate in 20 mL of DMF was stirred at 25° C. as 353 mg (2.56 mmol) of potassium carbonate and 240 mg (2.56 mmol) of phenol were added. The reaction was stirred for 2 days at 25° C. and poured into 100 mL of water. To this mixture was added 100 mL of ethyl acetate and the layers separated. The organic layer was washed with water, dried over sodium sulfate and concentrated in vacuo to give a crude beige solid which was purified by flash chromatography on a silica gel column using 25% ethyl acetate/hexane as the eluent to give 475 mg (88%) of a white solid which was recrystallized from 50% ethyl acetate/isooctane to give a white crystalline solid (mp 168°–169° C.) whose structure was assigned as 4-(4-fluorophenyl)-5-[4-(methylsulfonyl)phenyl]-2-phenoxymethyloxazole on the basis of its spectral characteristics: $^1$H-NMR (CDCl$_3$, 300 MHz) $\partial$3.07 (s, 3H), 5.23 (s, 2H), 6.98 (m, 5H), 7.33 (t, 2H, J=8.2 Hz), 7.60 (m, 2H), 7.77 (d, 2H, J=8.5 Hz) and 7.92 (d, 2H, J=8.5 Hz ). $^{19}$F-NMR (CDCl$_3$, 280 MHz ) $\partial$–111.9. Analysis calc. for C$_{23}$H$_{18}$NO$_4$FS- C: 65.24, H: 4.28, 3.31. Observed- C: 65.10, H: 4.29, N: 3.28.

EXAMPLE 29

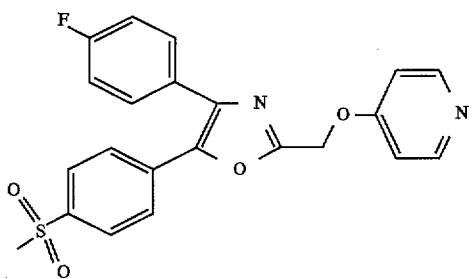

4-(4-Fluorophenyl)-2-(pyridyloxymethyl)-5-[4-(methylsulfonyl)phenyl]oxazole 4-(4-Fluorophenyl)-2-(pyridyloxymethyl)-5-[4-(methylsulfonyl)phenyl]oxazole was prepared in a manner consistent with Example 28. Melting point: 276°–278° C.

EXAMPLE 30

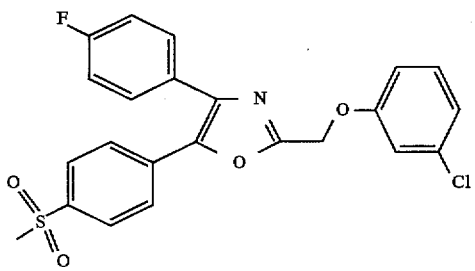

4-(4-Fluorophenyl)-2-(3-chlorophenoxymethyl)-5-[4-(methylsulfonyl)phenyl]oxazole A solution containing 612 mg (1.44 mmol) of methyl [4-(4-fluorophenyl)-5-[4-(methylsulfonyl)phenyl]oxazol-2-yl]methanesulfonate (as prepared in Example 28) in 20 mL of DMF was stirred at 25° C. as 397 mg (2.88 mmol) of potassium carbonate and 0.3 mL (2.88 mmol) of 3-chlorophenol were added. The reaction was stirred for 2 days at 25° C. and poured into 100 mL of water. To this mixture was added 100 mL of ethyl acetate and the layers separated. The organic layer was washed with water, dried over sodium sulfate and concentrated in vacuo to give the crude solid which was purified by flash chromatography on a silica gel column using 50% ethyl acetate/hexane as the eluent to give 528 mg (80%) of a white solid which was recrystallized from 50% dichloromethane/isooctane to give a white crystalline solid (mp 112°–114° C.) whose structure was assigned as 4-(4-fluorophenyl)-5-[4-(methylsulfonyl)phenyl]-2-(3-chlorophenoxy)methyloxazole on the basis of its spectral characteristics: $^1$H-NMR (CDCl$_3$, 300 MHz) $\partial$3.08 (s, 3H), 5.22 (s, 2H), 7.08 (m, 2H), 7.13 (m, 3H), 7.26 (m, 1H), 7.59 (dd, 2H, J=8.8, 5.4 Hz), 7.62 (dd, 2H, J=8.8, 5.4 Hz), 7.78 (d, 2H, J=8.8 Hz), 7.93 (d, 2H, J=8.8 Hz). $^{19}$F-NMR (CDCl$_3$, 280 MHz) $\partial$–111.8. Analysis Calc'd. for C$_{23}$H$_{17}$NO$_4$FSCl: C, 60.33; H, 3.74; N, 3.06. Observed: C, 60.19; H, 3.80; N, 3.03.

EXAMPLE 31

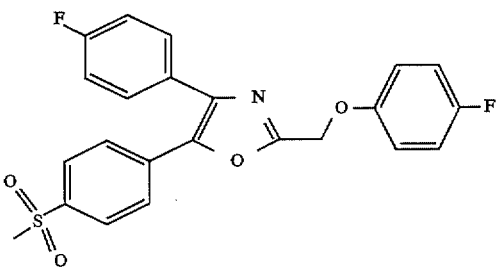

4-(4-Fluorophenyl)-2-(4-fluorophenoxymethyl)-5-[4-(methylsulfonyl)phenyl]oxazole A solution containing 585 mg (1.37 mmol) of methyl [4-(4-fluorophenyl)-5-[4-methylsulfonyl)phenyl]oxazol-2-yl]methanesulfonate (as prepared in Example 28) in 15 mL of DMF was stirred at 25° C. as 380 mg (2.74 mmol) of potassium carbonate and 308 mg (2.74 mmol) of 4-fluorophenol are added. The reaction was stirred for 2 days at 25° C. and poured into 100 mL of water. To this mixture was added 100 mL of ethyl acetate and the layers separated. The organic layer was washed with water, dried over sodium sulfate and concentrated in vacuo to give the crude solid which was purified by flash chromatography on a silica gel column using 50% ethyl acetate/hexane as the eluent to give 528 mg (80%) of a white solid which was recrystallized from 50% dichloromethane/isooctane to give a white crystalline solid (mp 133°–134° C.) whose structure was assigned as 4-(4-fluorophenyl)-5-[4-(methylsulfonyl)-phenyl]-2-[(4-fluorophenoxy)methyl]oxazole on the basis of its spectral characteristics: $^1$H-NMR (CDCl$_3$, 300 MHz) ∂3.08 (s, 3H), 5.19 (s, 2H), 7.00 (m, 4H), 7.13 (m, 2H), 7.58 (dd, 2H, J=8.8, 5.2 Hz), 7.61 (dd, 2H, J=8.8, 5.2 Hz), 7.77 (d, 2H, J=8.7 Hz), 7.93 (d, 2H, J=8.7 Hz). $^{19}$F-NMR (CDCl$_3$, 280 MHz) ∂–111.8, –122.5. Analysis Calc'd. for C$_{23}$H$_{17}$NO$_4$F$_2$S: C, 62.58; H, 3.88; N, 3.17. Observed: C, 62.44; H, 4.04; N, 3.11.

EXAMPLE 32

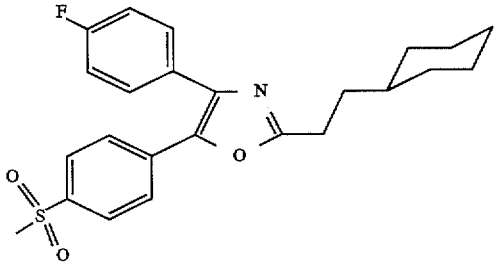

4-(4-Fluorophenyl)-2-(cyclohexylethyl)-5-[4-(methylsulfonyl)phenyl]oxazole

A solution containing 2.02 g (7.24 mmol) of 1-(4-fluorophenyl)-2-hydroxy-2-[4-(methylthiophenyl)ethanone in 100 mL of methylene chloride was stirred at 25° C. as 1.76 mL (21.72 mmol) of pyridine was added, followed by the addition of 1.52 g (8.69 mmol) of 2-cyclohexylpropionyl chloride. The reaction was stirred at 25° C. for 48 hours, after which the resulting yellow solution was washed with 1N HCl, dried over sodium sulfate and concentrated in vacuo. The crude solid was purified via flash chromatography on a silica gel column using 10% ethyl acetate/hexane as the eluent. This provided 2.87 g (96%) of a white foam, which was characterized as the benzoin ester on the basis of its NMR spectra: $^1$H-NMR (CDCl$_3$, 300 MHz) ∂ 0.80–0.96 (m, 2H), 1.10–1.25 (m, 4H), 1.45–1.78 (m, 7H), 2.40 (m, 2H), 2.43 (s, 3H), 6.75 (s, 1H), 7.05 (m, 2H), 7.23 (d, 2H, J=8 Hz), 7.35 (d, 2H, J=8 Hz) and 7.95 (m, 2H). $^{19}$F-NMR (CDCl$_3$, 280 MHz) ∂–104.4.

A solution containing 2.87 g (6.92 mmol) of the benzoin ester and 5.3 g (69 mmol) of ammonium acetate in 100 mL of acetic acid was heated to 80° C. for 2 hours. The reaction was cooled to 25° C. and poured into water. The product was extracted into ethyl acetate and the combined organic extracts washed with an aqueous solution of sodium bicarbonate. The solution was dried over sodium sulfate and concentrated in vacuo to give the crude oxazole. This crude material was purified by flash chromatography on a silica gel column using 25% ethyl acetate/hexane as the eluent to give 1.87 g (68%) of a clear oil, which was characterized as 2-(2-cyclohexylethyl)-4-(4-fluorophenyl)-5-[4-(methythio)phenyl]oxazole on the basis of its spectral properties: $^1$H-NMR (CDCl$_3$, 400 MHz) ∂ 0.90–1.02 (m, 2H), 1.10–1.40 (m, 4H), 1.62–1.82 (m, 7H), 2.49 (s, 3H), 2.84 (t, J=8.0 Hz, 2H), 7.03 (d, J=8.7 Hz, 1H), 7.06 (d, J=8.7 Hz, 1H), 7.22 (d, J=8.6 Hz, 2H), 7.45 (d, J=8.6 Hz, 2H), 7.58 (d, J=5.4 Hz, 1H), 7.61 (d, J=5.4 Hz, 1H). The material from this experiment was used directly in the next step without further purification.

A solution of 1.87 g (4.73 mmol) of 2-(2-cyclohexylethyl)-4-(4-fluorophenyl)-5-[4-(methythio)phenyl]oxazole in 100 mL of methylene chloride was stirred at –78° C. as 3.26 g (9.46 mmol based on 50% purity) of m-chloroperoxybenzoic acid was added all at once. The reaction was stirred at –78° C. for 1 hour and TLC (silica, 50% hexane/ethyl acetate) indicated that the reaction mixture consisted of mostly sulfone. The reaction was poured into a solution of aqueous sodium metabisulfite. The aqueous solution was extracted using ethyl acetate and the organic layer was washed with saturated sodium metabisulfite, saturated sodium bicarbonate and brine. The resulting clear solution was dried over sodium sulfate and concentrated in vacuo to give a white solid which was purified by flash chromatography on a silica gel column using 50% ethyl acetate/hexane as the eluent. Recrystallization from 50% ethyl acetate/isooctane gave 1.76 g (87%) of a low melting semi-solid whose structure was assigned as 2-(2-cyclohexylethyl)-4-(4-fluorophenyl)-5-[4-(methylsulfonyl)phenyl]oxazole on the basis of its spectral characteristics: $^1$H-NMR (CDCl$_3$, 300 MHz) a 0.90–1.06 (m, 2H), 1.11–1.40 (m, 7H), 2.87 (apparent t, J=8.1 Hz, 2H), 3.07 (s, 3H), 7.10 (t, J=8.7 Hz, 2H), 7.59 (m, 2H), 7.74 (d, J=8.7 Hz, 2H), 7.90 (d, J=8.7 Hz, 2H). $^{19}$F-NMR (CDCl$_3$, 280 MHz) ∂–112.49. LRMS m/z 427 (M)+. HRMS Calc'd. for C$_{24}$H$_{26}$NO$_3$FS: 421.1617. Observed: 421.1611. Analysis Calc'd. for C$_{24}$H$_{26}$NO$_3$FS: C, 67.43; H, 6.13; N, 3.28. Observed: C, 67.27; H, 6.15; N, 3.24.

EXAMPLE 33

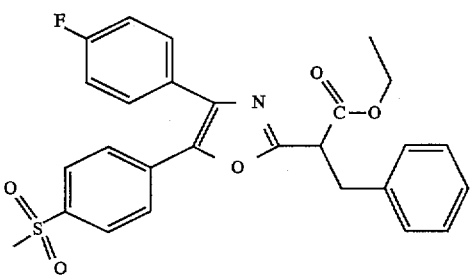

Ethyl 2-[4-(4-fluorophenyl)-5-[4-(methylsulfonyl)phenyl]oxazol-2-yl]-2-benzylacetate Step 1

Preparation of 2-(4-fluorophenyl)-3-(4-methylthiophenyl)propenoic acid

Acetic anhydride (500 mL), 4-(methylthio)benzaldehyde (100.2 g, 0.66 mol), 4-fluorophenylacetic acid (101.6 g, 0.66 mol), and triethylamine (68.1 g, 0.67 mol) were placed in a 3 L round bottom flask and heated to reflux for 1.75 hours. The reaction was cooled to 110° C., and water (500 mL) was added cautiously through an addition funnel. This caused the solution to reflux vigorously and the temperature to rise to 135° C. A yellow precipitate formed, and after cooling to room temperature, was collected by filtration, washed with water, and recrystallized from ethyl acetate/isooctane to provide the diarylacrylic acid as yellow needles (135.2 g, 71%): mp 172°–176° C. $^1$H NMR (acetone d$^6$) 300 MHz 7.84 (s, 1H), 7.03–7.28 (m, 10H), 2.46 (s, 3H). $^{19}$F NMR (acetone d$^6$) –116.11 (m). Mass spectrum M+288.

Step 2

Preparation of 1-(4-fluorophenyl)-2-(4-methylthiophenyl)ethanone

The diaryl acrylic acid (226.5 g, 0.78 mol) was placed in a 2 L round bottom flask with anhydrous toluene (800 mL) and triethylamine (81.2 g, 0.80 mol). After cooling to 0° C., diphenylphosphoryl azide (217.4 g, 0.79 mol) was added, the solution was stirred at 0° C. for 20 minutes and at room temperature for 2.50 hours. The reaction was poured into water, extracted with ether, dried over magnesium sulfate, and concentrated in vacuo to remove the ether. The remaining toluene solution was heated to reflux and a vigorous evolution of gas occurred. After 1.25 hours, tert-butyl alcohol (80 mL, 0.84 mol) was added to the reaction. After an additional 20 minutes, concentrated hydrochloric acid (41 mL) was added slowly causing the reaction to foam. The reaction was heated at 90° C. overnight (14 hours) and a white precipitate formed after cooling. The precipitate was isolated by filtration, washed with cold ether, and air dried to yield the desired intermediate (182.7 g, 89%): mp 134.5°–138° C. $^1$H NMR (acetone d$^6$) 300 MHz 8.16 (m, 2H), 7.24 (m, 6H), 4.34 (s, 2H), 2.46 (s, 3H). $^{19}$F NMR (acetone d$^6$) –107.88 (m).

Step 3

Preparation of 1-(4-fluorophenyl)-2-(4-methylthiophenyl)-2-hydroxy-ethanone

A 1 L three necked round bottomed flask equipped with reflux condenser, magnetic stir bar, thermometer adapter, and constant pressure addition funnel was charged with the intermediate from Step 2, (55.5 g, 0.21 mol), acetic acid (250 mL) and 33% HBr in acetic acid (120 mL). The solution was stirred and treated with bromine (11.1 mL, 0.21 mol) from the addition funnel at such a rate that the bromine color was discharged rapidly, ca. 15 minutes. After an additional 10 minutes at room temperature, the solution was filtered through a Buchner funnel and the filtrate concentrated in vacuo to give an orange solid. The crude bromoketone was dissolved in dichloromethane and washed with 1N NaHSO$_3$, dried over anhydrous MgSO$_4$, filtered and concentrated in vacuo to give 68.8 g of 1-(4-fluorophenyl)-2-(4-methylthiophenyl)-2-bromoethanone as a yellow solid which was used directly without further purification. The crude bromoketone was dissolved in 300 mL acetone and 150 mL of water and heated to reflux for 2.5 hours. The solution was concentrated in vacuo and the residue taken up in dichloromethane, washed with saturated aqueous sodium bicarbonate, brine, dried over anhydrous magnesium sulfate, filtered and reconcentrated in vacuo to give a light yellow solid that was crystallized from a mixture of dichloromethane and isooctane to provide 37.8 g (65%) of pure 1-(4-fluorophenyl)-2-(4-methylthiophenyl)-2-hydroxy-ethanone: mp 90°–92° C.

Step 4

Preparation of ethyl 2-[4-(4-fluorophenyl)-5-[4-methylthio)phenyl]oxazol-2-yl]acetate A solution containing 8.00 g (29 mmol) of 1-(4-fluorophenyl)-2-hydroxy-2-[4-(methylthiophenyl)ethanone in 100 mL of methylene chloride was stirred at 25° C. as 7.0 mL (31 mmol) of pyridine was added, followed by the addition of 4.5 mL (35 mmol) of ethyl malonyl chloride. The reaction was stirred at 25° C. for 48 hours, after which the resulting yellow solution was washed with 1N HCl, dried over sodium sulfate and concentrated in vacuo. The crude solid was purified via flash chromatography on a silica gel column using 10% ethyl acetate/hexane as the eluent. This provided 7.31 g (64%) of a white foam, which was used directly without further purification. The product from above (7.31 g, 18.7 mmol) and 7.2 g of ammonium acetate (93.5 mmol, 5 equivalents) in 50 mL of glacial acetic were heated to reflux for 2 hours. The reaction mixture was cooled to 25° C. and poured into 100 mL of water. The aqueous solution was extracted with ethyl acetate and the combined organic extracts were washed with water and sodium bicarbonate solution, dried over sodium sulfate and concentrated in vacuo. The crude solid was purified by flash chromatography using a silica gel column and 20% ethyl acetate/hexane as the eluent to give a white solid which was recrystallized from 50% ethyl acetate/isooctane to give 5.55 g (80%) of a white solid whose structure was assigned as ethyl 2-[4-(4-fluorophenyl)-5-[4-methylthio)phenyl]oxazol-2-yl]acetate and was judged suitable for taking onto the next step.

Step 5

Preparation of ethyl 2-[4-(4-fluorophenyl)-5-[4-methylsulfonyl)phenyl]oxazol-2-yl]-1-benzyl-acetate A solution of 755 mg (2.03 mmol) of ethyl 2-[4-(4-fluorophenyl)-5-[4-methylthio)phenyl]oxazol-2-yl]acetate (from Step 4) was dissolved in 20 mL of anhydrous tetrahydrofuran (THF) and cooled to –78° C. and treated with a solution of potassium bid(trimethylsilyl)amide (2.44 mL, 1.2 equivalents, 1M in THF via syringe. The solution was maintained at –78° C. for 15 minutes and treated with a solution of 290 uL (2.44 mmol) of benzyl bromide. The solution was warmed to room temperature and poured into a saturated aqueous solution of ammonium chloride. The aqueous solution was extracted with ethyl acetate, washed with brine, dried over anhydrous sodium sulfate, filtered and concentrated in vacuo to give an oil that was purified by flash chromatography on silica gel eluting with 10% ethyl acetate/hexane to provide 396 mg of the dialkylated product and 182 mg (19%) of ethyl 2-[4-(4-fluorophenyl)-5-[4-methylthio)phenyl]oxazol-2-yl]-1-benzyl-acetate that was used directly in the next step. A solution of 182 mg (0.344 mmol) of ethyl 2-[4-(4-fluorophenyl)-5-[4-methylthio) phenyl]oxazol-2-yl]-1-benzyl-acetate in 5 mL of dichloromethane was cooled to −78° C. and treated with 272 mg (2 equivalents) of m-chloroperoxybenzoic acid for 2 hours. The reaction was poured into a solution of aqueous sodium metabisulfite. The aqueous solution was extracted using ethyl acetate and the organic layer was washed with saturated sodium metabisulfite, saturated sodium bicarbonate and brine. The resulting clear solution was dried over sodium sulfate and concentrated in vacuo to give a transparent oil which was purified by flash chromatography on a silica gel column using 30% ethyl acetate/hexane as the eluent. The purified material was an oil whose structure was assigned as ethyl 2-[4-(4-fluorophenyl)-5-[4-methylsulfonyl)phenyl]oxazol-2-yl]-1-benzyl-acetate on the basis of its spectral characteristics: $^1$H-NMR (CDCl$_3$, 300 MHz) $\partial$1.20 (t, J=7.0 Hz, 3H), 3.07 (s, 3H), 3.53 (m, 2H), 4.19 (q, J=7.0 Hz, 2H), 4.23 (m, 1H), 7.10 (d, J=8.7 Hz, 2H), 7.25 (m, 5H), 7.57 (m, 2H), 7.70 (d, J=8.7 Hz, 2H), 7.90 (d, J=8.7 Hz, 2H). $^{19}$F-NMR (CDCl$_3$, 280 MHz) $\partial$−112.15. LRMS m/z 493 (M)+. HRMS Calc'd. for $C_{27}H_{24}NO_5FS$: 493.1359. Observed: 493.1371.

BIOLOGICAL EVALUATION

Rat Carrageenan Foot Pad Edema Test

The carrageenan foot edema test was performed with materials, reagents and procedures essentially as described by Winter, et al., (Proc, Soc. Exp. Biol. Med., 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, Laboratory Models for Testing NSAIDs, in Non-steroidal Anti-Inflammatory Drugs, (J. Lombardino, ed. 1985)). The % inhibition shows the % decrease from control paw volume determined in this procedure and the data for selected compounds in this invention are summarized in Table 1.

Rat Carrageenan-induced Analgesia Test

The analgesia test using rat carrageenan was performed with materials, reagents and procedures essentially as described by Hargreaves, et al., (Pain, 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table I.

TABLE I

| Example | RAT PAW EDEMA<br>% Inhibition<br>@ 10mg/kg body weight | ANALGESIA<br>% Inhibition<br>@20mg/kg body weight |
| --- | --- | --- |
| 1 | 41* | 44 |
| 3 | 30 | — |
| 7 | 24 | — |
| 8 | 12 | — |
| 10 | 18 | — |
| 11 | 42 | — |
| 16 | 26 | — |
| 28 | 2 | — |
| 30 | 4 | — |
| 31 | 5 | — |

*@ 20mg/kg body weight

Evaluation of COX I and COX II activity in vitro

The compounds of this invention exhibited inhibition in vitro of COX II. The COX II inhibition activity of the compounds of this invention illustrated in the Examples was determined by the following methods.

a. Preparation of recombinant COX baculoviruses

A 2.0 kb fragment containing the coding region of either human or murine COX-I or human or murine COX-II was cloned into a BamH1 site of the baculovirus transfer vector pVL1393 (Invitrogen) to generate the baculovirus transfer vectors for COX-I and COX-II in a manner similar to the method of D. R. O'Reilly et al (Baculovirus Expression Vectors: A Laboratory Manual (1992)). Recombinant baculoviruses were isolated by transfecting 4 µg of baculovirus transfer vector DNA into SF9 insect cells (2×10e8) along with 200 ng of linearized baculovirus plasmid DNA by the calcium phosphate method. See M. D. Summers and G. E. Smith, A Manual of Methods for Baculovirus Vectors and Insect Cell Culture Procedures, Texas Agric. Exp. Station Bull. 1555 (1987). Recombinant viruses were purified by three rounds of plaque purification and high titer (10E7–10E8 pfu/ml) stocks of virus were prepared. For large scale production, SF9 insect cells were infected in 10 liter fermentors (0.5×10$^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000×G for 30 minutes, and the resultant supernatant was stored at −80° C. before being assayed for COX activity.

b. Assay for COX I and COX II activity

COX activity was assayed as PGE$_2$ formed/µg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 µM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 μl of reaction mix into 160 μl ELISA buffer and 25 μM indomethacin. The PGE$_2$ formed was measured by standard ELISA technology (Cayman Chemical). Results are shown in Table II.

TABLE II

| Example | COX I ID$_{50}$ μM | COX II ID$_{50}$ μM |
|---|---|---|
| 1 | 6.9 | .02 |
| 3 | >10 | .04 |
| 14 | >30 | >10 |
| 15 | >30 | .2 |
| 25 | >10 | .5 |
| 28 | >100 | .02 |
| 29 | >100 | 100 |
| 30 | >100 | .02 |
| 31 | >100 | .025 |
| 32 | 15.9 | .01 |
| 33 | 3.1 | .05 |

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 1000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably from about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

While the compounds of the invention can be administered as the sole active pharmaceutical agent, they can also be used in combination with one or more immunomodulators, antiviral agents or other antiinfective agents. For example, the compounds of the invention can be administered in combination with antihistamines or with other such agents known heretofore to be effective in combination with antiinflammatory agents. When administered as a combination, the therapeutic agents can be formulated as separate compositions which are given at the same time or different times, or the therapeutic agents can be given as a single composition.

The examples herein can be repeated with similar success by substituting the generically or specifically described reactants and/or operating conditions of this invention for those used in the preceding examples.

The foregoing is merely illustrative of the invention and is not intended to limit the invention to the disclosed compounds. Variations and changes which are obvious to one skilled in the art are intended to be with in the scope and nature of the invention which are defined in the appended claims. Although this invention has been described with respect to specific embodiments, the details of these embodiments are not to be construed as limitations.

What is claimed is:

1. A compound of Formula I

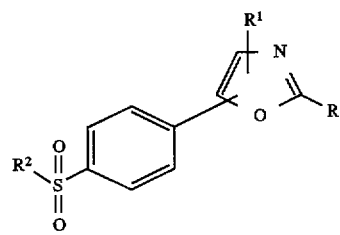

wherein R is selected from hydrido, alkyl, hydroxyalkyl, haloalkyl, alkenyl, hydroxyalkenyl, alkynyl, hydroxyalkynyl, cycloalkyl, cycloalkylalkyl, aryl optionally substituted at a substitutable position by carboxy, alkyl, alkoxy and halo, heteroaryl optionally substituted at a substitutable position by carboxy, alkyl, alkoxy and halo, aralkyl optionally substituted at a substitutable position on the aryl group by carboxy, alkyl, alkoxy and halo, aryloxyalkyl optionally substituted at a substitutable position with halo, carboxy, alkyl and alkoxy, aralkoxyalkyl optionally substituted at a substitutable position with halo, carboxy, alkyl and alkoxy, heteroaryloxyalkyl optionally substituted at a substitutable position with halo, carboxy, alkyl and alkoxy, alkoxycarbonyl, alkoxycarbonylalkyl, carboxy, carboxyalkyl, arylthioalkyl, aminocarbonylalkyl, N-alkylaminocarbonylalkyl and N,N-dialkylaminocarbonylalkyl;
wherein $R^1$ is selected from cycloalkyl, cycloalkenyl, aryl and heteroaryl, wherein $R^1$ is optionally substituted at a substitutable position by alkyl, alkoxy and halo; and wherein $R^2$ is selected from alkyl, haloalkyl and amino; or a pharmaceutically-acceptable salt thereof; provided R is not methyl when $R^2$ is amino; further provided R is not alkyl, phenyl, aralkyl, carboxyalkyl or alkoxycarbonylalkyl, when $R^1$ is 4-fluorophenyl and when $R^2$ is methyl; and further provided that $R^1$ is not phenyl when $R^2$ is methyl and R is isopropyl or tert-butyl.

2. Compound of claim 1 wherein R is selected from hydrido, lower alkyl, lower hydroxyalkyl, lower haloalkyl, lower alkenyl, lower hydroxyalkenyl, lower alkynyl, lower hydroxyalkynyl, lower cycloalkyl, lower cycloalkylalkyl, aryl selected from phenyl and naphthyl, optionally substituted at a substitutable position by halo, carboxy, lower alkyl and lower alkoxy, heteroaryl selected from pyridyl, thienyl, thiazolyl, oxazolyl, imidazolyl, furyl and quinolyl, optionally substituted at a substitutable position by halo, carboxy, lower alkyl and lower alkoxy, lower aralkyl optionally substituted at a substitutable position on the aryl group by halo, carboxy, lower alkyl and lower alkoxy, lower aryloxyalkyl optionally substituted at a substitutable position with halo, carboxy, lower alkyl and lower alkoxy, lower heteroaryloxyalkyl optionally substituted at a substitutable position with halo, carboxy, lower alkyl and lower alkoxy, lower aralkoxyalkyl optionally substituted at a substitutable position with halo, carboxy, lower alkyl and lower alkoxy, lower alkoxycarbonyl, lower alkoxycarbonylalkyl, carboxy, lower carboxyalkyl, lower arylthioalkyl, lower aminocarbonylalkyl, lower N-alkylaminocarbonylalkyl and lower N,N-dialkylaminocarbonylalkyl; wherein $R^1$ is selected from lower cycloalkyl, lower cycloalkenyl, phenyl, naphthyl and heteroaryl selected from pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by lower alkyl, lower alkoxy and halo; and wherein $R^2$ is methyl or amino; or a pharmaceutically-acceptable salt thereof.

3. Compound of claim 2 wherein R is selected from hydrido, methyl, ethyl, n-propyl, isopropyl, butyl, tert-butyl, isobutyl, hydroxymethyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, ethenyl, 1-propenyl, 2-propenyl, 1-butenyl, 2-butenyl, 3-butenyl, hydroxyethenyl, ethynyl, 1-propynyl, 2-propynyl, 1-butynyl, 2-butynyl, 3-butynyl, hydroxyethynyl, cyclobutyl, cyclopentyl, cyclohexyl, cycloheptyl, cyclobutylmethyl, cyclopentylmethyl, cyclohexylmethyl, cyclohexylethyl, cyclohexylpropyl, cycloheptylmethyl, phenyl and naphthyl, optionally substituted at a substitutable position by fluoro, chloro, bromo, iodo, carboxy, methyl, ethyl, n-propyl, isopropyl, butyl, tert-butyl, isobutyl, methoxy, ethoxy, propoxy and butoxy, pyridyl, thienyl, thiazolyl, oxazolyl, imidazolyl, furyl and quinolyl, optionally substituted at a substitutable position by fluoro, chloro, bromo, iodo, carboxy, methyl, ethyl, n-propyl, isopropyl, butyl, tert-butyl, isobutyl, methoxy, ethoxy, propoxy and butoxy, benzyl, phenethyl, diphenylmethyl and phenpropyl, optionally substituted at a substitutable position on the phenyl group by fluoro, chloro, bromo, iodo, carboxy, methyl, ethyl, n-propyl, isopropyl, butyl, tert-butyl, isobutyl, methoxy, ethoxy, propoxy and butoxy, phenoxymethyl optionally substituted at a substitutable position on the phenyl group with fluoro, chloro, bromo, iodo, carboxy, methyl, ethyl, n-propyl, isopropyl, butyl, tert-butyl, isobutyl, methoxy, ethoxy, propoxy and butoxy, benzyloxymethyl optionally substituted at a substitutable position on the phenyl group with fluoro, chloro, bromo, iodo, carboxy, methyl, ethyl, n-propyl, isopropyl, butyl, tert-butyl, isobutyl, methoxy, ethoxy, propoxy and butoxy, pyridyloxymethyl and quinolyloxymethyl optionally substituted at a substitutable position with fluoro, chloro, bromo, iodo, carboxy, methyl, ethyl, n-propyl, isopropyl, butyl, tert-butyl, isobutyl, methoxy, ethoxy, propoxy and butoxy, methoxycarbonyl, ethoxycarbonyl, propoxycarbonyl, butoxycarbonyl, methoxycarbonylmethyl, ethoxycarbonylmethyl, methoxycarbonylethyl, ethoxycarbonylethyl, carboxy, acetyl, propanoic, butanoic, pentanoic, hexanoic, phenylthiomethyl, aminocarbonylmethyl, N-methylaminocarbonylmethyl and N,N-dimethylaminocarbonylmethyl; wherein $R^1$ is selected from cyclobutyl, cyclopentyl, cyclohexyl, cycloheptyl, 1-cyclohexenyl, 2-cyclohexenyl, 3-cyclohexenyl, cyclopentenyl, cycloheptenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by methyl, ethyl, n-propyl, isopropyl, butyl, tert-butyl, isobutyl, methoxy, ethoxy, propoxy, butoxy, fluoro, chloro, bromo and iodo; and wherein $R^2$ is methyl, or amino; or a pharmaceutically-acceptable salt thereof.

4. Compound of claim 3 selected from compounds and their pharmaceutically-acceptable salts, of the group consisting of
4-[2-benzyl-5-(phenyl)oxazol-4-yl]benzenesulfonamide;
4-[2-benzyl-5-(4-fluorophenyl)oxazol-4-yl]benzenesulfonamide;
4-[2-benzyl-5-(3,4-difluorophenyl)oxazol-4-yl]benzenesulfonamide;
4-[2-benzyl-5-(4-chlorophenyl)oxazol-4-yl]benzenesulfonamide;
4-[2-benzyl-5-(3,4-dichlorophenyl)oxazol-4-yl]benzenesulfonamide;
4-[2-benzyl-5-(4-methoxyphenyl)oxazol-4-yl]benzenesulfonamide;
4-[2-benzyl-5-(3,4-dimethoxyphenyl)oxazol-4-yl]benzenesulfonamide;
4-[2-benzyl-5-(4-methylphenyl)oxazol-4-yl]benzenesulfonamide;
4-[2-benzyl-5-(3,4-dimethylphenyl)oxazol-4-yl]benzenesulfonamide;
4-[2-benzyl-5-(3-chloro-4-methylphenyl)oxazol-4-yl]benzenesulfonamide;
4-[2-benzyl-5-(4-chloro-3-methylphenyl)oxazol-4-yl]benzenesulfonamide;
4-[2-benzyl-5-(3-chloro-4-methoxyphenyl)oxazol-4-yl]benzenesulfonamide;
4-[2-benzyl-5-(4-chloro-3-methoxyphenyl)oxazol-4-yl]benzenesulfonamide;
4-[2-benzyl-5-(3,5-dichloro-4-methoxyphenyl)oxazol-4-yl]benzenesulfonamide;
4-[2-benzyl-5-(3-fluoro-4-methylphenyl)oxazol-4-yl]benzenesulfonamide;
4-[2-benzyl-5-(4-fluoro-3-methylphenyl)oxazol-4-yl]benzenesulfonamide;

4-[2-benzyl-5-(3-fluoro-4-methoxyphenyl)oxazol-4-yl]benzenesulfonamide;
4-[2-benzyl-5-(2-thienyl)oxazol-4-yl]benzenesulfonamide;
4-[2-benzyl-5-(5-chloro-2-thienyl)oxazol-4-yl]benzenesulfonamide;
4-[2-benzyl-5-(cyclohexyl)oxazol-4-yl]benzenesulfonamide;
4-[2-benzyl-5-(1-cyclohexenyl)oxazol-4-yl]benzenesulfonamide;
2-benzyl-4-(4-methylsulfonylphenyl-5-phenyloxazole;
2-benzyl-4-(4-methylsulfonylphenyl-5-(3,4-difluorophenyl)oxazole;
2-benzyl-4-(4-methylsulfonylphenyl-5-(4-chlorophenyl)oxazole;
2-benzyl-4-(4-methylsulfonylphenyl-5-(3,4-dichlorophenyl)oxazole;
2-benzyl-4-(4-methylsulfonylphenyl-5-(4-methoxyphenyl)oxazole;
2-benzyl-4-(4-methylsulfonylphenyl-5-(3,4-dimethoxyphenyl)oxazole;
2-benzyl-4-(4-methylsulfonylphenyl)-5-(4-methylphenyl)oxazole;
2-benzyl-4-(4-methylsulfonylphenyl)-5-(3,4-dimethylphenyl)oxazole;
2-benzyl-4-(4-methylsulfonylphenyl)-5-(3-chloro-4-methylphenyl)oxazole;
2-benzyl-4-(4-methylsulfonylphenyl)-5-(4-chloro-3-methylphenyl)oxazole;
2-benzyl-4-(4-methylsulfonylphenyl)-5-(3-chloro-4-methoxyphenyl)oxazole;
2-benzyl-4-(4-methylsulfonylphenyl)-5-(4-chloro-3-methoxyphenyl)oxazole;
2-benzyl-4-(4-methylsulfonylphenyl)-5-(3,5-dichloro-4-methoxyphenyl)oxazole;
2-benzyl-4-(4-methylsulfonylphenyl)-5-(3-fluoro-4-methylphenyl)oxazole;
2-benzyl-4-(4-methylsulfonylphenyl)-5-(4-fluoro-3-methylphenyl)oxazole;
2-benzyl-4-(4-methylsulfonylphenyl)-5-(3-fluoro-4-methoxyphenyl)oxazole;
2-benzyl-4-(4-methylsulfonylphenyl)-5-(2-thienyl)oxazole;
2-benzyl-4-(4-methylsulfonylphenyl)-5-(5-chloro-2-thienyl)oxazole;
2-benzyl-4-(4-methylsulfonylphenyl)-5-(cyclohexyl)oxazole-;
2-benzyl-4-(4-methylsulfonylphenyl)-5-(1-cyclohexenyl)oxazole;
2-(ethyl)-4-(4-methylsulfonylphenyl)-5-phenyloxazole;
2-(trifluoromethyl)-4-(4-methylsulfonylphenyl)-5-phenyloxazole;
2-(difluoromethyl)-4-(4-methylsulfonylphenyl)-5-phenyloxazole;
2-(hydroxymethyl)-4-(4-methylsulfonylphenyl)-5-phenyloxazole;
2-(carboxy)-4-(4-methylsulfonylphenyl)-5-phenyloxazole;
2-(methoxycarbonyl)-4-(4-methylsulfonylphenyl-5-phenyloxazole;
2-(ethoxycarbonyl)-4-(4-methylsulfonylphenyl)-5-phenyloxazole;
2-(propyl)-4-(4-methylsulfonylphenyl)-5-phenyloxazole;
2-(benzyl)-4-(4-methylsulfonylphenyl)-5-phenyloxazole;
2-(phenoxymethyl)-4-(4-methylsulfonylphenyl)-5-phenyloxazole;
2-((4-chlorophenoxy)methyl)-4-(4-methylsulfonylphenyl)-5-phenyloxazole;
2-((4-fluorophenoxy)methyl)-4-(4-methylsulfonylphenyl)-5-phenyloxazole;
2-((4-carboxyphenoxy)methyl)-4-(4-methylsulfonylphenyl)-5-phenyloxazole;
2-(2-phenethyl)-4-(4-methylsulfonylphenyl)-5-phenyloxazole;
2-(3-phenpropyl)-4-(4-methylsulfonylphenyl)-5-phenyloxazole;
2-(carboxymethyl)-4-(4-methylsulfonylphenyl)-5-phenyloxazole;
2-(ethoxycarbonylmethyl)-4-(4-methylsulfonylphenyl)-5-phenyloxazole;
2-(methoxycarbonylmethyl)-4-(4-methylsulfonylphenyl)-5-phenyloxazole;
2-(2-quinolyloxymethyl)-4-(4-methylsulfonylphenyl)-5-phenyloxazole;
4-[2-(ethyl)-5-phenyloxazol-4-yl]benzenesulfonamide;
4-[2-(trifluoromethyl)-5-phenyloxazol-4-yl]benzenesulfonamide;
4-[2-(difluoromethyl)-5-phenyloxazol-4-yl]benzenesulfonamide;
4-[2-(hydroxymethyl)-5-phenyloxazol-4-yl]benzenesulfonamide;
4-[2-(carboxy)-5-phenyloxazol-4-yl]benzenesulfonamide;
4-[2-(methoxycarbonyl)-5-phenyloxazol-4-yl]benzenesulfonamide;
4-[2-(ethoxycarbonyl)-5-phenyloxazol-4-yl]benzenesulfonamide;
4-[2-(propyl)-5-phenyloxazol-4-yl]benzenesulfonamide;
4-[2-(benzyl)-5-phenyloxazol-4-yl]benzenesulfonamide;
4-[2-(phenoxymethyl)-5-phenyloxazol-4-yl]benzenesulfonamide;
4-[2-((4-chlorophenoxy)methyl)-5-phenyloxazol-4-yl]benzenesulfonamide;
4-[2-((4-fluorophenoxy)methyl)-5-phenyloxazol-4-yl]benzenesulfonamide;
4-[2-((4-carboxyphenoxy)methyl)-5-phenyloxazol-4-yl]benzenesulfonamide;
4-[2-(2-phenethyl)-5-phenyloxazol-4-yl]benzenesulfonamide;
4-[2-(3-phenpropyl)-5-phenyloxazol-4-yl]benzenesulfonamide;
4-[2-(carboxymethyl)-5-phenyloxazol-4-yl]benzenesulfonamide;
4-[2-(ethoxycarbonylmethyl)-5-phenyloxazol-4-yl]benzenesulfonamide;
4-[2-(methoxycarbonylmethyl)-5-phenyloxazol-4-yl]benzenesulfonamide;
4-[2-(2-quinolyloxymethyl)-5-phenyloxazol-4-yl]benzenesulfonamide;
4-[2-benzyl-4-phenyloxazol-5-yl]benzenesulfonamide;
4-[2-benzyl-4-(4-fluorophenyl)oxazol-5-yl]benzenesulfonamide;
4-[2-benzyl-4-(3,4-difluorophenyl)oxazol-5-yl]benzenesulfonamide;
4-[2-benzyl-4-(4-chlorophenyl)oxazol-5-yl]benzenesulfonamide;
4-[2-benzyl-4-(3,4-dichlorophenyl)oxazol-5-yl]benzenesulfonamide;
4-[2-benzyl-4-(4-methoxyphenyl)oxazol-5-yl]benzenesulfonamide;
4-[2-benzyl-4-(3,4-dimethoxyphenyl)oxazol-5-yl]benzenesulfonamide;
4-[2-benzyl-4-(4-methylphenyl)oxazol-5-yl]benzenesulfonamide;
4-[2-benzyl-4-(3,4-dimethylphenyl)oxazol-5-yl]benzenesulfonamide;
4-[2-benzyl-4-(3-chloro-4-methylphenyl)oxazol-5-yl]benzenesulfonamide;

4-[2-benzyl-4-(4-chloro-3-methylphenyl)oxazol-5-yl]benzenesulfonamide;
4-[2-benzyl-4-(3-chloro-4-methoxyphenyl)oxazol-5-yl]benzenesulfonamide;
4-[2-benzyl-4-(4-chloro-3-methoxyphenyl)oxazol-5-yl]benzenesulfonamide;
4-[2-benzyl-4-(3,5-dichloro-4-methoxyphenyl)oxazol-5-yl]benzenesulfonamide;
4-[2-benzyl-4-(3-fluoro-4-methylphenyl)oxazol-5-yl]benzenesulfonamide;
4-[2-benzyl-4-(4-fluoro-3-methylphenyl)oxazol-5-yl]benzenesulfonamide;
4-[2-benzyl-4-(3-fluoro-4-methoxyphenyl)oxazol-5-yl]benzenesulfonamide;
4-[2-benzyl-4-(2-thienyl)oxazol-5-yl]benzenesulfonamide;
4-[2-benzyl-4-(5-chloro-2-thienyl)oxazol-5-yl]benzenesulfonamide;
4-[2-benzyl-4-(cyclohexyl)oxazol-5-yl]benzenesulfonamide;
4-[2-benzyl-4-(1-cyclohexenyl)oxazol-5-yl]benzenesulfonamide;
2-benzyl-5-(4-methylsulfonylphenyl)-4-phenyloxazole;
2-benzyl-5-(4-methylsulfonylphenyl)-4-(3,4-difluorophenyl)oxazole;
2-benzyl-5-(4-methylsulfonylphenyl)-4-(4-chlorophenyl)oxazol-4-yl]benzenesulfonamide;
2-benzyl-5-(4-methylsulfonylphenyl)-4-(3,4-dichlorophenyl)oxazole;
2-benzyl-5-(4-methylsulfonylphenyl)-4-(4-methoxyphenyl)oxazole;
2-benzyl-5-(4-methylsulfonylphenyl)-4-(3,4-dimethoxyphenyl)oxazole;
2-benzyl-5-(4-methylsulfonylphenyl)-4-(4-methylphenyl)oxazole;
2-benzyl-5-(4-methylsulfonylphenyl)-4-(3,4-dimethylphenyl)oxazole;
2-benzyl-5-(4-methylsulfonylphenyl)-4-(3-chloro-4-methylphenyl)oxazole;
2-benzyl-5-(4-methylsulfonylphenyl)-4-(4-chloro-3-methylphenyl)oxazole;
2-benzyl-5-(4-methylsulfonylphenyl)-4-(3-chloro-4-methoxyphenyl)oxazole;
2-benzyl-5-(4-methylsulfonylphenyl)-4-(4-chloro-3-methoxyphenyl)oxazole;
2-benzyl-5-(4-methylsulfonylphenyl)-4-(3,5-dichloro-4-methoxyphenyl)oxazole;
2-benzyl-5-(4-methylsulfonylphenyl)-4-(3-fluoro-4-methylphenyl)oxazole;
2-benzyl-5-(4-methylsulfonylphenyl)-4-(4-fluoro-3-methylphenyl)oxazole;
2-benzyl-5-(4-methylsulfonylphenyl)-4-(3-fluoro-4-methoxyphenyl)oxazole;
2-benzyl-5-(4-methylsulfonylphenyl)-4-(2-thienyl)oxazole;
2-benzyl-5-(4-methylsulfonylphenyl)-4-(5-chloro-2-thienyl)oxazole;
2-benzyl-5-(4-methylsulfonylphenyl)-4-(cyclohexyl)oxazole-;
2-benzyl-5-(4-methylsulfonylphenyl)-4-(2-cyclohexenyl)oxazole;
2-(ethyl)-5-(4-methylsulfonylphenyl)-4-phenyloxazole;
2-(trifluoromethyl)-5-(4-methylsulfonylphenyl)-4-phenyloxazole;
2-(difluoromethyl)-5-(4-methylsulfonylphenyl)-4-phenyloxazole;
2-(hydroxymethyl)-5-(4-methylsulfonylphenyl)-4-phenyloxazole;
2-(carboxy)-5-(4-methylsulfonylphenyl)-4-phenyloxazole;
2-(methoxycarbonyl)-5-(4-methylsulfonylphenyl)-4-phenyloxazole;
2-(ethoxycarbonyl)-5-(4-methylsulfonylphenyl)-4-phenyloxazole;
2-(propyl)-5-(4-methylsulfonylphenyl)-4-phenyloxazole;
2-(benzyl)-5-(4-methylsulfonylphenyl)-4-phenyloxazole;
2-(phenoxymethyl)-5-(4-methylsulfonylphenyl)-4-phenyloxazole;
2-((4-chlorophenoxy)methyl)-5-(4-methylsulfonylphenyl)-4-phenyloxazole;
2-((4-fluorophenoxy)methyl)-5-(4-methylsulfonylphenyl)-4-phenyloxazole;
2-((4-carboxyphenoxy)methyl)-5-(4-methylsulfonylphenyl)-4-phenyloxazole;
2-(2-phenethyl)-5-(4-methylsulfonylphenyl)-4-phenyloxazole;
2-(3-phenpropyl)-5-(4-methylsulfonylphenyl)-4-phenyloxazole;
2-(carboxymethyl)-5-(4-methylsulfonylphenyl)-4-phenyloxazole;
2-(ethoxycarbonylmethyl)-5-(4-methylsulfonylphenyl)-4-phenyloxazole;
2-(methoxycarbonylmethyl)-5-(4-methylsulfonylphenyl)-4-phenyloxazole;
2-(2-quinolyloxymethyl)-5-(4-methylsulfonylphenyl)-4-phenyloxazole;
4-[2-(ethyl)-4-phenyloxazol-5-yl]benzenesulfonamide;
4-[2-(trifluoromethyl)-4-phenyloxazol-5-yl]benzenesulfonamide;
4-[2-(difluoromethyl)-4-phenyloxazol-5-yl]benzenesulfonamide;
4-[2-(hydroxymethyl)-4-phenyloxazol-5-yl]benzenesulfonamide;
4-[2-(carboxy)-4-phenyloxazol-5-yl]benzenesulfonamide;
4-[2-(methoxycarbonyl)-4-phenyloxazol-5-yl]benzenesulfonamide;
4-[2-(ethoxycarbonyl)-4-phenyloxazol-5-yl]benzenesulfonamide;
4-[2-(propyl)-4-phenyloxazol-5-yl]benzenesulfonamide;
4-[2-(benzyl)-4-phenyloxazol-5-yl]benzenesulfonamide;
4-[2-(phenoxymethyl)-4-phenyloxazol-5-yl]benzenesulfonamide;
4-[2-((4-chlorophenoxy)methyl)-4-phenyloxazol-5-yl]benzenesulfonamide;
4-[2-((4-fluorophenoxy)methyl)-4-phenyloxazol-5-yl]benzenesulfonamide;
4-[2-((4-carboxyphenoxy)methyl)-4-phenyloxazol-5-yl]benzenesulfonamide;
4-[2-(2-phenethyl)-4-phenyloxazol-5-yl]benzenesulfonamide;
4-[2-(3-phenpropyl)-4-phenyloxazol-5-yl]benzenesulfonamide;
4-[2-(carboxymethyl)-4-phenyloxazol-5-yl]benzenesulfonamide;
4-[2-(ethoxycarbonylmethyl)-4-phenyloxazol-5-yl]benzenesulfonamide;
4-[2-(methoxycarbonylmethyl)-4-phenyloxazol-5-yl]benzenesulfonamide;
4-[2-(2-quinolyloxymethyl)-4-phenyloxazol-5-yl]benzenesulfonamide;
5-(4-fluorophenyl)-2-methyl-4-[4-(methylsulfonyl)phenyl]oxazole;
3-[5-(4-fluorophenyl)-4-[4-(methylsulfonyl)phenyl]oxazol-2-yl]propanoic acid;
methyl 3-[5-(4-fluorophenyl)-4-[4-(methylsulfonyl)phenyl]oxazol-2-yl]propanate;
4-(4-fluorophenyl)-2-(2-phenyl)ethyl-5-(4-(methylsulfonyl)phenyl)oxazole;

4-(4-fluorophenyl)-2-methyl-5-[4-(methylsulfonylphenyl]
oxazole;

4-(4-fluorophenyl)-5-[4-(methylsulfonyl)phenyl]-2-
phenyloxazole;

2-benzyl-4-(4-fluorophenyl)-5-(4-(methylsulfonyl)phenyl)
oxazole;

4-(4-fluorophenyl)-5-[4-methylsulfonylphenyl]-2-(3-
phenyl)propyloxazole;

4-(4-fluorophenyl)-5-[4-methylsulfonylphenyl]-2-
propyloxazole;

2-(tert-butyl)-4-(4-fluorophenyl)-5-[4-
methylsulfonylphenyl]oxazole;

4-(4-fluorophenyl)-2-(4-methoxyphenyl)methyl-5-[4-
methylsulfonylphenyl]oxazole 4-(4-fluorophenyl)-2-(3-methoxyphenyl)methyl-5-[4-
methylsulfonylphenyl]oxazole;

2-diphenylmethyl-4-(4-fluorophenyl)-5-[4-
methylsulfonylphenyl]oxazole;

2-[4-(4-fluorophenyl)-5-[4-methylsulfonylphenyl]oxazol-2-
yl]acetic acid;

ethyl 2-[4-(4-fluorophenyl)-5-[4-methylsulfonyl)phenyl]
oxazol-2-yl]acetate;

3-[4-(4-fluorophenyl)-5-[4-methylsulfonyl)phenyl]oxazol-
2-yl]propanoic acid;

methyl 3-[4-(4-fluorophenyl)-5-[4-methylsulfonyl)phenyl]
oxazol-2-yl]propanate;

4-[4-(4-fluorophenyl)-5-[4-methylsulfonyl)phenyl]oxazol-
2-yl]butanoic acid;

methyl 4-[4-(4-fluorophenyl)-5-[4-methylsulfonyl)phenyl]
oxazol-2-yl]butanate;

3-[4-(4-fluorophenyl)-5-[4-methylsulfonyl)phenyl]oxazol-
2-yl]propanamide;

ethyl 2-[4-(4-fluorophenyl)-5-[4-(methylsulfonyl)phenyl]
oxazol-2-yl]-2-benzyl-acetate;

4-(4-fluorophenyl-2-(cyclohexylethyl)-5-[4-
(methylsulfonyl)phenyl]oxazole;

4-(4-fluorophenyl-2-(3-fluorophenoxymethyl)-5-[4-
(methylsulfonyl)phenyl]oxazole;

4-(4-fluorophenyl-2-(3-chlorophenoxymethyl)-5-[4-
(methylsulfonyl)phenyl]oxazole;

4-(4-fluorophenyl-2-(pyridyloxymethyl)-5-[4-
(methylsulfonyl)phenyl]oxazole;

4-(4-fluorophenyl-5-[4-(methylsulfonyl)phenyl]-2-
phenoxymethyloxazole;

4-(4-fluorophenyl-2-(2-hydroxyethyl)-5-[4-
(methylsulfonyl)phenyl]oxazole;

4-(4-fluorophenyl-2-(hydroxymethyl)-5-[4-
(methylsulfonyl)phenyl]oxazole;

4-(cyclohexyl)-2-phenyl-5-[4-(methylsulfonyl)phenyl]
oxazole;

4-(4-fluorophenyl)-2-benzyloxymethyl-5-[4-
(methylsulfonyl)phenyl]oxazole;

4-(4-fluorophenyl)-2-cyclohexyl-5-[4-(methylsulfonyl)
phenyl]oxazole; and 5-(4-fluorophenyl)-2-phenyl-4-[4-(methylsulfonyl)phenyl]
oxazole.

5. Compound of claim 1 wherein R is selected from alkyl, hydroxyalkyl, haloalkyl, cycloalkyl, cycloalkylalkyl, aryl optionally substituted at a substitutable position by carboxy, alkyl, alkoxy and halo, aralkyl optionally substituted at a substitutable position on the aryl group by carboxy, alkyl, alkoxy and halo, aryloxyalkyl optionally substituted at a substitutable position on the aryl group with halo, carboxy, alkyl and alkoxy, aralkoxyalkyl optionally substituted at a substitutable position by alkyl, carboxy, alkoxy and halo, heteroaryloxyalkyl optionally substituted at a substitutable position on the heteroaryl group with halo, carboxy, alkyl and alkoxy, alkoxycarbonylalkyl, carboxyalkyl and aminocarbonylalkyl; wherein $R^1$ is selected from cycloalkyl, cycloalkenyl, heteroaryl and aryl optionally substituted at a substitutable position by alkyl, alkoxy and halo; and wherein $R^2$ is methyl; or a pharmaceutically-acceptable salt thereof; provided $R^1$ is not phenyl when R is isopropyl or tert-butyl.

6. Compound of claim 5 wherein R is selected from lower alkyl, lower hydroxyalkyl, lower haloalkyl, lower cycloalkyl, lower cycloalkylalkyl, aryl selected from phenyl and naphthyl, optionally substituted at a substitutable position by halo, carboxy, lower alkyl and lower alkoxy, lower aralkyl optionally substituted at a substitutable position on the aryl radical by halo, carboxy, lower alkyl and lower alkoxy, lower aryloxyalkyl optionally substituted at a substitutable position on the aryl group with halo, carboxy, lower alkyl and lower alkoxy, aralkoxyalkyl optionally substituted at a substitutable position by halo, carboxy, lower alkyl and lower alkoxy, lower heteroaryloxyalkyl optionally substituted at a substitutable position on the heteroaryl group with halo, carboxy, lower alkyl and lower alkoxy, lower alkoxycarbonylalkyl, lower carboxyalkyl and lower aminocarbonylalkyl; and wherein $R^1$ is selected from lower cycloalkyl, lower cycloalkenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by lower alkyl, lower alkoxy and halo; or a pharmaceutically-acceptable salt thereof.

7. Compound of claim 6 wherein R is selected from methyl, ethyl, n-propyl, isopropyl, butyl, tert-butyl, isobutyl, hydroxymethyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyclobutyl, cyclopentyl, cyclohexyl, cycloheptyl, cyclobutylmethyl, cyclopentylmethyl, cyclohexylmethyl, cyclohexylethyl, cyclohexylpropyl, cycloheptylmethyl, aryl selected from phenyl and naphthyl, optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, benzyl, phenethyl, diphenylmethyl and phenpropyl, optionally substituted at a substitutable position on the phenyl group by fluoro, chloro, bromo, iodo, methyl, ethyl, n-propyl, isopropyl, butyl, tert-butyl, isobutyl, carboxy, methoxy, ethoxy, propoxy and butoxy, phenoxymethyl optionally substituted at a substitutable position with fluoro, chloro, bromo, iodo, methyl, ethyl, n-propyl, isopropyl, butyl, tert-butyl, isobutyl, carboxy, methoxy, ethoxy, propoxy and butoxy, benzyloxymethyl optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, pyridyloxymethyl and quinolyloxymethyl, optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, methoxycarbonylmethyl, ethoxycarbonylmethyl, methoxycarbonylethyl, ethoxycarbonylethyl, acetyl, propanoic, butanoic, pentanoic, hexanoic and aminocarbonylmethyl; and wherein $R^1$ is selected from cyclobutyl, cyclopentyl, cyclohexyl, cycloheptyl, 1-cyclohexenyl, 2-cyclohexenyl, 3-cyclohexenyl, phenyl, naphthyl, pyridyl, thienyl, thiazolyl, oxazolyl, imidazolyl, furyl, quinolyl, benzothiazolyl, 2,3-thianaphthalenyl, 2,3- dihydrothianaphthalenyl, 2,3-benzofuryl, and 2,3-dihydrobenzofuryl, wherein $R^1$ is optionally substituted at a substitutable position by methyl, ethyl, n-propyl, isopropyl, butyl, tert-butyl, isobutyl, methoxy, ethoxy, propoxy, butoxy, fluoro, chloro, bromo and iodo; or a pharmaceutically-acceptable salt thereof.

8. Compound of claim 7 selected from compounds, and their pharmaceutically-acceptable salts, of the group consisting of 5-(4-fluorophenyl)-2-methyl-4-[4-(methylsulfonyl)phenyl] oxazole;

[5-(4-fluorophenyl)-4-[4-(methylsulfonyl)phenyl]-2-oxazol-2-yl]propanoic acid;

methyl 3-[5-(4-fluorophenyl)-4-[4-(methylsulfonyl)phenyl]-2-oxazol-2-yl]propanate;

4-(4-fluorophenyl)-2-(2-phenylethyl)-5-(4-(methylsulfonyl) phenyl)oxazole;

4-(4-fluorophenyl)-2-methyl-5-[4-methylsulfonylphenyl] oxazole;

4-(4-fluorophenyl)-5-[4-(methylsulfonyl)phenyl]-2-phenyloxazole;

2-benzyl-4-(4-fluorophenyl)-5-(4-(methylsulfonyl)phenyl) oxazole;

4-(4-fluorophenyl)-5-[4-methylsulfonylphenyl]-2-(3-phenyl)propyloxazole;

4-(4-fluorophenyl)-5-[4-methylsulfonylphenyl]-2-propyloxazole;

2-(tert-butyl)-4-(4-fluorophenyl)-5-[4-methylsulfonylphenyl]oxazole;

4-(4-fluorophenyl)-2-(4-methoxyphenyl)methyl-5-[4-methylsulfonylphenyl]oxazole 4-(4-fluorophenyl)-2-(3-methoxyphenyl)methyl-5-[4-methylsulfonylphenyl]oxazole;

2-diphenylmethyl-4-(4-fluorophenyl)-5-[4-methylsulfonylphenyl]oxazole;

2-[4-(4-fluorophenyl)-5-[4-methylsulfonylphenyl]oxazol-2-yl]acetic acid;

ethyl 2-[4-(4-fluorophenyl)-5-[4-methylsulfonyl phenyl]oxazol-2-yl]acetate;

3-[4-(4-fluorophenyl)-5-[4-methylsulfonylphenyl]oxazol-2-yl]propanoic acid;

methyl 3-[4-(4-fluorophenyl)-5-[4-methylsulfonyl phenyl]oxazol-2-yl]propanate;

4-[4-(4-fluorophenyl)-5-[4-methylsulfonylphenyl]oxazol-2-yl]butanoic acid;

methyl 4-[4-(4-fluorophenyl)-5-[4-methylsulfonyl phenyl]oxazol-2-yl]butanate;

3-[4-(4-fluorophenyl)-5-[4-methylsulfonylphenyl]oxazol-2-yl]propanamide;

ethyl 2-[4-(4-fluorophenyl)-5-[4-(methylsulfonyl)phenyl]oxazol-2-yl]-2-benzyl acetate;

4-(4-fluorophenyl)-2-(cyclohexylethyl)-5-[4-(methylsulfonyl)phenyl]oxazole;

4-(4-fluorophenyl)-2-(3-fluorophenoxymethyl)-5-[4-(methylsulfonyl)phenyl]oxazole;

4-(4-fluorophenyl)-2-(3-chlorophenoxymethyl)-5-[4-(methylsulfonyl)phenyl]oxazole;

4-(4-fluorophenyl)-2-(pyridyloxymethyl)-5-[4-(methylsulfonyl)phenyl]oxazole;

4-(4-fluorophenyl)-5-[4-(methylsulfonyl)phenyl]-2-phenoxymethyl oxazole;

4-(4-fluorophenyl)-2-(2-hydroxy)ethyl)-5-[4-(methylsulfonyl)phenyl]oxazole;

4-(4-fluorophenyl)-2-(hydroxymethyl)-5-[4-(methylsulfonyl)phenyl]oxazole;

4-(cyclohexyl)-2-phenyl-5-[4-(methylsulfonyl)phenyl] oxazole;

4-(4-fluorophenyl)-2-benzyloxymethyl-5-[4-(methylsulfonyl)phenyl]oxazole;

4-(4-fluorophenyl)-2-cyclohexyl-5-[4-(methylsulfonyl) phenyl]oxazole; and 5-(4-fluorophenyl)-2-phenyl-4-[4-(methylsulfonyl)phenyl] oxazole.

9. Compound of claim 1 wherein R is selected from alkyl, hydroxyalkyl, haloalkyl, cycloalkyl, cycloalkylalkyl, aryl optionally substituted at a substitutable position by carboxy, alkyl, alkoxy and halo, aralkyl optionally substituted at a substitutable position on the aryl group by carboxy, alkyl, alkoxy and halo, aryloxyalkyl optionally substituted at a substitutable position on the aryl group with halo, carboxy, alkyl and alkoxy, aralkoxyalkyl optionally substituted at a substitutable position by alkyl, carboxy, alkoxy and halo, heteroaryloxyalkyl optionally substituted at a substitutable position on the heteroaryl group with halo, carboxy, alkyl and alkoxy, alkoxycarbonylalkyl, carboxyalkyl and aminocarbonylalkyl; wherein $R^1$ is selected from cycloalkyl, cycloalkenyl, heteroaryl and aryl optionally substituted at a substitutable position by alkyl, alkoxy and halo; and wherein $R^2$ is amino; or a pharmaceutically-acceptable salt thereof; provided R is not methyl.

10. Compound of claim 9 wherein R is selected from lower alkyl, lower hydroxyalkyl, lower haloalkyl, lower cycloalkyl, lower cycloalkylalkyl, aryl selected from phenyl and naphthyl, optionally substituted at a substitutable position by halo, carboxy, lower alkyl and lower alkoxy, lower aralkyl optionally substituted at a substitutable position on the aryl group by halo, carboxy, lower alkyl and lower alkoxy, lower aryloxyalkyl optionally substituted at a substitutable position on the aryl group with halo, carboxy, lower alkyl and lower alkoxy, aralkoxyalkyl optionally substituted at a substitutable position by halo, carboxy, lower alkyl and lower alkoxy, lower heteroaryloxyalkyl optionally substituted at a substitutable position on the heteroaryl group with halo, carboxy, lower alkyl and lower alkoxy, lower alkoxycarbonylalkyl, lower carboxyalkyl and lower aminocarbonylalkyl; and wherein $R^1$ is selected from lower cycloalkyl, lower cycloalkenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by lower alkyl, lower alkoxy and halo; or a pharmaceutically-acceptable salt thereof.

11. Compound of claim 10 wherein R is selected from methyl, ethyl, n-propyl, isopropyl, butyl, tert-butyl, isobutyl, hydroxymethyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyclobutyl, cyclopentyl, cyclohexyl, cycloheptyl, cyclobutylmethyl, cyclopentylmethyl, cyclohexylmethyl, cyclohexylethyl, cyclohexylpropyl, cycloheptylmethyl, aryl selected from phenyl and naphthyl, optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, benzyl, phenethyl, diphenylmethyl and phenpropyl, optionally substituted at a substitutable position on the phenyl group by fluoro, chloro, bromo, iodo, methyl, ethyl, n-propyl, isopropyl, butyl, tert-butyl, isobutyl, carboxy, methoxy, ethoxy, propoxy and butoxy, phenoxymethyl optionally substituted at a substitutable position with fluoro, chloro, bromo, iodo, methyl, ethyl, n-propyl, isopropyl, butyl, tert-butyl, isobutyl, carboxy, methoxy, ethoxy, propoxy and butoxy, benzyloxymethyl optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, pyridyloxymethyl and quinolyloxymethyl, optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, methoxycarbonylmethyl, ethoxycarbonylmethyl, methoxycarbonylethyl, ethoxycarbonylethyl, acetyl, propanoic, butanoic, pentanoic, hexanoic and aminocarbonylmethyl; and wherein $R^1$ is selected from cyclobutyl, cyclopentyl, cyclohexyl, cycloheptyl, 1-cyclohexenyl, 2-cyclohexenyl, 3-cyclohexenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by methyl, ethyl, n-propyl, isopropyl, butyl, tert-butyl, isobutyl, methoxy, ethoxy, propoxy, butoxy, fluoro, chloro, bromo and iodo; or a pharmaceutically-acceptable salt thereof.

12. Compound of claim 11 selected from compounds, and their pharmaceutically-acceptable salts, of the group consisting of 4-[2-benzyl-5-(phenyl)oxazol-4-yl]benzenesulfonamide;
4-[2-benzyl-5-(4-fluorophenyl)oxazol-4-yl]benzenesulfonamide;
4-[2-benzyl-5-(3,4-difluorophenyl)oxazol-4-yl]benzenesulfonamide;
4-[2-benzyl-5-(4-chlorophenyl)oxazol-4-yl]benzenesulfonamide;
4-[2-benzyl-5-(3,4-dichlorophenyl)oxazol-4-yl]benzenesulfonamide;
4-[2-benzyl-5-(4-methoxyphenyl)oxazol-4-yl]benzenesulfonamide;
4-[2-benzyl-5-(3,4-dimethoxyphenyl)oxazol-4-yl]benzenesulfonamide;
4-[2-benzyl-5-(4-methylphenyl)oxazol-4-yl]benzenesulfonamide;
4-[2-benzyl-5-(3,4-dimethylphenyl)oxazol-4-yl]benzenesulfonamide;
4-[2-benzyl-5-(3-chloro-4-methylphenyl)oxazol-4-yl]benzenesulfonamide;
4-[2-benzyl-5-(4-chloro-3-methylphenyl)oxazol-4-yl]benzenesulfonamide;
4-[2-benzyl-5-(3-chloro-4-methoxyphenyl)oxazol-4-yl]benzenesulfonamide;
4-[2-benzyl-5-(4-chloro-3-methoxyphenyl)oxazol-4-yl]benzenesulfonamide;
4-[2-benzyl-5-(3,5-dichloro-4-methoxyphenyl)oxazol-4-yl]benzenesulfonamide;
4-[2-benzyl-5-(3-fluoro-4-methylphenyl)oxazol-4-yl]benzenesulfonamide;
4-[2-benzyl-5-(4-fluoro-3-methylphenyl)oxazol-4-yl]benzenesulfonamide;
4-[2-benzyl-5-(3-fluoro-4-methoxyphenyl)oxazol-4-yl]benzenesulfonamide;
4-[2-benzyl-5-(2-thienyl)oxazol-4-yl]benzenesulfonamide;
4-[2-benzyl-5-(5-chloro-2-thienyl)oxazol-4-yl]benzenesulfonamide;
4-[2-benzyl-5-(cyclohexyl)oxazol-4-yl]benzenesulfonamide;
4-[2-benzyl-5-(1-cyclohexenyl)oxazol-4-yl]benzenesulfonamide;
4-[2-(ethyl)-5-phenyloxazol-4-yl]benzenesulfonamide;
4-[2-(trifluoromethyl)-5-phenyloxazol-4-yl]benzenesulfonamide;
4-[2-(difluoromethyl)-5-phenyloxazol-4-yl]benzenesulfonamide;
4-[2-(hydroxymethyl)-5-phenyloxazol-4-yl]benzenesulfonamide;
4-[2-(carboxy)-5-phenyloxazol-4-yl]benzenesulfonamide;
4-[2-(methoxycarbonyl)-5-phenyloxazol-4-yl]benzenesulfonamide;
4-[2-(ethoxycarbonyl)-5-phenyloxazol-4-yl]benzenesulfonamide;
4-[2-(n-propyl)-5-phenyloxazol-4-yl]benzenesulfonamide;
4-[2-(benzyl)-5-phenyloxazol-4-yl]benzenesulfonamide;
4-[2-(phenoxymethyl)-5-phenyloxazol-4-yl]benzenesulfonamide;
4-[2-((4-chlorophenoxy)methyl)-5-phenyloxazol-4-yl]benzenesulfonamide;
4-[2-((4-fluorophenoxy)methyl)-5-phenyloxazol-4-yl]benzenesulfonamide;
4-[2-((4-carboxyphenoxy)methyl)-5-phenyloxazol-4-yl]benzenesulfonamide;
4-[2-(2-phenethyl)-5-phenyloxazol-4-yl]benzenesulfonamide;
4-[2-(3-phenpropyl)-5-phenyloxazol-4-yl]benzenesulfonamide;
4-[2-(carboxymethyl)-5-phenyloxazol-4-yl]benzenesulfonamide;
4-[2-(ethoxycarbonylmethyl)-5-phenyloxazol-4-yl]benzenesulfonamide;
4-[2-(methoxycarbonylmethyl)-5-phenyloxazol-4-yl]benzenesulfonamide;
4-[2-(2-quinolyloxymethyl)-5-phenyloxazol-4-yl]benzenesulfonamide;
4-[2-benzyl-4-phenyloxazol-5-yl]benzenesulfonamide;
4-[2-benzyl-4-(3,4-difluorophenyl)oxazol-5-yl]benzenesulfonamide;
4-[2-benzyl-4-(4-chlorophenyl)oxazol-5-yl]benzenesulfonamide;
4-[2-benzyl-4-(3,4-dichlorophenyl)oxazol-5-yl]benzenesulfonamide;
4-[2-benzyl-4-(4-methoxyphenyl)oxazol-5-yl]benzenesulfonamide;
4-[2-benzyl-4-(3,4-dimethoxyphenyl)oxazol-5-yl]benzenesulfonamide;
4-[2-benzyl-4-(4-methylphenyl)oxazol-5-yl]benzenesulfonamide;
4-[2-benzyl-4-(3,4-dimethylphenyl)oxazol-5-yl]benzenesulfonamide;
4-[2-benzyl-4-(3-chloro-4-methylphenyl)oxazol-5-yl]benzenesulfonamide;
4-[2-benzyl-4-(4-chloro-3-methylphenyl)oxazol-5-yl]benzenesulfonamide;
4-[2-benzyl-4-(3-chloro-4-methoxyphenyl)oxazol-5-yl]benzenesulfonamide;
4-[2-benzyl-4-(4-chloro-3-methoxyphenyl)oxazol-5-yl]benzenesulfonamide;
4-[2-benzyl-4-(3,5-dichloro-4-methoxyphenyl)oxazol-5-yl]benzenesulfonamide;
4-[2-benzyl-4-(3-fluoro-4-methylphenyl)oxazol-5-yl]benzenesulfonamide;
4-[2-benzyl-4-(4-fluoro-3-methylphenyl)oxazol-5-yl]benzenesulfonamide;
4-[2-benzyl-4-(3-fluoro-4-methoxyphenyl)oxazol-5-yl]benzenesulfonamide;
4-[2-benzyl-4-(2-thienyl)oxazol-5-yl]benzenesulfonamide;
4-[2-benzyl-4-(5-chloro-2-thienyl)oxazol-5-yl]benzenesulfonamide;

4-[2-benzyl-4-(cyclohexyl)oxazol-5-yl]
benzenesulfonamide;
4-[2-benzyl-4-(1-cyclohexenyl)oxazol-5-yl]
benzenesulfonamide;
4-[2-(ethyl)-4-phenyloxazol-5-yl]benzenesulfonamide;
4-[2-(trifluoromethyl)-4-phenyloxazol-5-yl]
benzenesulfonamide;
4-[2-(difluoromethyl)-4-phenyloxazol-5-yl]
benzenesulfonamide;
4-[2-(hydroxymethyl)-4-phenyloxazol-5-yl]
benzenesulfonamide;
4-[2-(carboxy)-4-phenyloxazol-5-yl]benzenesulfonamide;
4-[2-(methoxycarbonyl)-4-phenyloxazol-5-yl]
benzenesulfonamide;
4-[2-(ethoxycarbonyl)-4-phenyloxazol-5-yl]
benzenesulfonamide;
4-[2-(propyl)-4-phenyloxazol-5-yl]benzenesulfonamide;
4-[2-(benzyl)-4-phenyloxazol-5-yl]benzenesulfonamide;
4-[2-(phenoxymethyl)-4-phenyloxazol-5-yl]
benzenesulfonamide;
4-[2-((4-chlorophenoxy)methyl)-4-phenyloxazol-5-yl]
benzenesulfonamide;
4-[2-((4-fluorophenoxy)methyl)-4-phenyloxazol-5-yl]
benzenesulfonamide;
4-[2-((4-carboxyphenoxy)methyl)-4-phenyloxazol-5-yl]
benzenesulfonamide;
4-[2-(2-phenethyl)-4-phenyloxazol-5-yl]
benzenesulfonamide;
4-[2-(3-phenpropyl)-4-phenyloxazol-5-yl]
benzenesulfonamide;
4-[2-(carboxymethyl)-4-phenyloxazol-5-yl]
benzenesulfonamide;
4-[2-(ethoxycarbonylmethyl)-4-phenyloxazol-5-yl]
benzenesulfonamide;
4-[2-(methoxycarbonylmethyl)-4-phenyloxazol-5-yl]
benzenesulfonamide;
4-[2-(2-quinolyloxymethyl)-4-phenyloxazol-5-yl]
benzenesulfonamide;
4-[5-(4-fluorophenyl)-2-methyl-oxazol-4-yl]
benzenesulfonamide;
3-[5-(4-fluorophenyl)-4-(4-aminosulfonylphenyl)oxazol-2-yl]propanoic acid;
methyl 3-[5-(4-fluorophenyl)-4-(4-aminosulfonylphenyl) oxazol-2-yl]propanate;
4-[4-(4-fluorophenyl)-2-(2-phenylethyl)-oxazol-5-yl]
benzenesulfonamide;
4-[4-(4-fluorophenyl)-2-methyl-oxazol-5-yl]
benzenesulfonamide;
4-[4-(4-fluorophenyl)-2-phenyloxazol-5-yl]
benzenesulfonamide;
4-[2-benzyl-4-(4-fluorophenyl)oxazol-5-yl]
benzenesulfonamide;
4-[4-(4-fluorophenyl)-2-(3-phenylpropyl)oxazol-5-yl]
benzenesulfonamide;
4-[4-(4-fluorophenyl)-2-(n-propyl)oxazol-5-yl]
benzenesulfonamide;
4-[2-(tert-butyl)-4-(4-fluorophenyl)oxazol-5-yl]
benzenesulfonamide;
4-[4-(4-fluorophenyl)-2-(4-methoxyphenyl)methyloxazol-5-yl]benzenesulfonamide;
4-[4-(4-fluorophenyl)-2-(3-methoxyphenyl)methyloxazol-5-yl]benzenesulfonamide;
4-[2-diphenylmethyl-4-(4-fluorophenyl)oxazol-5-yl]
benzenesulfonamide;
4-[4-(4-fluorophenyl)-5-[4-aminosulfonylphenyl]oxazol-2-yl]acetic acid;
ethyl 2-[4-(4-fluorophenyl)-5-[4-aminosulfonylphenyl] oxazol-2-yl]acetate;

3-[4-(4-fluorophenyl)-5-[4-aminosulfonylphenyl]oxazol-2-yl]propanoic acid;
methyl 3-[4-(4-fluorophenyl)-5-[4-aminosulfonylphenyl] oxazol-2-yl]propanate;
4-[4-(4-fluorophenyl)-5-[4-aminosulfonylphenyl]oxazol-2-yl]butanoic acid;
methyl 4-[4-(4-fluorophenyl)-5-[4-aminosulfonyl phenyl] oxazol-2-yl]butanate;
3-[4-(4-fluorophenyl)-5-[4-aminosulfonyl phenyl]oxazol-2-yl]propanamide;
ethyl 2-[4-(4-fluorophenyl)-5-[4-aminosulfonyl phenyl] oxazol-2-yl]-2-benzyl-acetate;
4-[4-(4-fluorophenyl)-2-(cyclohexylethyl)oxazol-5-yl]
benzenesulfonamide;
4-[4-(4-fluorophenyl)-2-(3-fluorophenoxymethyl)oxazol-5-yl]benzenesulfonamide;
4-[4-(4-fluorophenyl)-2-(3-chlorophenoxymethyl)oxazol-5-yl]benzenesulfonamide;
4-[4-(4-fluorophenyl)-2-(pyridyloxymethyl)oxazol-5-yl]
benzenesulfonamide;
4-[4-(4-fluorophenyl)-2-phenoxymethyloxazol-5-yl]
benzenesulfonamide;
4-[4-(4-fluorophenyl)-2-(2-hydroxyethyl)oxazo]-5-yl]
benzenesulfonamide;
4-[4-(4-fluorophenyl)-2-(hydroxymethyl)oxazol-5-yl]
benzenesulfonamide;
4-[4-(cyclohexyl)-2-phenyloxazol-5-yl]
benzenesulfonamide;
4-[4-(4-fluorophenyl)-2-benzyloxymethyloxazol-5-yl]
benzenesulfonamide;
4-[4-(4-fluorophenyl)-2-cyclohexyloxazol-5-yl]
benzenesulfonamide; and
4-[5-(4-fluorophenyl)-2-phenyloxazol-4-yl]
benzenesulfonamide.

13. A pharmaceutical composition comprising a therapeutically-effective amount of a compound, said compound selected from a family of compounds of Formula I

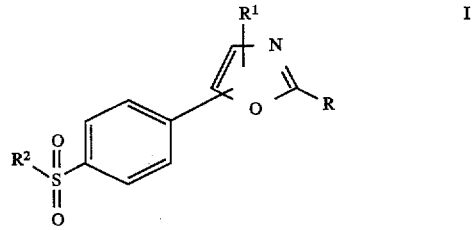

wherein R is selected from hydrido, alkyl, hydroxyalkyl, haloalkyl, alkenyl, hydroxyalkenyl, alkynyl, hydroxyalkynyl, cycloalkyl, cycloalkylalkyl, aryl optionally substituted at a substitutable position by carboxy, alkyl, alkoxy and halo, heteroaryl optionally substituted at a substitutable position by carboxy, alkyl, alkoxy and halo, aralkyl optionally substituted at a substitutable position on the aryl group by carboxy, alkyl, alkoxy and halo, aryloxyalkyl optionally substituted at a substitutable position with halo, carboxy, alkyl and alkoxy, aralkoxyalkyl optionally substituted at a substitutable position with halo, carboxy, alkyl and alkoxy, heteroaryloxyalkyl optionally substituted at a substitutable position with halo, carboxy, alkyl and alkoxy, alkoxycarbonyl, alkoxycarbonylalkyl, carboxy, carboxyalkyl, arylthioalkyl, aminocarbonylalkyl, N-alkylaminocarbonylalkyl and N,N-dialkylaminocarbonylalkyl;

wherein $R^1$ is selected from cycloalkyl, cycloalkenyl, aryl and heteroaryl, wherein $R^1$ is optionally substituted at a substitutable position by alkyl, alkoxy and halo; and wherein R² is selected from alkyl, haloalkyl and amino;
provided R is not alkyl, phenyl, aralkyl, carboxyalkyl or alkoxycarbonylalkyl, when R¹ is 4-fluorophenyl and when R² is methyl;
or a pharmaceutically-acceptable salt thereof.

14. The composition of claim 13 wherein R is selected from hydrido, lower alkyl, lower hydroxyalkyl, lower haloalkyl, lower alkenyl, lower hydroxyalkenyl, lower alkynyl, lower hydroxyalkynyl, lower cycloalkyl, lower cycloalkylalkyl, aryl selected from phenyl and naphthyl, optionally substituted at a substitutable position by halo, carboxy, lower alkyl and lower alkoxy, heteroaryl selected from pyridyl, thienyl, thiazolyl, oxazolyl, imidazolyl, furyl and quinolyl, optionally substituted at a substitutable position by halo, carboxy, lower alkyl and lower alkoxy, lower aralkyl optionally substituted at a substitutable position on the aryl group by halo, carboxy, lower alkyl and lower alkoxy, lower aryloxyalkyl optionally substituted at a substitutable position with halo, carboxy, lower alkyl and lower alkoxy, lower heteroaryloxyalkyl optionally substituted at a substitutable position with halo, carboxy, lower alkyl and lower alkoxy, lower aralkoxyalkyl optionally substituted at a substitutable position with halo, carboxy, lower alkyl and lower alkoxy, lower alkoxycarbonyl, lower alkoxycarbonylalkyl, carboxy, lower carboxyalkyl, lower arylthioalkyl, lower aminocarbonylalkyl, lower N-alkylaminocarbonylalkyl and lower N,N-dialkylaminocarbonylalkyl; wherein R¹ is selected from lower cycloalkyl, lower cycloalkenyl, phenyl, naphthyl and heteroaryl selected from pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein R¹ is optionally substituted at a substitutable position by lower alkyl, lower alkoxy and halo; and wherein R² is methyl or amino; or a pharmaceutically-acceptable salt thereof.

15. The composition of claim 14 wherein R is selected from hydrido, methyl, ethyl, n-propyl, isopropyl, butyl, tert-butyl, isobutyl, hydroxymethyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, ethenyl, 1-propenyl, 2-propenyl, 1-butenyl, 2-butenyl, 3-butenyl, hydroxyethenyl, ethynyl, 1-propynyl, 2-propynyl, 1-butynyl, 2-butynyl, 3-butynyl, hydroxyethynyl, cyclobutyl, cyclopentyl, cyclohexyl, cycloheptyl, cyclobutylmethyl, cyclopentylmethyl, cyclohexylmethyl, cyclohexylethyl, cyclohexylpropyl, cycloheptylmethyl, phenyl and naphthyl, optionally substituted at a substitutable position by fluoro, chloro, bromo, iodo, carboxy, methyl, ethyl, n-propyl, isopropyl, butyl, tert-butyl, isobutyl, methoxy, ethoxy, propoxy and butoxy, pyridyl, thienyl, thiazolyl, oxazolyl, imidazolyl, furyl and quinolyl, optionally substituted at a substitutable position by fluoro, chloro, bromo, iodo, carboxy, methyl, ethyl, n-propyl, isopropyl, butyl, tert-butyl, isobutyl, methoxy, ethoxy, propoxy and butoxy, benzyl, phenethyl, diphenylmethyl and phenpropyl, optionally substituted at a substitutable position on the phenyl group by fluoro, chloro, bromo, iodo, carboxy, methyl, ethyl, n-propyl, isopropyl, butyl, tert-butyl, isobutyl, methoxy, ethoxy, propoxy and butoxy, phenoxymethyl optionally substituted at a substitutable position on the phenyl group with fluoro, chloro, bromo, iodo, carboxy, methyl, ethyl, n-propyl, isopropyl, butyl, tert-butyl, isobutyl, methoxy, ethoxy, propoxy and butoxy, benzyloxymethyl optionally substituted at a substitutable position on the phenyl group with fluoro, chloro, bromo, iodo, carboxy, methyl, ethyl, n-propyl, isopropyl, butyl, tert-butyl, isobutyl, methoxy, ethoxy, propoxy and butoxy, pyridyloxymethyl and quinolyloxymethyl optionally substituted at a substitutable position with fluoro, chloro, bromo, iodo, carboxy, methyl, ethyl, n-propyl, isopropyl, butyl, tert-butyl, isobutyl, methoxy, ethoxy, propoxy and butoxy, methoxycarbonyl, ethoxycarbonyl, propoxycarbonyl, butoxycarbonyl, methoxycarbonylmethyl, ethoxycarbonylmethyl, methoxycarbonylethyl, ethoxycarbonylethyl, carboxy, acetyl, propanoic, butanoic, pentanoic, hexanoic, phenylthiomethyl, aminocarbonylmethyl, N-methylaminocarbonylmethyl and N,N-dimethylaminocarbonylmethyl; wherein R¹ is selected from cyclobutyl, cyclopentyl, cyclohexyl, cycloheptyl, 1-cyclohexenyl, 2-cyclohexenyl, 3-cyclohexenyl, cyclopentenyl, cycloheptenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein R¹ is optionally substituted at a substitutable position by methyl, ethyl, n-propyl, isopropyl, butyl, tert-butyl, isobutyl, methoxy, ethoxy, propoxy, butoxy, fluoro, chloro, bromo and iodo; and wherein R² is methyl or amino; or a pharmaceutically-acceptable salt thereof.

16. The composition of claim 15 selected from compounds, and their pharmaceutically-acceptable salts, of the group consisting of 4-[2-benzyl-5-(phenyl)oxazol-4-yl]benzenesulfonamide;

4-[2-benzyl-5-(4-fluorophenyl)oxazol-4-yl]benzenesulfonamide;

4-[2-benzyl-5-(3,4-difluorophenyl)oxazol-4-yl]benzenesulfonamide;

4-[2-benzyl-5-(4-chlorophenyl)oxazol-4-yl]benzenesulfonamide;

4-[2-benzyl-5-(3,4-dichlorophenyl)oxazol-4-yl]benzenesulfonamide;

4-[2-benzyl-5-(4-methoxyphenyl)oxazol-4-yl]benzenesulfonamide;

4-[2-benzyl-5-(3,4-dimethoxyphenyl)oxazol-4-yl]benzenesulfonamide;

4-[2-benzyl-5-(4-methylphenyl)oxazol-4-yl]benzenesulfonamide;

4-[2-benzyl-5-(3,4-dimethylphenyl)oxazol-4-yl]benzenesulfonamide;

4-[2-benzyl-5-(3-chloro-4-methylphenyl)oxazol-4-yl]benzenesulfonamide;

4-[2-benzyl-5-(4-chloro-3-methylphenyl)oxazol-4-yl]benzenesulfonamide;

4-[2-benzyl-5-(3-chloro-4-methoxyphenyl)oxazol-4-yl]benzenesulfonamide;

4-[2-benzyl-5-(4-chloro-3-methoxyphenyl)oxazol-4-yl]benzenesulfonamide;

4-[2-benzyl-5-(3,5-dichloro-4-methoxyphenyl)oxazol-4-yl]benzenesulfonamide;

4-[2-benzyl-5-(3-fluoro-4-methylphenyl)oxazol-4-yl]benzenesulfonamide;

4-[2-benzyl-5-(4-fluoro-3-methylphenyl)oxazol-4-yl]benzenesulfonamide;

4-[2-benzyl-5-(3-fluoro-4-methoxyphenyl)oxazol-4-yl]benzenesulfonamide;

4-[2-benzyl-5-(2-thienyl)oxazol-4-yl]benzenesulfonamide;

4-[2-benzyl-5-(5-chloro-2-thienyl)oxazol-4-yl]benzenesulfonamide;

4-[2-benzyl-5-(cyclohexyl)oxazol-4-yl]benzenesulfonamide;

4-[2-benzyl-5-(1-cyclohexenyl)oxazol-4-yl]
benzenesulfonamide;
2-benzyl-4-(4-methylsulfonylphenyl)-5-phenyloxazole;
2-benzyl-4-(4-methylsulfonylphenyl)-5-(3,4-difluorophenyl)oxazole;
2-benzyl-4-(4-methylsulfonylphenyl)-5-(4-chlorophenyl)oxazole;
2-benzyl-4-(4-methylsulfonylphenyl)-5-(3,4-dichlorophenyl)oxazole;
2-benzyl-4-(4-methylsulfonylphenyl)-5-(4-methoxyphenyl)oxazole;
2-benzyl-4-(4-methylsulfonylphenyl)-5-(3,4-dimethoxyphenyl)oxazole;
2-benzyl-4-(4-methylsulfonylphenyl)-5-(4-methylphenyl)oxazole;
2-benzyl-4-(4-methylsulfonylphenyl)-5-(3,4-dimethylphenyl)oxazole;
2-benzyl-4-(4-methylsulfonylphenyl)-5-(3-chloro-4-methylphenyl)oxazole;
2-benzyl-4-(4-methylsulfonylphenyl)-5-(4-chloro-3-methylphenyl)oxazole;
2-benzyl-4-(4-methylsulfonylphenyl)-5-(3-chloro-4-methoxyphenyl)oxazole;
2-benzyl-4-(4-methylsulfonylphenyl)-5-(4-chloro-3-methoxyphenyl)oxazole;
2-benzyl-4-(4-methylsulfonylphenyl)-5-(3,5-dichloro-4-methoxyphenyl)oxazole;
2-benzyl-4-(4-methylsulfonylphenyl)-5-(3-fluoro-4-methylphenyl)oxazole;
2-benzyl-4-(4-methylsulfonylphenyl)-5-(4-fluoro-3-methylphenyl)oxazole;
2-benzyl-4-(4-methylsulfonylphenyl)-5-(3-fluoro-4-methoxyphenyl)oxazole;
2-benzyl-4-(4-methylsulfonylphenyl)-5-(2-thienyl)oxazole;
2-benzyl-4-(4-methylsulfonylphenyl)-5-(5-chloro-2-thienyl)oxazole;
2-benzyl-4-(4-methylsulfonylphenyl)-5-(cyclohexyl)oxazole-;
2-benzyl-4-(4-methylsulfonylphenyl)-5-(1-cyclohexenyl)oxazole;
2-(ethyl)-4-(4-methylsulfonylphenyl)-5-phenyloxazole;
2-(trifluoromethyl)-4-(4-methylsulfonylphenyl)-5-phenyloxazole;
2-(difluoromethyl)-4-(4-methylsulfonylphenyl)-5-phenyloxazole;
2-(hydroxymethyl)-4-(4-methylsulfonylphenyl)-5-phenyloxazole;
2-(carboxy)-4-(4-methylsulfonylphenyl)-5-phenyloxazole;
2-(methoxycarbonyl)-4-(4-methylsulfonylphenyl)-5-phenyloxazole;
2-(ethoxycarbonyl)-4-(4-methylsulfonylphenyl)-5-phenyloxazole;
2-(propyl)-4-(4-methylsulfonylphenyl)-5-phenyloxazole;
2-(benzyl)-4-(4-methylsulfonylphenyl)-5-phenyloxazole;
2-(phenoxymethyl)-4-(4-methylsulfonylphenyl)-5-phenyloxazole;
2-((4-chlorophenoxy)methyl)-4-(4-methylsulfonylphenyl)-5-phenyloxazole;
2-((4-fluorophenoxy)methyl)-4-(4-methylsulfonylphenyl)-5-phenyloxazole;
2-((4-carboxyphenoxy)methyl)-4-(4-methylsulfonylphenyl)-5-phenyloxazole;
2-(2-phenethyl)-4-(4-methylsulfonylphenyl)-5-phenyloxazole;
2-3-phenpropyl)-4-(4-methylsulfonylphenyl)-5-phenyloxazole;
2-carboxymethyl)-4-(4-methylsulfonylphenyl)-5-phenyloxazole;
2-ethoxycarbonylmethyl)-4-(4-methylsulfonylphenyl)-5-phenyloxazole;
2-(methoxycarbonylmethyl)-4-(4-methylsulfonylphenyl)-5-phenyloxazole;
2-(2-quinolyloxymethyl)-4-(4-methylsulfonylphenyl)-5-phenyloxazole;
4-[2-(ethyl)-5-phenyloxazol-4-yl]benzenesulfonamide;
4-[2-(trifluoromethyl)-5-phenyloxazol-4-yl]
benzenesulfonamide;
4-[2-(difluoromethyl)-5-phenyloxazol-4-yl]
benzenesulfonamide;
4-[2-(hydroxymethyl)-5-phenyloxazol-4-yl]
benzenesulfonamide;
4-[2-(carboxy)-5-phenyloxazol-4-yl]benzenesulfonamide;
4-[2-(methoxycarbonyl)-5-phenyloxazol-4-yl]
benzenesulfonamide;
4-[2-(ethoxycarbonyl)-5-phenyloxazol-4-yl]
benzenesulfonamide;
4-[2-(propyl)-5-phenyloxazol-4-yl]benzenesulfonamide;
4-[2-(benzyl)-5-phenyloxazol-4-yl]benzenesulfonamide;
4-[2-(phenoxymethyl)-5-phenyloxazol-4-yl]
benzenesulfonamide;
4-[2-((4-chlorophenoxy)methyl)-5-phenyloxazol-4-yl]
benzenesulfonamide;
4-[2-((4-fluorophenoxy)methyl)-5-phenyloxazol-4-yl]
benzenesulfonamide;
4-[2-((4-carboxyphenoxy)methyl)-5-phenyloxazol-4-yl]
benzenesulfonamide;
4-[2-(2-phenethyl)-5-phenyloxazol-4-yl]
benzenesulfonamide;
4-[2-(3-phenpropyl)-5-phenyloxazol-4-yl]
benzenesulfonamide;
4-[2-(carboxymethyl)-5-phenyloxazol-4-yl]
benzenesulfonamide;
4-[2-(ethoxycarbonylmethyl)-5-phenyloxazol-4-yl]
benzenesulfonamide;
4-[2-(methoxycarbonylmethyl)-5-phenyloxazol-4-yl]
benzenesulfonamide;
4-[2-(2-quinolyloxymethyl)-5-phenyloxazol-4-yl]
benzenesulfonamide;
4-[2-benzyl-4-phenyloxazol-5-yl]benzenesulfonamide;
4-[2-benzyl-4-(4-fluorophenyl)oxazol-5-yl]
benzenesulfonamide;
4-[2-benzyl-4-(3,4-difluorophenyl)oxazol-5-yl]
benzenesulfonamide;
4-[2-benzyl-4-(4-chlorophenyl)oxazol-5-yl]
benzenesulfonamide;
4-[2-benzyl-4-(3,4-dichlorophenyl)oxazol-5-yl]
benzenesulfonamide;
4-[2-benzyl-4-(4-methoxyphenyl)oxazol-5-yl]
benzenesulfonamide;
4-[2-benzyl-4-(3,4-dimethoxyphenyl)oxazol-5-yl]
benzenesulfonamide;
4-[2-benzyl-4-(4-methylphenyl)oxazol-5-yl]
benzenesulfonamide;
4-[2-benzyl-4-(3,4-dimethylphenyl)oxazol-5-yl]
benzenesulfonamide;
4-[2-benzyl-4-(3-chloro-4-methylphenyl)oxazol-5-yl]
benzenesulfonamide;
4-[2-benzyl-4-(4-chloro-3-methylphenyl)oxazol-5-yl]
benzenesulfonamide;
4-[2-benzyl-4-(3-chloro-4-methoxyphenyl)oxazol-5-yl]
benzenesulfonamide;
4-[2-benzyl-4-(4-chloro-3-methoxyphenyl)oxazol-5-yl]
benzenesulfonamide;
4-[2-benzyl-4-(3,5-dichloro-4-methoxyphenyl)oxazol-5-yl]
benzenesulfonamide;

4-[2-benzyl-4-(3-fluoro-4-methylphenyl)oxazol-5-yl]
benzenesulfonamide;
4-[2-benzyl-4-(4-fluoro-3-methylphenyl)oxazol-5-yl]
benzenesulfonamide;
4-[2-benzyl-4-(3-fluoro-4-methoxyphenyl)oxazol-5-yl]
benzenesulfonamide;
4-[2-benzyl-4-(2-thienyl)oxazol-5-yl]benzenesulfonamide;
4-[2-benzyl-4-(5-chloro-2-thienyl)oxazol-5-yl]
benzenesulfonamide;
4-[2-benzyl-4-(cyclohexyl)oxazol-5-yl]
benzenesulfonamide;
4-[2-benzyl-4-(1-cyclohexenyl)oxazol-5-yl]
benzenesulfonamide;
2-benzyl-5-(4-methylsulfonylphenyl-4-phenyloxazole;
2-benzyl-5-(4-methylsulfonylphenyl-4-(3,4-difluorophenyl)
oxazole;
2-benzyl-5-(4-methylsulfonylphenyl-4-(4-chlorophenyl)
oxazol-4-yl]benzenesulfonamide;
2-benzyl-5-(4-methylsulfonylphenyl)-4-(3,4-
dichlorophenyl)oxazole;
2-benzyl-5-(4-methylsulfonylphenyl)-4-(4-methoxyphenyl)
oxazole;
2-benzyl-5-(4-methylsulfonylphenyl)-4-(3,4-
dimethoxyphenyl)oxazole;
2-benzyl-5-(4-methylsulfonylphenyl)-4-(4-methylphenyl)
oxazole;
2-benzyl-5-(4-methylsulfonylphenyl)-4-(3,4-
dimethylphenyl)oxazole;
2-benzyl-5-(4-methylsulfonylphenyl)-4-(3-chloro-4-
methylphenyl)oxazole;
2-benzyl-5-4-methylsulfonylphenyl)-4-(4-chloro-3-
methylphenyl)oxazole;
2-benzyl-5-(4-methylsulfonylphenyl)-4-(3-chloro-4-
methoxyphenyl)oxazole;
2-benzyl-5-(4-methylsulfonylphenyl)-4-(4-chloro-3-
methoxyphenyl)oxazole;
2-benzyl-5-(4-methylsulfonylphenyl)-4-(3,5-dichloro-4-
methoxyphenyl)oxazole;
2-benzyl-5-(4-methylsulfonylphenyl)-4-(3-fluoro-4-
methylphenyl)oxazole;
2-benzyl-5-(4-methylsulfonylphenyl)-4-(4-fluoro-3-
methylphenyl)oxazole;
2-benzyl-5-(4-methylsulfonylphenyl)-4-(3-fluoro-4-
methoxyphenyl)oxazole;
2-benzyl-5-(4-methylsulfonylphenyl)-4-(2-thienyl)oxazole;
2-benzyl-5-(4-methylsulfonylphenyl)-4-(5-chloro-2-
thienyl)oxazole;
2-benzyl-5-(4-methylsulfonylphenyl)-4-(cyclohexyl)
oxazole-;
2-benzyl-5-(4-methylsulfonylphenyl)-4-(2-cyclohexenyl)
oxazole;
2-(ethyl)-5-(4-methylsulfonylphenyl)-4-phenyloxazole;
2-(trifluoromethyl)-5-(4-methylsulfonylphenyl)-4-
phenyloxazole;
2-(difluoromethyl)-5-(4-methylsulfonylphenyl)-4-
phenyloxazole;
2-(hydroxymethyl)-5-(4-methylsulfonylphenyl)-4-
phenyloxazole;
2-(carboxy)-5-(4-methylsulfonylphenyl)-4-phenyloxazole;
2-(methoxycarbonyl)-5-(4-methylsulfonylphenyl)-4-
phenyloxazole;
2-(ethoxycarbonyl)-5-(4-methylsulfonylphenyl)-4-
phenyloxazole;
2-(propyl)-5-(4-methylsulfonylphenyl)-4-phenyloxazole;
2-(benzyl)-5-(4-methylsulfonylphenyl)-4-phenyloxazole;
2-(phenoxymethyl)-5-(4-methylsulfonylphenyl)-4-
phenyloxazole;
2-((4-chlorophenoxy)methyl)-5-(4-methylsulfonylphenyl)-
4-phenyloxazole;
2-((4-fluorophenoxy)methyl)-5-(4-methylsulfonylphenyl)-
4-phenyloxazole;
2-((4-carboxyphenoxy)methyl)-5-(4-methylsulfonylphenyl)
-4-phenyloxazole;
2-(2-phenethyl)-5-(4-methylsulfonylphenyl)-4-
phenyloxazole;
2-(3-phenpropyl)-5-(4-methylsulfonylphenyl)-4-
phenyloxazole;
2-(carboxymethyl)-5-(4-methylsulfonylphenyl)-4-
phenyloxazole;
2-(ethoxycarbonylmethyl)-5-(4-methylsulfonylphenyl)-4-
phenyloxazole;
2-(methoxycarbonylmethyl)-5-(4-methylsulfonylphenyl)-4-
phenyloxazole;
2-(2-quinolyloxymethyl)-5-(4-methylsulfonylphenyl)-4-
phenyloxazole;
4-[2-(ethyl)-4-phenyloxazol-5-yl]benzenesulfonamide;
4-[2-(trifluoromethyl)-4-phenyloxazol-5-yl]
benzenesulfonamide;
4-[2-(difluoromethyl)-4-phenyloxazol-5-yl]
benzenesulfonamide;
4-[2-(hydroxymethyl)-4-phenyloxazol-5-yl]
benzenesulfonamide;
4-[2-(carboxy)-4-phenyloxazol-5-yl]benzenesulfonamide;
4-[2-(methoxycarbonyl)-4-phenyloxazol-5-yl]
benzenesulfonamide;
4-[2-(ethoxycarbonyl)-4-phenyloxazol-5-yl]
benzenesulfonamide;
4-[2-(propyl)-4-phenyloxazol-5-yl]benzenesulfonamide;
4-[2-(benzyl)-4-phenyloxazol-5-yl]benzenesulfonamide;
4-[2-(phenoxymethyl)-4-phenyloxazol-5-yl]
benzenesulfonamide;
4-[2-((4-chlorophenoxy)methyl)-4-phenyloxazol-5-yl]
benzenesulfonamide;
4-[2-((4-fluorophenoxy)methyl)-4-phenyloxazol-5-yl]
benzenesulfonamide;
4-[2-((4-carboxyphenoxy)methyl)-4-phenyloxazol-5-yl]
benzenesulfonamide;
4-[2-(2-phenethyl)-4-phenyloxazol-5-yl]
benzenesulfonamide;
4-[2-(3-phenpropyl)-4-phenyloxazol-5-yl]
benzenesulfonamide;
4-[2-(carboxymethyl)-4-phenyloxazol-5-yl]
benzenesulfonamide;
4-[2-(ethoxycarbonylmethyl)-4-phenyloxazol-5-yl]
benzenesulfonamide;
4-[2-(methoxycarbonylmethyl)-4-phenyloxazol-5-yl]
benzenesulfonamide;
4-[2-(2-quinolyloxymethyl)-4-phenyloxazol-5-yl]
benzenesulfonamide;
5-(4-fluorophenyl)-2-methyl-4-[4-(methylsulfonyl)phenyl]
oxazole;
3-[5-(4-fluorophenyl)-4-[4-(methylsulfonyl)phenyl]oxazol-
2-yl]propanoic acid;
methyl 3-[5-(4-fluorophenyl)-4-[4-(methylsulfonyl)phenyl]
oxazol-2-yl]propanate;
4-(4-fluorophenyl)-2-(2-phenyl)ethyl-5-(4-(methylsulfonyl)
phenyl)oxazole;
4-(4-fluorophenyl)-2-methyl-5-[4-(methylsulfonylphenyl]
oxazole;
4-(4-fluorophenyl)-5-[4-(methylsulfonyl)phenyl]-2-
phenyloxazole;
2-benzyl-4-(4-fluorophenyl)-5-(4-(methylsulfonyl)phenyl)
oxazole;
4-(4-fluorophenyl)-5-[4-methylsulfonylphenyl]-2-(3-
phenyl)propyloxazole;

4-(4-fluorophenyl)-5-[4-methylsulfonylphenyl]-2-propyloxazole;

2-tert-butyl)-4-(4-fluorophenyl)-5-[4-methylsulfonylphenyl]oxazole;

4-4-fluorophenyl)-2-(4-methoxyphenyl)methyl-5-[4-methylsulfonylphenyl]oxazole 4-4-fluorophenyl)-2-(3-methoxyphenyl)methyl-5-[4-methylsulfonylphenyl]oxazole;

2-diphenylmethyl-4-(4-fluorophenyl)-5-[4-methylsulfonylphenyl]oxazole;

2-[4-(4-fluorophenyl)-5-[4-methylsulfonylphenyl]oxazol-2-yl]acetic acid;

ethyl 2-[4-(4-fluorophenyl)-5-[4methylsulfonyl)phenyl]oxazol-2-yl]acetate;

3-[4-(4-fluorophenyl)-5-[4-methylsulfonyl)phenyl]oxazol-2-yl]propanoic acid;

methyl 3-[4-(4-fluorophenyl)-5-[4-methylsulfonyl)phenyl]oxazol-2-yl]propanate;

4-[4-(4-fluorophenyl)-5-[4-methylsulfonyl)phenyl]oxazol-2-yl]butanoic acid;

methyl 4-[4-(4-fluorophenyl)-5-[4-methylsulfonyl)phenyl]oxazol-2-yl]butanate;

3-[4-(4-fluorophenyl)-5-[4-methylsulfonyl)phenyl]oxazol-2-yl]propanamide;

ethyl 2-[4-(4-fluorophenyl)-5-[4-(methylsulfonyl)phenyl]oxazol-2-yl]-2-benzyl-acetate;

4-(4-fluorophenyl)-2-(cyclohexylethyl)-5-[4-(methylsulfonyl)phenyl]oxazole;

4-(4-fluorophenyl)-2-(3-fluorophenoxymethyl)-5-[4-(methylsulfonyl)phenyl]oxazole;

4-(4-fluorophenyl)-2-(3-chlorophenoxymethyl)-5-[4-(methylsulfonyl)phenyl]oxazole;

4-(4-fluorophenyl)-2-(pyridyloxymethyl)-5-[4-(methylsulfonyl)phenyl]oxazole;

4-(4-fluorophenyl)-5-[4-(methylsulfonyl)phenyl]-2-phenoxymethyloxazole;

4-(4-fluorophenyl)-2-(2-hydroxyethyl)-5-[4-(methylsulfonyl)phenyl]oxazole;

4-(4-fluorophenyl)-2-(hydroxymethyl)-5-[4-(methylsulfonyl)phenyl]oxazole;

4-(cyclohexyl)-2-phenyl-5-[4-(methylsulfonyl)phenyl]oxazole;

4-(4-fluorophenyl)-2-benzyloxymethyl-5-[4-(methylsulfonyl)phenyl]oxazole;

4-(4-fluorophenyl)-2-cyclohexyl-5-[4-(methylsulfonyl)phenyl]oxazole; and 5-(4-fluorophenyl)-2-phenyl-4-[4-(methylsulfonyl)phenyl]oxazole.

17. The composition of claim 13 wherein R is selected from alkyl, hydroxyalkyl, haloalkyl, cycloalkyl, cycloalkylalkyl, aryl optionally substituted at a substitutable position by carboxy, alkyl, alkoxy and halo, aralkyl optionally substituted at a substitutable position on the aryl group by carboxy, alkyl, alkoxy and halo, aryloxyalkyl optionally substituted at a substitutable position on the aryl group with halo, carboxy, alkyl and alkoxy, aralkoxyalkyl optionally substituted at a substitutable position by alkyl, carboxy, alkoxy and halo, heteroaryloxyalkyl optionally substituted at a substitutable position on the heteroaryl group with halo, carboxy, alkyl and alkoxy, alkoxycarbonylalkyl, carboxyalkyl and aminocarbonylalkyl; wherein $R^1$ is selected from cycloalkyl, cycloalkenyl, heteroaryl and aryl optionally substituted at a substitutable position by alkyl, alkoxy and halo; and wherein $R^2$ is methyl; or a pharmaceutically-acceptable salt thereof.

18. The composition of claim 17 wherein R is selected from lower alkyl, lower hydroxyalkyl, lower haloalkyl, lower cycloalkyl, lower cycloalkylalkyl, aryl selected from phenyl and naphthyl, optionally substituted at a substitutable position by halo, carboxy, lower alkyl and lower alkoxy, lower aralkyl optionally substituted at a substitutable position on the aryl radical by halo, carboxy, lower alkyl and lower alkoxy, lower aryloxyalkyl optionally substituted at a substitutable position on the aryl group with halo, carboxy, lower alkyl and lower alkoxy, aralkoxyalkyl optionally substituted at a substitutable position by halo, carboxy, lower alkyl and lower alkoxy, lower heteroaryloxyalkyl optionally substituted at a substitutable position on the heteroaryl group with halo, carboxy, lower alkyl and lower alkoxy, lower alkoxycarbonylalkyl, lower carboxyalkyl and lower aminocarbonylalkyl; and wherein $R^1$ is selected from lower cycloalkyl, lower cycloalkenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by lower alkyl, lower alkoxy and halo; or a pharmaceutically-acceptable salt thereof.

19. The composition of claim 18 wherein R is selected from methyl, ethyl, n-propyl, isopropyl, butyl, tert-butyl, isobutyl, hydroxymethyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyclobutyl, cyclopentyl, cyclohexyl, cycloheptyl, cyclobutylmethyl, cyclopentylmethyl, cyclohexylmethyl, cyclohexylethyl, cyclohexylpropyl, cycloheptylmethyl, aryl selected from phenyl and naphthyl, optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, benzyl, phenethyl, diphenylmethyl and phenpropyl, optionally substituted at a substitutable position on the phenyl group by fluoro, chloro, bromo, iodo, methyl, ethyl, n-propyl, isopropyl, butyl, tert-butyl, isobutyl, carboxy, methoxy, ethoxy, propoxy and butoxy, phenoxymethyl optionally substituted at a substitutable position with fluoro, chloro, bromo, iodo, methyl, ethyl, n-propyl, isopropyl, butyl, tert-butyl, isobutyl, carboxy, methoxy, ethoxy, propoxy and butoxy, benzyloxymethyl optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, pyridyloxymethyl and quinolyloxymethyl, optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, methoxycarbonylmethyl, ethoxycarbonylmethyl, methoxycarbonylethyl, ethoxycarbonylethyl, acetyl, propanoic, butanoic, pentanoic, hexanoic and aminocarbonylmethyl; and wherein $R^1$ is selected from cyclobutyl, cyclopentyl, cyclohexyl, cycloheptyl, 1-cyclohexenyl, 2-cyclohexenyl, 3-cyclohexenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by methyl, ethyl, n-propyl, isopropyl, butyl, tert-butyl, isobutyl, methoxy, ethoxy, propoxy, butoxy, fluoro, chloro, bromo and iodo; or a pharmaceutically-acceptable salt thereof.

20. The composition of claim 19 selected from compounds and their pharmaceutically-acceptable salts, of the group consisting of 5-(4-fluorophenyl)-2-methyl-4-[4-(methylsulfonyl)phenyl]
oxazole;
[5-(4-fluorophenyl)-4-[4-(methylsulfonyl)phenyl]-2-
oxazol-2-yl]propanoic acid;
methyl 3-[5-(4-fluorophenyl)-4-[4-(methylsulfonyl)phenyl]
-2-oxazol-2-yl]propanate;
4-(4-fluorophenyl)-2-(2-phenylethyl)-5-(4-(methylsulfonyl)
phenyl)oxazole;
4-(4-fluorophenyl)-2-methyl-5-[4-methylsulfonylphenyl]
oxazole;
4-(4-fluorophenyl)-5-[4-(methylsulfonyl)phenyl]-2-
phenyloxazole;
2-benzyl-4-(4-fluorophenyl)-5-(4-(methylsulfonyl)phenyl)
oxazole;
4-(4-fluorophenyl)-5-[4-methylsulfonylphenyl]-2-(3-
phenyl)propyloxazole;
4-(4-fluorophenyl)-5-[4-methylsulfonylphenyl]-2-
propyloxazole;
2-(tert-butyl)-4-(4-fluorophenyl)-5-[4-
methylsulfonylphenyl]oxazole;
4-(4-fluorophenyl)-2-(4-methoxyphenyl)methyl-5-[4-
methylsulfonylphenyl]oxazole
4-(4-fluorophenyl)-2-(3-methoxyphenyl)methyl-5-[4-
methylsulfonylphenyl]oxazole;
2-diphenylmethyl-4-(4-fluorophenyl)-5-[4-
methylsulfonylphenyl]oxazole;
2-[4-(4-fluorophenyl)-5-[4-methylsulfonylphenyl]oxazol-2-
yl]acetic acid;
ethyl 2-[4-(4-fluorophenyl)-5-[4-methylsulfonyl phenyl]
oxazol-2-yl]acetate;
3-[4-(4-fluorophenyl)-5-[4-methylsulfonylphenyl]oxazol-2-
yl]propanoic acid;
methyl 3-[4-(4-fluorophenyl)-5-[4-methylsulfonyl phenyl]
oxazol-2-yl]propanate;
4-[4-(4-fluorophenyl)-5-[4-methylsulfonylphenyl]oxazol-2-
yl]butanoic acid;
methyl 4-[4-(4-fluorophenyl)-5-[4-methylsulfonyl phenyl]
oxazol-2-yl]butanate;
3-[4-(4-fluorophenyl)-5-[4-methylsulfonylphenyl]oxazol-2-
yl]propanamide;
ethyl 2-[4-(4-fluorophenyl)-5-[4-(methylsulfonyl)phenyl]
oxazol-2-yl]-2-benzyl acetate;
4-(4-fluorophenyl)-2-(cyclohexylethyl)-5-[4-
(methylsulfonyl)phenyl]oxazole;
4-(4-fluorophenyl)-2-(3-fluorophenoxymethyl)-5-[4-
(methylsulfonyl)phenyl]oxazole;
4-(4-fluorophenyl)-2-(3-chlorophenoxymethyl)-5-[4-
(methylsulfonyl)phenyl]oxazole;
4-4-fluorophenyl)-2-(pyridyloxymethyl)-5-[4-
(methylsulfonyl)phenyl]oxazole;
4-4-fluorophenyl)-5-[4-(methylsulfonyl)phenyl]-2-
phenoxymethyl oxazole;
4-(4-fluorophenyl)-2-(2-hydroxy)ethyl)-5-[4-
(methylsulfonyl)phenyl]oxazole;
4-4-fluorophenyl)-2-(hydroxymethyl)-5-[4-
(methylsulfonyl)phenyl]oxazole;
4-(cyclohexyl)-2-phenyl-5-[4-(methylsulfonyl)phenyl]
oxazole;
4-(4-fluorophenyl)-2-benzyloxymethyl-5-[4-
(methylsulfonyl)phenyl]oxazole;
4-(4-fluorophenyl)-2-cyclohexyl-5-[4-(methylsulfonyl)
phenyl]oxazole; and
5-4-fluorophenyl)-2-phenyl-4-[4-(methylsulfonyl)phenyl]
oxazole.

21. The composition of claim 13 wherein R is selected
from alkyl, hydroxyalkyl, haloalkyl, cycloalkyl,
cycloalkylalkyl, aryl optionally substituted at a substitutable
position by carboxy, alkyl, alkoxy and halo, aralkyl option-
ally substituted at a substitutable position on the aryl group
by carboxy, alkyl, alkoxy and halo, aryloxyalkyl optionally
substituted at a substitutable position on the aryl group with
halo, carboxy, alkyl and alkoxy, aralkoxyalkyl optionally
substituted at a substitutable position by alkyl, carboxy,
alkoxy and halo, heteroaryloxyalkyl optionally substituted at
a substitutable position on the heteroaryl group with halo,
carboxy, alkyl and alkoxy, alkoxycarbonylalkyl, carboxy-
alkyl and aminocarbonylalkyl; wherein $R^1$ is selected from
cycloalkyl, cycloalkenyl, heteroaryl and aryl optionally sub-
stituted at a substitutable position by alkyl, alkoxy and halo;
and wherein $R^2$ is amino; or a pharmaceutically-acceptable
salt thereof.

22. The composition of claim 21 wherein R is selected
from lower alkyl, lower hydroxyalkyl, lower haloalkyl,
lower cycloalkyl, lower cycloalkylalkyl, aryl selected from
phenyl and naphthyl, optionally substituted at a substitutable
position by halo, carboxy, lower alkyl and lower alkoxy,
lower aralkyl optionally substituted at a substitutable posi-
tion on the aryl radical by halo, carboxy, lower alkyl and
lower alkoxy, lower aryloxyalkyl optionally substituted at a
substitutable position on the aryl group with halo, carboxy,
lower alkyl and lower alkoxy, aralkoxyalkyl optionally
substituted at a substitutable position by halo, carboxy,
lower alkyl and lower alkoxy, lower heteroaryloxyalkyl
optionally substituted at a substitutable position on the
heteroaryl group with halo, carboxy, lower alkyl and lower
alkoxy, lower alkoxycarbonylalkyl, lower carboxyalkyl and
lower aminocarbonylalkyl; and wherein $R^1$ is selected from
lower cycloalkyl, lower cycloalkenyl, phenyl, naphthyl,
pyridyl, thienyl, thiazolyl, oxazolyl, imidazolyl, furyl,
quinolyl, benzothiazolyl, 2,3-thianaphthalenyl, 2,3-
dihydrothianaphthalenyl, 2,3-benzofuryl, and 2,3-
dihydrobenzofuryl, wherein $R^1$ is optionally substituted at a
substitutable position by lower alkyl, lower alkoxy and halo;
or a pharmaceutically-acceptable salt thereof.

23. The composition of claim 22 wherein R is selected
from methyl, ethyl, n-propyl, isopropyl, butyl, tert-butyl,
isobutyl, hydroxymethyl, fluoromethyl, difluoromethyl,
trifluoromethyl, chloromethyl, dichloromethyl,
trichloromethyl, pentafluoroethyl, heptafluoropropyl,
difluorochloromethyl, dichlorofluoromethyl, difluoroethyl,
difluoropropyl, dichloroethyl, dichloropropyl, cyclobutyl,
cyclopentyl, cyclohexyl, cycloheptyl, cyclobutylmethyl,
cyclopentylmethyl, cyclohexylmethyl, cyclohexylethyl,
cyclohexylpropyl, cycloheptylmethyl, aryl selected from
phenyl and naphthyl, optionally substituted at a substitutable
position by fluoro, chloro, bromo, iodo, methyl, ethyl,
n-propyl, isopropyl, butyl, tert-butyl, isobutyl, carboxy,
methoxy, ethoxy, propoxy and butoxy, benzyl, phenethyl,
diphenylmethyl and phenpropyl, optionally substituted at a
substitutable position on the phenyl group by fluoro, chloro,
bromo, iodo, methyl, ethyl, n-propyl, isopropyl, butyl, tert-
butyl, isobutyl, carboxy, methoxy, ethoxy, propoxy and
butoxy, phenoxymethyl optionally substituted at a substitut-
able position with fluoro, chloro, bromo, iodo, methyl, ethyl,
n-propyl, isopropyl, butyl, tert-butyl, isobutyl, carboxy,
methoxy, ethoxy, propoxy and butoxy, benzyloxymethyl
optionally substituted at a substitutable position by fluoro,
chloro, bromo, iodo, methyl, ethyl, n-propyl, isopropyl,
butyl, tert-butyl, isobutyl, carboxy, methoxy, ethoxy, pro-
poxy and butoxy, pyridyloxymethyl and quinolyloxymethyl,
optionally substituted at a substitutable position by fluoro,
chloro, bromo, iodo, methyl, ethyl, n-propyl, isopropyl,
butyl, tert-butyl, isobutyl, carboxy, methoxy, ethoxy, pro-
poxy and butoxy, methoxycarbonylmethyl, ethoxycarbonylmethyl, methoxycarbonylethyl, ethoxycarbonylethyl, acetyl, propanoic, butanoic, pentanoic, hexanoic and aminocarbonylmethyl; and wherein $R^1$ is selected from cyclobutyl, cyclopentyl, cyclohexyl, cycloheptyl, 1-cyclohexenyl, 2-cyclohexenyl, 3-cyclohexenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by methyl, ethyl, n-propyl, isopropyl, butyl, tert-butyl, isobutyl, methoxy, ethoxy, propoxy, butoxy, fluoro, chloro, bromo and iodo; or a pharmaceutically-acceptable salt thereof.

24. The composition of claim 23 selected from compounds, and their pharmaceutically-acceptable salts, of the group consisting of 4-[2-benzyl-5-(phenyl)oxazol-4-yl]benzenesulfonamide;
4-[2-benzyl-5-(4-fluorophenyl)oxazol-4-yl]benzenesulfonamide;
4-[2-benzyl-5-(3,4-difluorophenyl)oxazol-4-yl]benzenesulfonamide;
4-[2-benzyl-5-(4-chlorophenyl)oxazol-4-yl]benzenesulfonamide;
4-[2-benzyl-5-(3,4-dichlorophenyl)oxazol-4-yl]benzenesulfonamide;
4-[2-benzyl-5-(4-methoxyphenyl)oxazol-4-yl]benzenesulfonamide;
4-[2-benzyl-5-(3,4-dimethoxyphenyl)oxazol-4-yl]benzenesulfonamide;
4-[2-benzyl-5-(4-methylphenyl)oxazol-4-yl]benzenesulfonamide;
4-[2-benzyl-5-(3,4-dimethylphenyl)oxazol-4-yl]benzenesulfonamide;
4-[2-benzyl-5-(3-chloro-4-methylphenyl)oxazol-4-yl]benzenesulfonamide;
4-[2-benzyl-5-(4-chloro-3-methylphenyl)oxazol-4-yl]benzenesulfonamide;
4-[2-benzyl-5-(3-chloro-4-methoxyphenyl)oxazol-4-yl]benzenesulfonamide;
4-[2-benzyl-5-(4-chloro-3-methoxyphenyl)oxazol-4-yl]benzenesulfonamide;
4-[2-benzyl-5-(3,5-dichloro-4-methoxyphenyl)oxazol-4-yl]benzenesulfonamide;
4-[2-benzyl-5-(3-fluoro-4-methylphenyl)oxazol-4-yl]benzenesulfonamide;
4-[2-benzyl-5-(4-fluoro-3-methylphenyl)oxazol-4-yl]benzenesulfonamide;
4-[2-benzyl-5-(3-fluoro-4-methoxyphenyl)oxazol-4-yl]benzenesulfonamide;
4-[2-benzyl-5-(2-thienyl)oxazol-4-yl]benzenesulfonamide;
4-[2-benzyl-5-(5-chloro-2-thienyl)oxazol-4-yl]benzenesulfonamide;
4-[2-benzyl-5-(cyclohexyl)oxazol-4-yl]benzenesulfonamide;
4-[2-benzyl-5-(1-cyclohexenyl)oxazol-4-yl]benzenesulfonamide;
4-[2-(ethyl)-5-phenyloxazol-4-yl]benzenesulfonamide;
4-[2-(trifluoromethyl)-5-phenyloxazol-4-yl]benzenesulfonamide;
4-[2-(difluoromethyl)-5-phenyloxazol-4-yl]benzenesulfonamide;
4-[2-(hydroxymethyl)-5-phenyloxazol-4-yl]benzenesulfonamide;
4-[2-(carboxy)-5-phenyloxazol-4-yl]benzenesulfonamide;
4-[2-(methoxycarbonyl)-5-phenyloxazol-4-yl]benzenesulfonamide;
4-[2-(ethoxycarbonyl)-5-phenyloxazol-4-yl]benzenesulfonamide;
4-[2-(n-propyl)-5-phenyloxazol-4-yl]benzenesulfonamide;
4-[2-(benzyl)-5-phenyloxazol-4-yl]benzenesulfonamide;
4-[2-(phenoxymethyl)-5-phenyloxazol-4-yl]benzenesulfonamide;
4-[2-((4-chlorophenoxy)methyl)-5-phenyloxazol-4-yl]benzenesulfonamide;
4-[2-((4-fluorophenoxy)methyl)-5-phenyloxazol-4-yl]benzenesulfonamide;
4-[2-((4-carboxyphenoxy)methyl)-5-phenyloxazol-4-yl]benzenesulfonamide;
4-[2-(2-phenethyl)-5-phenyloxazol-4-yl]benzenesulfonamide;
4-[2-(3-phenpropyl)-5-phenyloxazol-4-yl]benzenesulfonamide;
4-[2-(carboxymethyl)-5-phenyloxazol-4-yl]benzenesulfonamide;
4-[2-(ethoxycarbonylmethyl)-5-phenyloxazol-4-yl]benzenesulfonamide;
4-[2-(methoxycarbonylmethyl)-5-phenyloxazol-4-yl]benzenesulfonamide;
4-[2-(2-quinolyloxymethyl)-5-phenyloxazol-4-yl]benzenesulfonamide;
4-[2-benzyl-4-phenyloxazol-5-yl]benzenesulfonamide;
4-[2-benzyl-4-(3,4-difluorophenyl)oxazol-5-yl]benzenesulfonamide;
4-[2-benzyl-4-(4-chlorophenyl)oxazol-5-yl]benzenesulfonamide;
4-[2-benzyl-4-(3,4-dichlorophenyl)oxazol-5-yl]benzenesulfonamide;
4-[2-benzyl-4-(4-methoxyphenyl)oxazol-5-yl]benzenesulfonamide;
4-[2-benzyl-4-(3,4-dimethoxyphenyl)oxazol-5-yl]benzenesulfonamide;
4-[2-benzyl-4-(4-methylphenyl)oxazol-5-yl]benzenesulfonamide;
4-[2-benzyl-4-(3,4-dimethylphenyl)oxazol-5-yl]benzenesulfonamide;
4-[2-benzyl-4-(3-chloro-4-methylphenyl)oxazol-5-yl]benzenesulfonamide;
4-[2-benzyl-4-(4-chloro-3-methylphenyl)oxazol-5-yl]benzenesulfonamide;
4-[2-benzyl-4-(3-chloro-4-methoxyphenyl)oxazol-5-yl]benzenesulfonamide;
4-[2-benzyl-4-(4-chloro-3-methoxyphenyl)oxazol-5-yl]benzenesulfonamide;
4-[2-benzyl-4-(3,5-dichloro-4-methoxyphenyl)oxazol-5-yl]benzenesulfonamide;
4-[2-benzyl-4-(3-fluoro-4-methylphenyl)oxazol-5-yl]benzenesulfonamide;
4-[2-benzyl-4-(4-fluoro-3-methylphenyl)oxazol-5-yl]benzenesulfonamide;
4-[2-benzyl-4-(3-fluoro-4-methoxyphenyl)oxazol-5-yl]benzenesulfonamide;
4-[2-benzyl-4-(2-thienyl)oxazol-5-yl]benzenesulfonamide;
4-[2-benzyl-4-(5-chloro-2-thienyl)oxazol-5-yl]benzenesulfonamide;
4-[2-benzyl-4-(cyclohexyl)oxazol-5-yl]benzenesulfonamide;
4-[2-benzyl-4-(1-cyclohexenyl)oxazol-5-yl]benzenesulfonamide;
4-[2-(ethyl)-4-phenyloxazol-5-yl]benzenesulfonamide;
4-[2-(trifluoromethyl)-4-phenyloxazol-5-yl]benzenesulfonamide;
4-[2-(difluoromethyl)-4-phenyloxazol-5-yl]benzenesulfonamide;

4-[2-(hydroxymethyl)-4-phenyloxazol-5-yl]benzenesulfonamide;
4-[2-(carboxy)-4-phenyloxazol-5-yl]benzenesulfonamide;
4-[2-(methoxycarbonyl)-4-phenyloxazol-5-yl]benzenesulfonamide;
4-[2-(ethoxycarbonyl)-4-phenyloxazol-5-yl]benzenesulfonamide;
4-[2-(propyl)-4-phenyloxazol-5-yl]benzenesulfonamide;
4-[2-(benzyl)-4-phenyloxazol-5-yl]benzenesulfonamide;
4-[2-(phenoxymethyl)-4-phenyloxazol-5-yl]benzenesulfonamide;
4-[2-((4-chlorophenoxy)methyl)-4-phenyloxazol-5-yl]benzenesulfonamide;
4-[2-((4-fluorophenoxy)methyl)-4-phenoxyloxazol-5-yl]benzenesulfonamide;
4-[2-((4-carboxyphenoxy)methyl)-4-phenyloxazol-5-yl]benzenesulfonamide;
4-[2-(2-phenethyl)-4-phenyloxazol-5-yl]benzenesulfonamide;
4-[2-(3-phenpropyl)-4-phenyloxazol-5-yl]benzenesulfonamide;
4-[2-(carboxymethyl)-4-phenyloxazol-5-yl]benzenesulfonamide;
4-[2-(ethoxycarbonylmethyl)-4-phenyloxazol-5-yl]benzenesulfonamide;
4-[2-(methoxycarbonylmethyl)-4-phenyloxazol-5-yl]benzenesulfonamide;
4-[2-(2-quinolyloxymethyl)-4-phenyloxazol-5-yl]benzenesulfonamide;
4-[5-(4-fluorophenyl)-2-methyl-oxazol-4-yl]benzenesulfonamide;
3-[5-(4-fluorophenyl)-4-(4-aminosulfonylphenyl)oxazol-2-yl]propanoic acid;
methyl 3-[5-(4-fluorophenyl)-4-(4-aminosulfonylphenyl)oxazol-2-yl]propanate;
4-[4-(4-fluorophenyl)-2-(2-phenylethyl)-oxazol-5-yl]benzenesulfonamide;
4-[4-(4-fluorophenyl)-2-methyl-oxazol-5-yl]benzenesulfonamide;
4-[4-(4-fluorophenyl)-2-phenyloxazol-5-yl]benzenesulfonamide;
4-[2-benzyl-4-(4-fluorophenyl)oxazol-5-yl]benzenesulfonamide;
4-[4-(4-fluorophenyl)-2-(3-phenylpropyl)oxazol-5-yl]benzenesulfonamide;
4-[4-(4-fluorophenyl)-2-(n-propyl)oxazol-5-yl]benzenesulfonamide;
4-[2-(tert-butyl)-4-(4-fluorophenyl)oxazol-5-yl]benzenesulfonamide;
4-[4-(4-fluorophenyl)-2-(4-methoxyphenyl)methyloxazol-5-yl]benzenesulfonamide;
4-[4-(4-fluorophenyl)-2-(3-methoxyphenyl)methyloxazol-5-yl]benzenesulfonamide;
4-[2-diphenylmethyl-4-(4-fluorophenyl)oxazol-5-yl]benzenesulfonamide;
2-[4-(4-fluorophenyl)-5-[4-aminosulfonylphenyl]oxazol-2-yl]acetic acid;
ethyl 2-[4-(4-fluorophenyl)-5-[4-aminosulfonylphenyl]oxazol-2-yl]acetate;
3-[4-(4-fluorophenyl)-5-[4-aminosulfonylphenyl]oxazol-2-yl]propanoic acid;
methyl 3-[4-(4-fluorophenyl)-5-[4-aminosulfonylphenyl]oxazol-2-yl]propanate;
4-[4-(4-fluorophenyl)-5-[4-aminosulfonylphenyl]oxazol-2-yl]butanoic acid;
methyl 4-[4-(4-fluorophenyl)-5-[4-aminosulfonyl phenyl]oxazol-2-yl]butanate;
3-[4-(4-fluorophenyl)-5-[4-aminosulfonyl phenyl]oxazol-2-yl]propanamide;
ethyl 2-[4-(4-fluorophenyl)-5-[4-aminosulfonyl phenyl]oxazol-2-yl]-2-benzyl-acetate;
4-[4-(4-fluorophenyl)-2-(cyclohexylethyl)oxazol-5-yl]benzenesulfonamide;
4-[4-(4-fluorophenyl)-2-(3-fluorophenoxymethyl)oxazol-5-yl]benzenesulfonamide;
4-[4-(4-fluorophenyl)-2-(3-chlorophenoxymethyl)oxazol-5-yl]benzenesulfonamide;
4-[4-(4-fluorophenyl)-2-(pyridyloxymethyl)oxazol-5-yl]benzenesulfonamide;
4-[4-(4-fluorophenyl)-2-phenoxymethyloxazol-5-yl]benzenesulfonamide;
4-[4-(4-fluorophenyl)-2-(2-hydroxyethyl)oxazol-5-yl]benzenesulfonamide;
4-[4-(4-fluorophenyl)-2-(hydroxymethyl)oxazol-5-yl]benzenesulfonamide;
4-[4-(cyclohexyl)-2-phenyloxazol-5-yl]benzenesulfonamide;
4-[4-(4-fluorophenyl)-2-benzyloxymethyloxazol-5-yl]benzenesulfonamide;
4-[4-(4-fluorophenyl)-2-cyclohexyloxazol-5-yl]benzenesulfonamide; and
4-[5-(4-fluorophenyl)-2-phenyloxazol-4-yl]benzenesulfonamide.

25. A method of treating inflammation or an inflammation-associated disorder in a subject, said method comprising administering to the subject having such inflammation or inflammation-associated disorder, a therapeutically-effective amount of a compound of Formula I

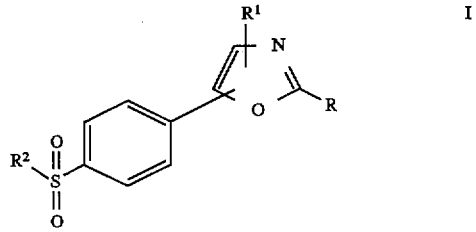

wherein R is selected from hydrido, alkyl, hydroxyalkyl, haloalkyl, alkenyl, hydroxyalkenyl, alkynyl, hydroxyalkynyl, cycloalkyl, cycloalkylalkyl, aryl optionally substituted at a substitutable position by carboxy, alkyl, alkoxy and halo, heteroaryl optionally substituted at a substitutable position by carboxy, alkyl, alkoxy and halo, aralkyl optionally substituted at a substitutable position on the aryl group by carboxy, alkyl, alkoxy and halo, aryloxyalkyl optionally substituted at a substitutable position with halo, carboxy, alkyl and alkoxy, aralkoxyalkyl optionally substituted at a substitutable position with halo, carboxy, alkyl and alkoxy, heteroaryloxyalkyl optionally substituted at a substitutable position with halo, carboxy, alkyl and alkoxy, alkoxycarbonyl, alkoxycarbonylalkyl, carboxy, carboxyalkyl, arylthioalkyl, aminocarbonylalkyl, N-alkylaminocarbonylalkyl and N,N-dialkylaminocarbonylalkyl;

wherein $R^1$ is selected from cycloalkyl, cycloalkenyl, aryl and heteroaryl, wherein $R^1$ is optionally substituted at a substitutable position by alkyl, alkoxy and halo; and wherein $R^2$ is selected from alkyl, haloalkyl and amino;

provided R is not alkyl, phenyl, aralkyl, carboxyalkyl or alkoxycarbonylalkyl, when $R^1$ is 4-fluorophenyl and when $R^2$ is methyl;

or a pharmaceutically-acceptable salt thereof.

26. The method of claim 25 wherein R is selected from hydrido, lower alkyl, lower hydroxyalkyl, lower haloalkyl, lower alkenyl, lower hydroxyalkenyl, lower alkynyl, lower hydroxyalkynyl, lower cycloalkyl, lower cycloalkylalkyl, aryl selected from phenyl and naphthyl, optionally substituted at a substitutable position by halo, carboxy, lower alkyl and lower alkoxy, heteroaryl selected from pyridyl, thienyl, thiazolyl, oxazolyl, imidazolyl, furyl and quinolyl, optionally substituted at a substitutable position by halo, carboxy, lower alkyl and lower alkoxy, lower aralkyl optionally substituted at a substitutable position on the aryl group by halo, carboxy, lower alkyl and lower alkoxy, lower aryloxyalkyl optionally substituted at a substitutable position with halo, carboxy, lower alkyl and lower alkoxy, lower heteroaryloxyalkyl optionally substituted at a substitutable position with halo, carboxy, lower alkyl and lower alkoxy, lower aralkoxyalkyl optionally substituted at a substitutable position with halo, carboxy, lower alkyl and lower alkoxy, lower alkoxycarbonyl, lower alkoxycarbonylalkyl, carboxy, lower carboxyalkyl, lower arylthioalkyl, lower aminocarbonylalkyl, lower N-alkylaminocarbonylalkyl and lower N,N-dialkylaminocarbonylalkyl; wherein $R^1$ is selected from lower cycloalkyl, lower cycloalkenyl, phenyl, naphthyl and heteroaryl selected from pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by lower alkyl, lower alkoxy and halo; and wherein $R^2$ is methyl or amino; or a pharmaceutically-acceptable salt thereof.

27. The method of claim 26 wherein R is selected from hydrido, methyl, ethyl, n-propyl, isopropyl, butyl, tert-butyl, isobutyl, hydroxymethyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, ethenyl, 1-propenyl, 2-propenyl, 1-butenyl, 2-butenyl, 3-butenyl, hydroxyethenyl, ethynyl, 1-propynyl, 2-propynyl, 1-butynyl, 2-butynyl, 3-butynyl, hydroxyethynyl, cyclobutyl, cyclopentyl, cyclohexyl, cycloheptyl, cyclobutylmethyl, cyclopentylmethyl, cyclohexylmethyl, cyclohexylethyl, cyclohexylpropyl, cycloheptylmethyl, phenyl and naphthyl, optionally substituted at a substitutable position by fluoro, chloro, bromo, iodo, carboxy, methyl, ethyl, n-propyl, isopropyl, butyl, tert-butyl, isobutyl, methoxy, ethoxy, propoxy and butoxy, pyridyl, thienyl, thiazolyl, oxazolyl, imidazolyl, furyl and quinolyl, optionally substituted at a substitutable position by fluoro, chloro, bromo, iodo, carboxy, methyl, ethyl, n-propyl, isopropyl, butyl, tert-butyl, isobutyl, methoxy, ethoxy, propoxy and butoxy, benzyl, phenethyl, diphenylmethyl and phenpropyl, optionally substituted at a substitutable position on the phenyl group by fluoro, chloro, bromo, iodo, carboxy, methyl, ethyl, n-propyl, isopropyl, butyl, tert-butyl, isobutyl, methoxy, ethoxy, propoxy and butoxy, phenoxymethyl optionally substituted at a substitutable position on the phenyl group with fluoro, chloro, bromo, iodo, carboxy, methyl, ethyl, n-propyl, isopropyl, butyl, tert-butyl, isobutyl, methoxy, ethoxy, propoxy and butoxy, benzyloxymethyl optionally substituted at a substitutable position on the phenyl group with fluoro, chloro, bromo, iodo, carboxy, methyl, ethyl, n-propyl, isopropyl, butyl, tert-butyl, isobutyl, methoxy, ethoxy, propoxy and butoxy, pyridyloxymethyl and quinolyloxymethyl optionally substituted at a substitutable position with fluoro, chloro, bromo, iodo, carboxy, methyl, ethyl, n-propyl, isopropyl, butyl, tert-butyl, isobutyl, methoxy, ethoxy, propoxy and butoxy, methoxycarbonyl, ethoxycarbonyl, propoxycarbonyl, butoxycarbonyl, methoxycarbonylmethyl, ethoxycarbonylmethyl, methoxycarbonylethyl, ethoxycarbonylethyl, carboxy, acetyl, propanoic, butanoic, pentanoic, hexanoic, phenylthiomethyl, aminocarbonylmethyl, N-methylaminocarbonylmethyl and N,N-dimethylaminocarbonylmethyl; wherein $R^1$ is selected from cyclobutyl, cyclopentyl, cyclohexyl, cycloheptyl, 1-cyclohexenyl, 2-cyclohexenyl, 3-cyclohexenyl, cyclopentenyl, cycloheptenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by methyl, ethyl, n-propyl, isopropyl, butyl, tert-butyl, isobutyl, methoxy, ethoxy, propoxy, butoxy, fluoro, chloro, bromo and iodo; and wherein $R^2$ is methyl or amino; or a pharmaceutically-acceptable salt thereof.

28. The method of claim 27 selected from compounds and their pharmaceutically-acceptable salts, of the group consisting of 4-[2-benzyl-5-(phenyl)oxazol-4-yl]benzenesulfonamide;
4-[2-benzyl-5-(4-fluorophenyl)oxazol-4-yl] benzenesulfonamide;
4-[2-benzyl-5-(3,4-difluorophenyl)oxazol-4-yl] benzenesulfonamide;
4-[2-benzyl-5-(4-chlorophenyl)oxazol-4-yl] benzenesulfonamide;
4-[2-benzyl-5-(3,4-dichlorophenyl)oxazol-4-yl] benzenesulfonamide;
4-[2-benzyl-5-(4-methoxyphenyl)oxazol-4-yl] benzenesulfonamide;
4-[2-benzyl-5-(3,4-dimethoxyphenyl)oxazol-4-yl] benzenesulfonamide;
4-[2-benzyl-5-(4-methylphenyl)oxazol-4-yl] benzenesulfonamide;
4-[2-benzyl-5-(3,4-dimethylphenyl)oxazol-4-yl] benzenesulfonamide;
4-[2-benzyl-5-(3-chloro-4-methylphenyl)oxazol-4-yl] benzenesulfonamide;
4-[2-benzyl-5-(4-chloro-3-methylphenyl)oxazol-4-yl] benzenesulfonamide;
4-[2-benzyl-5-(3-chloro-4-methoxyphenyl)oxazol-4-yl] benzenesulfonamide;
4-[2-benzyl-5-(4-chloro-3-methoxyphenyl)oxazol-4-yl] benzenesulfonamide;
4-[2-benzyl-5-(3,5-dichloro-4-methoxyphenyl)oxazol-4-yl] benzenesulfonamide;
4-[2-benzyl-5-(3-fluoro-4-methylphenyl)oxazol-4-yl] benzenesulfonamide;
4-[2-benzyl-5-(4-fluoro-3-methylphenyl)oxazol-4-yl] benzenesulfonamide;
4-[2-benzyl-5-(3-fluoro-4-methoxyphenyl)oxazol-4-yl] benzenesulfonamide;
4-[2-benzyl-5-(2-thienyl)oxazol-4-yl]benzenesulfonamide;
4-[2-benzyl-5-(5-chloro-2-thienyl)oxazol-4-yl] benzenesulfonamide;
4-[2-benzyl-5-(cyclohexyl)oxazol-4-yl] benzenesulfonamide;
4-[2-benzyl-5-(1-cyclohexenyl)oxazol-4-yl] benzenesulfonamide;
2-benzyl-4-(4-methylsulfonylphenyl)-5-phenyloxazole;
2-benzyl-4-(4-methylsulfonylphenyl)-5-(3,4-difluorophenyl)oxazole;

2-benzyl-4-(4-methylsulfonylphenyl)-5-(4-chlorophenyl)
oxazole;
2-benzyl-4-(4-methylsulfonylphenyl)-5-(3,4-
dichlorophenyl)oxazole;
2-benzyl-4-(4-methylsulfonylphenyl)-5-(4-methoxyphenyl)
oxazole;
2-benzyl-4-(4-methylsulfonylphenyl)-5-(3,4-
dimethoxyphenyl)oxazole;
2-benzyl-4-(4-methylsulfonylphenyl)-5-(4-methylphenyl)
oxazole;
2-benzyl-4-(4-methylsulfonylphenyl)-5-(3,4-
dimethylphenyl)oxazole;
2-benzyl-4-(4-methylsulfonylphenyl)-5-(3-chloro-4-
methylphenyl)oxazole;
2-benzyl-4-(4-methylsulfonylphenyl)-5-(4-chloro-3-
methylphenyl)oxazole;
2-benzyl-4-(4-methylsulfonylphenyl)-5-(3-chloro-4-
methoxyphenyl)oxazole;
2-benzyl-4-(4-methylsulfonylphenyl)-5-(4-chloro-3-
methoxyphenyl)oxazole;
2-benzyl-4-(4-methylsulfonylphenyl)-5-(3,5-dichloro-4-
methoxyphenyl)oxazole;
2-benzyl-4-(4-methylsulfonylphenyl)-5-(3-fluoro-4-
methylphenyl)oxazole;
2-benzyl-4-(4-methylsulfonylphenyl)-5-(4-fluoro-3-
methylphenyl)oxazole;
2-benzyl-4-(4-methylsulfonylphenyl)-5-(3-fluoro-4-
methoxyphenyl)oxazole;
2-benzyl-4-(4-methylsulfonylphenyl)-5-(2-thienyl)oxazole;
2-benzyl-4-(4-methylsulfonylphenyl)-5-(5-chloro-2-
thienyl)oxazole;
2-benzyl-4-(4-methylsulfonylphenyl)-5-(cyclohexyl)
oxazole-;
2-benzyl-4-(4-methylsulfonylphenyl)-5-(1-cyclohexenyl)
oxazole;
2-(ethyl)-4-(4-methylsulfonylphenyl)-5-phenyloxazole;
2-(trifluoromethyl)-4-(4-methylsulfonylphenyl)-5-
phenyloxazole;
2-(difluoromethyl)-4-(4-methylsulfonylphenyl)-5-
phenyloxazole;
2-(hydroxymethyl)-4-(4-methylsulfonylphenyl)-5-
phenyloxazole;
2-(carboxy)-4-(4-methylsulfonylphenyl)-5-phenyloxazole;
2-(methoxycarbonyl)-4-(4-methylsulfonylphenyl)-5-
phenyloxazole;
2-(ethoxycarbonyl)-4-(4-methylsulfonylphenyl)-5-
phenyloxazole;
2-(propyl)-4-(4-methylsulfonylphenyl)-5-phenyloxazole;
2-(benzyl)-4-(4-methylsulfonylphenyl)-5-phenyloxazole;
2-(phenoxymethyl)-4-(4-methylsulfonylphenyl)-5-
phenyloxazole;
2-((4-chlorophenoxy)methyl)-4-(4-methylsulfonylphenyl)-
5-phenyloxazole;
2-((4-fluorophenoxy)methyl)-4-(4-methylsulfonylphenyl)-
5-phenyloxazole;
2-((4-carboxyphenoxy)methyl)-4-(4-methylsulfonylphenyl)
-5-phenyloxazole;
2-(2-phenethyl)-4-(4-methylsulfonylphenyl)-5-
phenyloxazole;
2-(3-phenpropyl)-4-(4-methylsulfonylphenyl)-5-
phenyloxazole;
2-(carboxymethyl)-4-(4-methylsulfonylphenyl)-5-
phenyloxazole;
2-(ethoxycarbonylmethyl)-4-4-methylsulfonylphenyl)-5-
phenyloxazole;
2-(methoxycarbonylmethyl)-4-(4-methylsulfonylphenyl)-5-
phenyloxazole;
2-(2-quinolyloxymethyl)-4-(4-methylsulfonylphenyl)-5-
phenyloxazole;
4-[2-(ethyl)-5-phenyloxazol-4-yl]benzenesulfonamide;
4-[2-(trifluoromethyl)-5-phenyloxazol-4-yl]
benzenesulfonamide;
4-[2-(difluoromethyl)-5-phenyloxazol-4-yl]
benzenesulfonamide;
4-[2-(hydroxymethyl)-5-phenyloxazol-4-yl]
benzenesulfonamide;
4-[2-(carboxy)-5-phenyloxazol-4-yl]benzenesulfonamide;
4-[2-(methoxycarbonyl)-5-phenyloxazol-4-yl]
benzenesulfonamide;
4-[2-(ethoxycarbonyl)-5-phenyloxazol-4-yl]
benzenesulfonamide;
4-[2-(propyl)-5-phenyloxazol-4-yl]benzenesulfonamide;
4-[2-(benzyl)-5-phenyloxazol-4-yl]benzenesulfonamide;
4-[2-(phenoxymethyl)-5-phenyloxazol-4-yl]
benzenesulfonamide;
4-[2-((4-chlorophenoxy)methyl)-5-phenyloxazol-4-yl]
benzenesulfonamide;
4-[2-((4-fluorophenoxy)methyl)-5-phenyloxazol-4-yl]
benzenesulfonamide;
4-[2-((4-carboxyphenoxy)methyl)-5-phenyloxazol-4-yl]
benzenesulfonamide;
4-[2-(2-phenethyl)-5-phenyloxazol-4-yl]
benzenesulfonamide;
4-[2-(3-phenpropyl)-5-phenyloxazol-4-yl]
benzenesulfonamide;
4-[2-(carboxymethyl)-5-phenyloxazol-4-yl]
benzenesulfonamide;
4-[2-(ethoxycarbonylmethyl)-5-phenyloxazol-4-yl]
benzenesulfonamide;
4-[2-(methoxycarbonylmethyl)-5-phenyloxazol-4-yl]
benzenesulfonamide;
4-[2-(2-quinolyloxymethyl)-5-phenyloxazol-4-yl]
benzenesulfonamide;
4-[2-benzyl-4-phenyloxazol-5-yl]benzenesulfonamide;
4-[2-benzyl-4-(4-fluorophenyl)oxazol-5-yl]
benzenesulfonamide;
4-[2-benzyl-4-(3,4-difluorophenyl)oxazol-5-yl]
benzenesulfonamide;
4-[2-benzyl-4-(4-chlorophenyl)oxazol-5-yl]
benzenesulfonamide;
4-[2-benzyl-4-(3,4-dichlorophenyl)oxazol-5-yl]
benzenesulfonamide;
4-[2-benzyl-4-(4-methoxyphenyl)oxazol-5-yl]
benzenesulfonamide;
4-[2-benzyl-4-(3,4-dimethoxyphenyl)oxazol-5-yl]
benzenesulfonamide;
4-[2-benzyl-4-(4-methylphenyl)oxazol-5-yl]
benzenesulfonamide;
4-[2-benzyl-4-(3,4-dimethylphenyl)oxazol-5-yl]
benzenesulfonamide;
4-[2-benzyl-4-(3-chloro-4-methylphenyl)oxazol-5-yl]
benzenesulfonamide;
4-[2-benzyl-4-(4-chloro-3-methylphenyl)oxazol-5-yl]
benzenesulfonamide;
4-[2-benzyl-4-(3-chloro-4-methoxyphenyl)oxazol-5-yl]
benzenesulfonamide;
4-[2-benzyl-4-(4-chloro-3-methoxyphenyl)oxazol-5-yl]
benzenesulfonamide;
4-[2-benzyl-4-(3,5-dichloro-4-methoxyphenyl)oxazol-5-yl]
benzenesulfonamide;
4-[2-benzyl-4-(3-fluoro-4-methylphenyl)oxazol-5-yl]
benzenesulfonamide;
4-[2-benzyl-4-(4-fluoro-3-methylphenyl)oxazol-5-yl]
benzenesulfonamide;

4-[2-benzyl-4-(3-fluoro-4-methoxyphenyl)oxazol-5-yl]benzenesulfonamide;
4-[2-benzyl-4-(2-thienyl)oxazol-5-yl]benzenesulfonamide;
4-[2-benzyl-4-(5-chloro-2-thienyl)oxazol-5-yl]benzenesulfonamide;
4-[2-benzyl-4-(cyclohexyl)oxazol-5-yl]benzenesulfonamide;
4-[2-benzyl-4-(1-cyclohexenyl)oxazol-5-yl]benzenesulfonamide;
2-benzyl-5-(4-methylsulfonylphenyl)-4-phenyloxazole;
2-benzyl-5-(4-methylsulfonylphenyl)-4-(3,4-difluorophenyl)oxazole;
2-benzyl-5-4-methylsulfonylphenyl)-4-(4-chlorophenyl)oxazol-4-yl]benzenesulfonamide;
2-benzyl-5-4-methylsulfonylphenyl)-4-(3,4-dichlorophenyl)oxazole;
2-benzyl-5-4-methylsulfonylphenyl)-4-(4-methoxyphenyl)oxazole;
2-benzyl-5-4-methylsulfonylphenyl)-4-(3,4-dimethoxyphenyl)oxazole;
2-benzyl-5-4-methylsulfonylphenyl)-4-(4-methylphenyl)oxazole;
2-benzyl-5-4-methylsulfonylphenyl)-4-(3,4-dimethylphenyl)oxazole;
2-benzyl-5-4-methylsulfonylphenyl)-4-(3-chloro-4-methylphenyl)oxazole;
2-benzyl-5-(4-methylsulfonylphenyl)-4-(4-chloro-3-methylphenyl)oxazole;
2-benzyl-5-(4-methylsulfonylphenyl)-4-(3-chloro-4-methoxyphenyl)oxazole;
2-benzyl-5-(4-methylsulfonylphenyl)-4-(4-chloro-3-methoxyphenyl)oxazole;
2-benzyl-5-(4-methylsulfonylphenyl)-4-(3,5-dichloro-4-methoxyphenyl)oxazole;
2-benzyl-5-(4-methylsulfonylphenyl)-4-(3-fluoro-4-methylphenyl)oxazole;
2-benzyl-5-(4-methylsulfonylphenyl)-4-(4-fluoro-3-methylphenyl)oxazole;
2-benzyl-5-(4-methylsulfonylphenyl)-4-(3-fluoro-4-methoxyphenyl)oxazole;
2-benzyl-5-(4-methylsulfonylphenyl)-4-(2-thienyl)oxazole;
2-benzyl-5-(4-methylsulfonylphenyl)-4-(5-chloro-2-thienyl)oxazole;
2-benzyl-5-(4-methylsulfonylphenyl)-4-(cyclohexyl)oxazole-;
2-benzyl-5-(4-methylsulfonylphenyl)-4-(2-cyclohexenyl)oxazole;
2-(ethyl)-5-(4-methylsulfonylphenyl)-4-phenyloxazole;
2-(trifluoromethyl)-5-(4-methylsulfonylphenyl)-4-phenyloxazole;
2-(difluoromethyl)-5-(4-methylsulfonylphenyl)-4-phenyloxazole;
2-(hydroxymethyl)-5-(4-methylsulfonylphenyl)-4-phenyloxazole;
2-(carboxy)-5-(4-methylsulfonylphenyl)-4-phenyloxazole;
2-(methoxycarbonyl)-5-(4-methylsulfonylphenyl)-4-phenyloxazole;
2-(ethoxycarbonyl)-5-(4-methylsulfonylphenyl)-4-phenyloxazole;
2-(propyl)-5-(4-methylsulfonylphenyl)-4-phenyloxazole;
2-(benzyl)-5-(4-methylsulfonylphenyl)-4-phenyloxazole;
2-(phenoxymethyl)-5-(4-methylsulfonylphenyl)-4-phenyloxazole;
2-((4-chlorophenoxy)methyl)-5-(4-methylsulfonylphenyl)-4-phenyloxazole;
2-((4-fluorophenoxy)methyl)-5-(4-methylsulfonylphenyl)-4-phenyloxazole;
2-((4-carboxyphenoxy)methyl)-5-(4-methylsulfonylphenyl)-4-phenyloxazole;
2-(2-phenethyl)-5-(4-methylsulfonylphenyl)-4-phenyloxazole;
2-(3-phenpropyl)-5-(4-methylsulfonylphenyl)-4-phenyloxazole;
2-(carboxymethyl)-5-(4-methylsulfonylphenyl)-4-phenyloxazole;
2-(ethoxycarbonylmethyl)-5-(4-methylsulfonylphenyl)-4-phenyloxazole;
2-(methoxycarbonylmethyl)-5-(4-methylsulfonylphenyl)-4-phenyloxazole;
2-(2-quinolyloxymethyl)-5-(4-methylsulfonylphenyl)-4-phenyloxazole;
4-[2-(ethyl)-4-phenyloxazol-5-yl]benzenesulfonamide;
4-[2-(trifluoromethyl)-4-phenyloxazol-5-yl]benzenesulfonamide;
4-[2-(difluoromethyl)-4-phenyloxazol-5-yl]benzenesulfonamide;
4-[2-(hydroxymethyl)-4-phenyloxazol-5-yl]benzenesulfonamide;
4-[2-(carboxy)-4-phenyloxazol-5-yl]benzenesulfonamide;
4-[2-(methoxycarbonyl)-4-phenyloxazol-5-yl]benzenesulfonamide;
4-[2-(ethoxycarbonyl)-4-phenyloxazol-5-yl]benzenesulfonamide;
4-[2-(propyl)-4-phenyloxazol-5-yl]benzenesulfonamide;
4-[2-(benzyl)-4-phenyloxazol-5-yl]benzenesulfonamide;
4-[2-(phenoxymethyl)-4-phenyloxazol-5-yl]benzenesulfonamide;
4-[2-((4-chlorophenoxy)methyl)-4-phenyloxazol-5-yl]benzenesulfonamide;
4-[2-((4-fluorophenoxy)methyl)-4-phenyloxazol-5-yl]benzenesulfonamide;
4-[2-((4-carboxyphenoxy)methyl)-4-phenyloxazol-5-yl]benzenesulfonamide;
4-[2-(2-phenethyl)-4-phenyloxazol-5-yl]benzenesulfonamide;
4-[2-(3-phenpropyl)-4-phenyloxazol-5-yl]benzenesulfonamide;
4-[2-(carboxymethyl)-4-phenyloxazol-5-yl]benzenesulfonamide;
4-[2-(ethoxycarbonylmethyl)-4-phenyloxazol-5-yl]benzenesulfonamide;
4-[2-(methoxycarbonylmethyl)-4-phenyloxazol-5-yl]benzenesulfonamide;
4-[2-(2-quinolyloxymethyl)-4-phenyloxazol-5-yl]benzenesulfonamide;
5-(4-fluorophenyl)-2-methyl-4-[4-(methylsulfonyl)phenyl]oxazole;
3-[5-(4-fluorophenyl)-4-[4-(methylsulfonyl)phenyl]oxazol-2-yl]propanoic acid;
methyl 3-[5-(4-fluorophenyl)-4-[4-(methylsulfonyl)phenyl]oxazol-2-yl]propanate;
4-(4-fluorophenyl)-2-(2-phenyl)ethyl-5-(4-(methylsulfonyl)phenyl)oxazole;
4-(4-fluorophenyl)-2-methyl-5-[4-(methylsulfonylphenyl]oxazole;
4-(4-fluorophenyl)-5-[4-(methylsulfonyl)phenyl]-2-phenyloxazole;
2-benzyl-4-(4-fluorophenyl)-5-(4-(methylsulfonyl)phenyl)oxazole;
4-(4-fluorophenyl)-5-[4-methylsulfonylphenyl]-2-(3-phenyl)propyloxazole;
4-(4-fluorophenyl)-5-[4-methylsulfonylphenyl]-2-propyloxazole;
2-(tert-butyl)-4-(4-fluorophenyl)-5-[4-methylsulfonylphenyl]oxazole;

2-(4-fluorophenyl)-2-(4-methoxyphenyl)methyl-5-[4-methylsulfonylphenyl]oxazole 4-(4-fluorophenyl)-2-(3-methoxyphenyl)methyl-5-[4methylsulfonylphenyl]oxazole;

2-diphenylmethyl-4-(4-fluorophenyl)-5-[4-methylsulfonylphenyl]oxazole;

2-[4-(4-fluorophenyl)-5-[4-methylsulfonylphenyl]oxazol-2-yl]acetic acid;

ethyl 2-[4-(4-fluorophenyl)-5-[4-methylsulfonyl)phenyl]oxazol-2-yl]acetate;

3-[4-(4-fluorophenyl)-5-[4-methylsulfonyl)phenyl]oxazol-2-yl]propanoic acid;

methyl 3-[4-(4-fluorophenyl)-5-[4-methylsulfonyl)phenyl]oxazol-2-yl]propanate;

4-[4-(4-fluorophenyl)-5-[4-methylsulfonyl)phenyl]oxazol-2-yl]butanoic acid;

methyl 4-[4-(4-fluorophenyl)-5-[4-methylsulfonyl)phenyl]oxazol-2-yl]butanate;

3-[4-(4-fluorophenyl)-5-[4-methylsulfonyl)phenyl]oxazol-2-yl]propanamide;

ethyl 2-[4-(4-fluorophenyl)-5-[4-(methylsulfonyl)phenyl]oxazol-2-yl]-2-benzyl-acetate;

4-(4-fluorophenyl)-2-(cyclohexylethyl)-5-[4-(methylsulfonyl)phenyl]oxazole;

4-(4-fluorophenyl)-2-(3-fluorophenoxymethyl)-5-[4-(methylsulfonyl)phenyl]oxazole;

4-(4-fluorophenyl)-2-(3-chlorophenoxymethyl)-5-[4-(methylsulfonyl)phenyl]oxazole;

4-(4-fluorophenyl)-2-(pyridyloxymethyl)-5-[4-(methylsulfonyl)phenyl]oxazole;

4-(4-fluorophenyl)-5-[4-(methylsulfonyl)phenyl]-2-phenoxymethyloxazole;

4-(4-fluorophenyl)-2-(2-hydroxyethyl)-5-[4-(methylsulfonyl)phenyl]oxazole;

4-(4-fluorophenyl)-2-(hydroxymethyl)-5-[4-(methylsulfonyl)phenyl]oxazole;

4-(cyclohexyl)-2-phenyl-5-[4-(methylsulfonyl)phenyl]oxazole;

4-(4-fluorophenyl)-2-benzyloxymethyl-5-[4-(methylsulfonyl)phenyl]oxazole;

4-(4-fluorophenyl)-2-cyclohexyl-5-[4-(methylsulfonyl)phenyl]oxazole; and 5-(4-fluorophenyl)-2-phenyl-4-[4-(methylsulfonyl)phenyl]oxazole.

29. The method of claim 25 wherein R is selected from alkyl, hydroxyalkyl, haloalkyl, cycloalkyl, cycloalkylalkyl, aryl optionally substituted at a substitutable position by carboxy, alkyl, alkoxy and halo, aralkyl optionally substituted at a substitutable position on the aryl group by carboxy, alkyl, alkoxy and halo, aryloxyalkyl optionally substituted at a substitutable position on the aryl group with halo, carboxy, alkyl and alkoxy, aralkoxyalkyl optionally substituted at a substitutable position by alkyl, carboxy, alkoxy and halo, heteroaryloxyalkyl optionally substituted at a substitutable position on the heteroaryl group with halo, carboxy, alkyl and alkoxy, alkoxycarbonylalkyl, carboxyalkyl and aminocarbonylalkyl; wherein $R^1$ is selected from cycloalkyl, cycloalkenyl, heteroaryl and aryl optionally substituted at a substitutable position by alkyl, alkoxy and halo, and wherein $R^2$ is methyl; or a pharmaceutically-acceptable salt thereof.

30. The method of claim 29 wherein R is selected from lower alkyl, lower hydroxyalkyl, lower haloalkyl, lower cycloalkyl, lower cycloalkylalkyl, aryl selected from phenyl and naphthyl, optionally substituted at a substitutable position by halo, carboxy, lower alkyl and lower alkoxy, lower aralkyl optionally substituted at a substitutable position on the aryl group by halo, carboxy, lower alkyl and lower alkoxy, lower aryloxyalkyl optionally substituted at a substitutable position on the aryl group with halo, carboxy, lower alkyl and lower alkoxy, aralkoxyalkyl optionally substituted at a substitutable position by halo, carboxy, lower alkyl and lower alkoxy, lower heteroaryloxyalkyl optionally substituted at a substitutable position on the heteroaryl group with halo, carboxy, lower alkyl and lower alkoxy, lower alkoxycarbonylalkyl, lower carboxyalkyl and lower aminocarbonylalkyl; and wherein $R^1$ is selected from lower cycloalkyl, lower cycloalkenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by lower alkyl, lower alkoxy and halo; or a pharmaceutically-acceptable salt thereof.

31. The method of claim 30 wherein R is selected from methyl, ethyl, n-propyl, isopropyl, butyl, tert-butyl, isobutyl, hydroxymethyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyclobutyl, cyclopentyl, cyclohexyl, cycloheptyl, cyclobutylmethyl, cyclopentylmethyl, cyclohexylmethyl, cyclohexylethyl, cyclohexylpropyl, cycloheptylmethyl, aryl selected from phenyl and naphthyl, optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, benzyl, phenethyl, diphenylmethyl and phenpropyl, optionally substituted at a substitutable position on the phenyl group by fluoro, chloro, bromo, iodo, methyl, ethyl, n-propyl, isopropyl, butyl, tert-butyl, isobutyl, carboxy, methoxy, ethoxy, propoxy and butoxy, phenoxymethyl optionally substituted at a substitutable position with fluoro, chloro, bromo, iodo, methyl, ethyl, n-propyl, isopropyl, butyl, tert-butyl, isobutyl, carboxy, methoxy, ethoxy, propoxy and butoxy, benzyloxymethyl optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, pyridyloxymethyl and quinolyloxymethyl, optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, methoxycarbonylmethyl, ethoxycarbonylmethyl, methoxycarbonylethyl, ethoxycarbonylethyl, acetyl, propanoic, butanoic, pentanoic, hexanoic and aminocarbonylmethyl; and wherein $R^1$ is selected from cyclobutyl, cyclopentyl, cyclohexyl, cycloheptyl, 1-cyclohexenyl, 2-cyclohexenyl, 3-cyclohexenyl, phenyl, naphthyl, pyridyl, thienyl, thiazolyl, oxazolyl, imidazolyl, furyl, quinolyl, benzothiazolyl, 2,3-thianaphthalenyl, 2,3dihydrothianaphthalenyl, 2,3-benzofuryl, and 2,3-dihydrobenzofuryl, wherein $R^1$ is optionally substituted at a substitutable position by methyl, ethyl, n-propyl, isopropyl, butyl, tert-butyl, isobutyl, methoxy, ethoxy, propoxy, butoxy, fluoro, chloro, bromo and iodo; or a pharmaceutically-acceptable salt thereof.

32. The method of claim 31 selected from compounds and their pharmaceutically-acceptable salts, of the group consisting of 5-(4-fluorophenyl)-2-methyl-4-[4-(methylsulfonyl)phenyl] oxazole; -

5(4-fluorophenyl)-4-[4-(methylsulfonyl)phenyl]-2-oxazol-2-yl]propanoic acid;

methyl 3-[5-(4-fluorophenyl)-4-[4-(methylsulfonyl)phenyl]
-2-oxazol-2-yl]propanate;
4-(4-fluorophenyl)-2-(2-phenylethyl)-5-(4-(methylsulfonyl)
phenyl)oxazole;
4-(4-fluorophenyl)-2-methyl-5-[4-methylsulfonylphenyl]
oxazole;
4-(4-fluorophenyl)-5-[4-(methylsulfonyl)phenyl]-2-
phenyloxazole;
2-benzyl-4-(4-fluorophenyl)-5-(4-(methylsulfonyl)phenyl)
oxazole;
4-(4-fluorophenyl)-5-[4-methylsulfonylphenyl]-2-(3-
phenyl)propyloxazole;
4-(4-fluorophenyl)-5-[4-methylsulfonylphenyl]-2-
propyloxazole;
2-(tert-butyl)-4-(4-fluorophenyl)-5-[4-
methylsulfonylphenyl]oxazole;
4-(4-fluorophenyl)-2-(4-methoxyphenyl)methyl-5-[4-
methylsulfonylphenyl]oxazole
4-(4-fluorophenyl)-2-(3-methoxyphenyl)methyl-5-[4-
methylsulfonylphenyl]oxazole;
2-diphenylmethyl-4-(4-fluorophenyl)-5-[4-
methylsulfonylphenyl]oxazole;
2-[4-(4-fluorophenyl)-5-[4-methylsulfonylphenyl]oxazol-2-
yl]acetic acid;
ethyl 2-[4-(4-fluorophenyl)-5-[4-methylsulfonyl phenyl]
oxazol-2-yl]acetate;
3-[4-(4-fluorophenyl)-5-[4-methylsulfonylphenyl]oxazol-2-
yl]propanoic acid;
methyl 3-[4-(4-fluorophenyl)-5-[4-methylsulfonyl phenyl]
oxazol-2-yl]propanate;
4-[4-(4-fluorophenyl)-5-[4-methylsulfonylphenyl]oxazol-2-
yl]butanoic acid;
methyl 4-[4-(4-fluorophenyl)-5-[4-methylsulfonyl phenyl]
oxazol-2-yl]butanate;
3-[3-(4-fluorophenyl)-5-[4-methylsulfonylphenyl]oxazol-2-
yl]propanamide;
ethyl 2-[4-(4-fluorophenyl)-5-[4-(methylsulfonyl)phenyl]
oxazol-2-yl]-2-benzyl acetate;
4-(4-fluorophenyl)-2-(cyclohexylethyl)-5-[4-
(methylsulfonyl)phenyl]oxazole;
4-(4-fluorophenyl)-2-(3-fluorophenoxymethyl)-5-[4-
(methylsulfonyl)phenyl]oxazole;
4-(4-fluorophenyl)-2-(3-chlorophenoxymethyl)-5-[4-
(methylsulfonyl)phenyl]oxazole;
4-(4-fluorophenyl)-2-(pyridyloxymethyl)-5-[4-
(methylsulfonyl)phenyl]oxazole;
4-(4-fluorophenyl)-5-[4-(methylsulfonyl)phenyl]-2-
phenoxymethyl oxazole;
4-(4-fluorophenyl)-2-(2-hydroxy)ethyl)-5-[4-
(methylsulfonyl)phenyl]oxazole;
4-(4-fluorophenyl)-2-(hydroxymethyl)-5-[4-
(methylsulfonyl)phenyl]oxazole;
4-(cyclohexyl)-2-phenyl-5-[4-(methylsulfonyl)phenyl]
oxazole;
4-(4-fluorophenyl)-2-benzyloxymethyl-5-[4-
(methylsulfonyl)phenyl]oxazole;
4-(4-fluorophenyl)-2-cyclohexyl-5-[4-(methylsulfonyl)
phenyl]oxazole; and
5-(4-fluorophenyl)-2-phenyl-4-[4-(methylsulfonyl)phenyl]
oxazole.

34. The method of claim 25 wherein R is selected from alkyl, hydroxyalkyl, haloalkyl, cycloalkyl, cycloalkylalkyl, aryl optionally substituted at a substitutable position by carboxy, alkyl, alkoxy and halo, aralkyl optionally substituted at a substitutable position on the aryl group by carboxy, alkyl, alkoxy and halo, aryloxyalkyl optionally substituted at a substitutable position on the aryl group with halo, carboxy, alkyl and alkoxy, aralkoxyalkyl optionally substituted at a substitutable position by alkyl, carboxy, alkoxy and halo, heteroaryloxyalkyl optionally substituted at a substitutable position on the heteroaryl group with halo, carboxy, alkyl and alkoxy, alkoxycarbonylalkyl, carboxyalkyl and aminocarbonylalkyl; wherein $R^1$ is selected cycloalkyl, cycloalkenyl, heteroaryl and aryl optionally substituted at a substitutable position by alkyl, alkoxy and halo; and wherein $R^2$ is amino; or a pharmaceutically-acceptable salt thereof; provided R is not methyl.

34. The method of claim 33 wherein R is selected from lower alkyl, lower hydroxyalkyl, lower haloalkyl, lower cycloalkyl, lower cycloalkylalkyl, aryl selected from phenyl and naphthyl, optionally substituted at a substitutable position by halo, carboxy, lower alkyl and lower alkoxy, lower aralkyl optionally substituted at a substitutable position on the aryl group by halo, carboxy, lower alkyl and lower alkoxy, lower aryloxyalkyl optionally substituted at a substitutable position on the aryl group with halo, carboxy, lower alkyl and lower alkoxy, aralkoxyalkyl optionally substituted at a substitutable position by halo, carboxy, lower alkyl and lower alkoxy, lower heteroaryloxyalkyl optionally substituted at a substitutable position on the heteroaryl group with halo, carboxy, lower alkyl and lower alkoxy, lower alkoxycarbonylalkyl, lower carboxyalkyl and lower aminocarbonylalkyl; and wherein $R^1$ is selected from lower cycloalkyl, lower cycloalkenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by lower alkyl, lower alkoxy and halo; or a pharmaceutically-acceptable salt thereof.

35. The method of claim 34 wherein R is selected from methyl, ethyl, n-propyl, isopropyl, butyl, tert-butyl, isobutyl, hydroxymethyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, cyclobutyl, cyclopentyl, cyclohexyl, cycloheptyl, cyclobutylmethyl, cyclopentylmethyl, cyclohexylmethyl, cyclohexylethyl, cyclohexylpropyl, cycloheptylmethyl, aryl selected from phenyl and naphthyl, optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, benzyl, phenethyl, diphenylmethyl and phenpropyl, optionally substituted at a substitutable position on the phenyl group by fluoro, chloro, bromo, iodo, methyl, ethyl, n-propyl, isopropyl, butyl, tert-butyl, isobutyl, carboxy, methoxy, ethoxy, propoxy and butoxy, phenoxymethyl optionally substituted at a substitutable position with fluoro, chloro, bromo, iodo, methyl, ethyl, n-propyl, isopropyl, butyl, tert-butyl, isobutyl, carboxy, methoxy, ethoxy, propoxy and butoxy, benzyloxymethyl optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, pyridyloxymethyl and quinolyloxymethyl, optionally substituted at a substitutable position by fluoro, chloro, bromo, iodo, methyl, ethyl, n-propyl, isopropyl, butyl, tert-butyl, isobutyl, carboxy, methoxy, ethoxy, propoxy and butoxy, methoxycarbonylmethyl, ethoxycarbonylmethyl, methoxycarbonylethyl, ethoxycarbonylethyl, acetyl, propanoic, butanoic, pentanoic, hexanoic and aminocarbonylmethyl; and wherein $R^1$ is selected from cyclobutyl, cyclopentyl, cyclohexyl, cycloheptyl, 1-cyclohexenyl, 2-cyclohexenyl, 3-cyclohexenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by methyl, ethyl, n-propyl, isopropyl, butyl, tert-butyl, isobutyl, methoxy, ethoxy, propoxy, butoxy, fluoro, chloro, bromo and iodo; or a pharmaceutically-acceptable salt thereof.

36. Compound of claim 35 selected from compounds, and their pharmaceutically-acceptable salts, of the group consisting of 4-[2-benzyl-5-(phenyl)oxazol-4-yl]benzenesulfonamide;
4-[2-benzyl-5-(4-fluorophenyl)oxazol-4-yl]benzenesulfonamide;
4-[2-benzyl-5-(3,4-difluorophenyl)oxazol-4-yl]benzenesulfonamide;
4-[2-benzyl-5-(4-chlorophenyl)oxazol-4-yl]benzenesulfonamide;
4-[2-benzyl-5-(3,4-dichlorophenyl)oxazol-4-yl]benzenesulfonamide;
4-[2-benzyl-5-(4-methoxyphenyl)oxazol-4-yl]benzenesulfonamide;
4-[2-benzyl-5-(3,4-dimethoxyphenyl)oxazol-4-yl]benzenesulfonamide;
4-[2-benzyl-5-(4-methylphenyl)oxazol-4-yl]benzenesulfonamide;
4-[2-benzyl-5-(3,4-dimethylphenyl)oxazol-4-yl]benzenesulfonamide;
4-[2-benzyl-5-(3-chloro-4-methylphenyl)oxazol-4-yl]benzenesulfonamide;
4-[2-benzyl-5-(4-chloro-3-methylphenyl)oxazol-4-yl]benzenesulfonamide;
4-[2-benzyl-5-(3-chloro-4-methoxyphenyl)oxazol-4-yl]benzenesulfonamide;
4-[2-benzyl-5-(4-chloro-3-methoxyphenyl)oxazol-4-yl]benzenesulfonamide;
4-[2-benzyl-5-(3,5-dichloro-4-methoxyphenyl)oxazol-4-yl]benzenesulfonamide;
4-[2-benzyl-5-(3-fluoro-4-methylphenyl)oxazol-4-yl]benzenesulfonamide;
4-[2-benzyl-5-(4-fluoro-3-methylphenyl)oxazol-4-yl]benzenesulfonamide;
4-[2-benzyl-5-(3-fluoro-4-methoxyphenyl)oxazol-4-yl]benzenesulfonamide;
4-[2-benzyl-5-(2-thienyl)oxazol-4-yl]benzenesulfonamide;
4-[2-benzyl-5-(5-chloro-2-thienyl)oxazol-4-yl]benzenesulfonamide;
4-[2-benzyl-5-(cyclohexyl)oxazol-4-yl]benzenesulfonamide;
4-[2-benzyl-5-(1-cyclohexenyl)oxazol-4-yl]benzenesulfonamide;
4-[2-(ethyl)-5-phenyloxazol-4-yl]benzenesulfonamide;
4-[2-(trifluoromethyl)-5-phenyloxazol-4-yl]benzenesulfonamide;
4-[2-(difluoromethyl)-5-phenyloxazol-4-yl]benzenesulfonamide;
4-[2-(hydroxymethyl)-5-phenyloxazol-4-yl]benzenesulfonamide;
4-[2-(carboxy)-5-phenyloxazol-4-yl]benzenesulfonamide;
4-[2-(methoxycarbonyl)-5-phenyloxazol-4-yl]benzenesulfonamide;
4-[2-(ethoxycarbonyl)-5-phenyloxazol-4-yl]benzenesulfonamide;
4-[2-(n-propyl)-5-phenyloxazol-4-yl]benzenesulfonamide;
4-[2-(benzyl)-5-phenyloxazol-4-yl]benzenesulfonamide;
4-[2-(phenoxymethyl)-5-phenyloxazol-4-yl]benzenesulfonamide;
4-[2-((4-chlorophenoxy)methyl)-5-phenyloxazol-4-yl]benzenesulfonamide;
4-[2-((4-fluorophenoxy)methyl)-5-phenyloxazol-4-yl]benzenesulfonamide;
4-[2-((4-carboxyphenoxy)methyl)-5-phenyloxazol-4-yl]benzenesulfonamide;
4-[2-(2-phenethyl)-5-phenyloxazol-4-yl]benzenesulfonamide;
4-[2-(3-phenpropyl)-5-phenyloxazol-4-yl]benzenesulfonamide;
4-[2-(carboxymethyl)-5-phenyloxazol-4-yl]benzenesulfonamide;
4-[2-(ethoxycarbonylmethyl)-5-phenyloxazol-4-yl]benzenesulfonamide;
4-[2-(methoxycarbonylmethyl)-5-phenyloxazol-4-yl]benzenesulfonamide;
4-[2-(2-quinolyloxymethyl)-5-phenyloxazol-4-yl]benzenesulfonamide;
4-[2-benzyl-4-phenyloxazol-5-yl]benzenesulfonamide;
4-[2-benzyl-4-(3,4-difluorophenyl)oxazol-5-yl]benzenesulfonamide;
4-[2-benzyl-4-(4-chlorophenyl)oxazol-5-yl]benzenesulfonamide;
4-[2-benzyl-4-(3,4-dichlorophenyl)oxazol-5-yl]benzenesulfonamide;
4-[2-benzyl-4-(4-methoxyphenyl)oxazol-5-yl]benzenesulfonamide;
4-[2-benzyl-4-(3,4-dimethoxyphenyl)oxazol-5-yl]benzenesulfonamide;
4-[2-benzyl-4-(4-methylphenyl)oxazol-5-yl]benzenesulfonamide;
4-[2-benzyl-4-(3,4-dimethylphenyl)oxazol-5-yl]benzenesulfonamide;
4-[2-benzyl-4-(3-chloro-4-methylphenyl)oxazol-5-yl]benzenesulfonamide;
4-[2-benzyl-4-(4-chloro-3-methylphenyl)oxazol-5-yl]benzenesulfonamide;
4-[2-benzyl-4-(3-chloro-4-methoxyphenyl)oxazol-5-yl]benzenesulfonamide;
4-[2-benzyl-4-(4-chloro-3-methoxyphenyl)oxazol-5-yl]benzenesulfonamide;
4-[2-benzyl-4-(3,5-dichloro-4-methoxyphenyl)oxazol-5-yl]benzenesulfonamide;
4-[2-benzyl-4-(3-fluoro-4-methylphenyl)oxazol-5-yl]benzenesulfonamide;
4-[2-benzyl-4-(4-fluoro-3-methylphenyl)oxazol-5-yl]benzenesulfonamide;
4-[2-benzyl-4-(3-fluoro-4-methoxyphenyl)oxazol-5-yl]benzenesulfonamide;
4-[2-benzyl-4-(2-thienyl)oxazol-5-yl]benzenesulfonamide;
4-[2-benzyl-4-(5-chloro-2-thienyl)oxazol-5-yl]benzenesulfonamide;
4-[2-benzyl-4-(cyclohexyl)oxazol-5-yl]benzenesulfonamide;
4-[2-benzyl-4-(1-cyclohexenyl)oxazol-5-yl]benzenesulfonamide;
4-[2-(ethyl)-4-phenyloxazol-5-yl]benzenesulfonamide;
4-[2-(trifluoromethyl)-4-phenyloxazol-5-yl]benzenesulfonamide;
4-[2-(difluoromethyl)-4-phenyloxazol-5-yl]benzenesulfonamide;
4-[2-(hydroxymethyl)-4-phenyloxazol-5-yl]benzenesulfonamide;
4-[2-(carboxy)-4-phenyloxazol-5-yl]benzenesulfonamide;
4-[2-(methoxycarbonyl)-4-phenyloxazol-5-yl]benzenesulfonamide;

4-[2-(ethoxycarbonyl)-4-phenyloxazol-5-yl]benzenesulfonamide;
4-[2-(propyl)-4-phenyloxazol-5-yl]benzenesulfonamide;
4-[2-(benzyl)-4-phenyloxazol-5-yl]benzenesulfonamide;
4-[2-(phenoxymethyl)-4-phenyloxazol-5-yl]benzenesulfonamide;
4-[2-((4-chlorophenoxy)methyl)-4-phenyloxazol-5-yl]benzenesulfonamide;
4-[2-((4-fluorophenoxy)methyl)-4-phenyloxazol-5-yl]benzenesulfonamide;
4-[2-((4-carboxyphenoxy)methyl)-4-phenyloxazol-5-yl]benzenesulfonamide;
4-[2-(2-phenethyl)-4-phenyloxazol-5-yl]benzenesulfonamide;
4-[2-(3-phenpropyl)-4-phenyloxazol-5-yl]benzenesulfonamide;
4-[2-(carboxymethyl)-4-phenyloxazol-5-yl]benzenesulfonamide;
4-[2-(ethoxycarbonylmethyl)-4-phenyloxazol-5-yl]benzenesulfonamide;
4-[2-(methoxycarbonylmethyl)-4-phenyloxazol-5-yl]benzenesulfonamide;
4-[2-(2-quinolyloxymethyl)-4-phenyloxazol-5-yl]benzenesulfonamide;
4-[5-(4-fluorophenyl)-2-methyl-oxazol-4-yl]benzenesulfonamide;
3-[5-(4-fluorophenyl)-4-(4-aminosulfonylphenyl)oxazol-2-yl]propanoic acid;
methyl 3-[5-(4-fluorophenyl)-4-(4-aminosulfonylphenyl)oxazol-2-yl]propanate;
4-[4-(4-fluorophenyl)-2-(2-phenylethyl)-oxazol-5-yl]benzenesulfonamide;
4-[4-(4-fluorophenyl)-2-methyl-oxazol-5-yl]benzenesulfonamide;
4-[4-(4-fluorophenyl)-2-phenyloxazol-5-yl]benzenesulfonamide;
4-[2-benzyl-(4-4-fluorophenyl)oxazol-5-yl]benzenesulfonamide;
4-[4-(4-fluorophenyl)-2-(3-phenylpropyl)oxazol-5-yl]benzenesulfonamide;
4-[4-(4-fluorophenyl)-2-(n-propyl)oxazol-5-yl]benzenesulfonamide;
4-[2-(tert-butyl)-4-(4-fluorophenyl)oxazol-5-yl]benzenesulfonamide;
4-[4-(4-fluorophenyl)-2-(4-methoxyphenyl)methyloxazol-5-yl]benzenesulfonamide;
4-[4-(4-fluorophenyl)-2-(3-methoxyphenyl)methyloxazol-5-yl]benzenesulfonamide;
4-[2-(diphenylmethyl-4-(4-fluorophenyl)oxazol-5-yl]benzenesulfonamide;
4-[4-(4-fluorophenyl)-5-[4-aminosulfonylphenyl]oxazol-2-yl]acetic acid;
ethyl 2-[4-(4-fluorophenyl)-5-[4-aminosulfonylphenyl]oxazol-2-yl]acetate;
3-[4-(4-fluorophenyl)-5-[4-aminosulfonylphenyl]oxazol-2-yl]propanoic acid;
methyl 3-[4-(4-fluorophenyl)-5-[4-aminosulfonylphenyl]oxazol-2-yl]propanate;
4-[4-(4-fluorophenyl)-5-[4-aminosulfonylphenyl]oxazol-2-yl]butanoic acid;
methyl 4-[4-(4-fluorophenyl)-5-[4-aminosulfonyl phenyl]oxazol-2-yl]butanate;
3-[4-(4-fluorophenyl)-5-[4-aminosulfonyl phenyl]oxazol-2-yl]propanamide;
ethyl 2-[4-(4-fluorophenyl)-5-[4-aminosulfonyl phenyl]oxazol-2-yl]-2-benzyl-acetate;
4-[4-(4-fluorophenyl)-2-(cyclohexylethyl)oxazol-5-yl]benzenesulfonamide;
4-[4-(4-fluorophenyl)-2-(3-fluorophenoxymethyl)oxazol-5-yl]benzenesulfonamide;
4-[4-(4-fluorophenyl)-2-(3-chlorophenoxymethyl)oxazol-5-yl]benzenesulfonamide;
4-[4-(4-fluorophenyl)-2-(pyridyloxymethyl)oxazol-5-yl]benzenesulfonamide;
4-[4-(4-fluorophenyl)-2-phenoxymethyloxazol-5-yl]benzenesulfonamide;
4-[4-(4-fluorophenyl)-2-(2-hydroxyethyl)oxazol-5-yl]benzenesulfonamide;
4-[4-(4-fluorophenyl)-2-(hydroxymethyl)oxazol-5-yl]benzenesulfonamide;
4-[4-(cyclohexyl)-2-phenyloxazol-5-yl]benzenesulfonamide;
4-[4-(4-fluorophenyl)-2-benzyloxymethyloxazol-5-yl]benzenesulfonamide;
4-[4-(4-fluorophenyl)-2-cyclohexyloxazol-5-yl]benzenesulfonamide; and
4-[5-(4-fluorophenyl)-2-phenyloxazol-4-yl]benzenesulfonamide.

37. The method of claim 25 for the treatment of inflammation.

38. The method of claim 25 for the treatment of an inflammation-associated disorder.

39. The method of claim 38 wherein the inflammation-associated disorder is arthritis.

40. The method of claim 38 wherein the inflammation-associated disorder is pain.

41. The method of claim 38 wherein the inflammation-associated disorder is fever.

* * * * *